United States Patent
Lee et al.

(10) Patent No.: US 9,493,494 B2
(45) Date of Patent: Nov. 15, 2016

(54) PHOSPHININE OXIDE DERIVATIVE AND PREPARATION METHOD THEREOF

(71) Applicant: KNU-INDUSTRY COOPERATION FOUNDATION, Chuncheon-si, Gangwon-do (KR)

(72) Inventors: Phil Ho Lee, Chuncheon-si (KR); Young Chul Park, Chuncheon-si (KR); In Cheol Jeon, Chuncheon-si (KR); Jung Min Seo, Chuncheon-si (KR); Bo Ram Seo, Chuncheon-si (KR)

(73) Assignee: Knu-Industry Cooperation Foundation, Chuncheon-si (KR)

(*) Notice: Subject to any disclaimer, the term of this patent is extended or adjusted under 35 U.S.C. 154(b) by 0 days.

(21) Appl. No.: 14/473,901

(22) Filed: Aug. 29, 2014

(65) Prior Publication Data

US 2015/0344506 A1 Dec. 3, 2015

(30) Foreign Application Priority Data

May 30, 2014 (KR) .................. 10-2014-0065859

(51) Int. Cl.
*C07F 9/6584* (2006.01)
*C07F 9/6571* (2006.01)

(52) U.S. Cl.
CPC ..... *C07F 9/65846* (2013.01); *C07F 9/657163* (2013.01); *C07F 9/657172* (2013.01); *C07F 9/657181* (2013.01)

(58) Field of Classification Search
None
See application file for complete search history.

(56) References Cited

PUBLICATIONS

Unoh, et al., Org. Lett., 15:3258 (Jun. 17, 2013).*
Peng, A. et al., "The Synthesis of Phosphaisocoumarins by Cu(I)-Catalyzed Intramolecular Cyclization of o-Ethynylphenylphosphonic Acid Monoesters," J. Am. Chem. Soc., vol. 125, No. 49, pp. 15006-15007, Dec. 2003, 2 pages.
Tang, W. et al., "Synthesis of Phophaisoquinolin-1-ones by Pd(II)-Catalyzed Cyclization of o-(1-Alkynyl) phenylphosphonomide Monoesters," J. Org. Chem., vol. 71, No. 22, pp. 8489-8492, Oct. 2006, 4 pages.
Mo, J. et al., "Gold-Catalyzed Sequential Alkyne Activation for the Synthesis of 4,6-Disubstituted Phosphorus 2-Pyrones," Org. Lett., vol. 15, No. 1, pp. 26-29, Jan. 2013, Available Online Dec. 13, 2012, 4 pages.
Seo, J. et al., "Synthesis of Phosphaisocoumarins through Rhodium-Catalyzed Cyclization Using Alkynes and Arylphosphonic Acid Monoesters," Org. Lett., vol. 15, No. 13, pp. 3358-3361, Jul. 2013, Available Online Jun. 21, 2013, 16 pages, (includes abstracts for 6 subsequent presentations of the publication).
Park, S. et al., "Rhodium-Catalyzed Oxidative Coupling Through C—H Activation and Annulation Directed by Phosphonamide and Phosphinamide Groups," Chem. Commun., vol. 49, No. 77, pp. 8671-8673, Oct. 2013, Available Online Jul. 25, 2013, 144 pages, (includes supplementary material and abstracts for 7 subsequent presentations of the publication).
Park, Y. et al., "Ruthenium-Catalyzed C—H Activation/Cyclization for the Synthesis of Phosphaisocoumarins," J. Org. Chem., vol. 78, No. 20, pp. 10209-10220, Oct. 2013, Available Online Sep. 12, 2013, 20 pages, (includes abstracts for 4 subsequent presentations of the publication).
Park, Y. et al., "Rhodium-Catalyzed Oxidative C—H Activation/Cyclization for the Synthesis of Phosphaisocoumarins and Phosphorous 2-Pyrones," Chem. Eur. J., vol. 19, No. 48, pp. 16461-16468, Nov. 2013, Available Online Oct. 10, 2013, 21 pages, (includes abstracts for 7 subsequent presentations of the publication).
Seo, B., "Synthesis of Phosphaisoquinolin-1-one Via Rhodium-Catalyzed C—H Bond Activation and Annulaion of Arylphosphinic Amide with Alkyne," Masters Thesis, Dept. of Chemistry, Kangwon National University, Chuncheun 200-701, Republic of Korea, Feb. 2014, 91 pages, (abstract in english).

* cited by examiner

*Primary Examiner* — Michael Barker
(74) *Attorney, Agent, or Firm* — Alleman Hall McCoy Russell & Tuttle LLP

(57) ABSTRACT

Provided are a novel phosphinine oxide derivative and a preparation method thereof, and more specifically, the phosphinine oxide derivative includes an oxaphosphinine oxide derivative and an azaphosphinine oxide derivative.

The phosphinine oxide derivative according to the present invention may have a pharmacological activity and a physiological activity, and may be used as a basic framework of a natural product and may be used for development of new drug and synthesis of various medical supplies.

In addition, according to the preparation method of the phosphinine oxide derivative according to the present invention, various phosphinine oxide derivatives with a high yield may be prepared by a simple synthesis process using an intramolecular annulation between a phosphinic derivative and an alkyne derivative in the presence of a rhodium (Rh) catalyst or a ruthenium (Ru) catalyst and an oxidant.

14 Claims, No Drawings

PHOSPHININE OXIDE DERIVATIVE AND PREPARATION METHOD THEREOF

CROSS-REFERENCE TO RELATED APPLICATIONS

This application claims priority under to Korean Patent Application No. 10-2014-0065859, filed on May 30, 2014, the entire contents of which are hereby incorporated by reference for all purposes.

TECHNICAL FIELD

The following disclosure relates to a novel phosphinine oxide derivative and a preparation method thereof, and more specifically, the phosphinine oxide derivative includes an oxaphosphinine oxide derivative and an azaphosphinine oxide derivative.

BACKGROUND

A heterocyclic compound constitutes a basic framework of a natural product and an organic phosphorus compound has a pharmacologic activity and a physiological activity. The organic phosphorus compound is largely related with biological phenomenon, many synthesis methods thereof have been attempted to be developed and studied depending on new physiological functions thereof, and in particular, chemical reactivity and physiological relation between carbon in an organic compound and phosphorus in an organic phosphorus compound having a similar structure to the organic compound have received attention.

In particular, a phosphaisocoumarin derivative which is one of a phosphorus heterocyclic compound has a similar activity to a coumarin derivative used as a precursor of perfume, seasoning, and other chemicals. That is, the phosphaisocoumarin derivative may be used as an important precursor preparing medical supplies. A phosphorus 2-pyrone derivative is used for synthesis of various medical supplies including a HIV protease inhibitor, and the like.

Therefore, many researches of developing the synthesis method of the phosphaisocoumarin derivative and the phosphorus 2-pyrone derivative have been conducted (*J. Org. Chem.* 2006, 71, 8489; *Org. Lett.* 2013, 15, 26; *J. Am. Chem. Soc.* 2003, 125, 15006).

A preparation method of the phosphaisocoumarin derivative and the phosphorus 2-pyrone derivative with a high yield by annulation between a phosphinic derivative and various alkynes in the presence of a rhodium (Rh) catalyst or a ruthenium (Ru) catalyst has not been reported yet.

Meanwhile, an isoquinolin-1-one derivative is a significantly important compound showing physiological activities such as an anti-cancer function, function on a toxic cell, function on cardiovascular system, an anti-tumor function, an antibacterial function, inhibition of human thymidylate, inhibition of PARP activity, and maximal blood pressure reduction.

As the existing synthesis method of a phosphaisoquinoline-1-one compound, a synthesis method using o-(1-alkynyl)phenylphosphonamide monoester in the presence of a palladium catalyst is known (*J. Org. Chem.* 2006, 71, 8489.); however, with the synthesis method, phosphaisoquinoline-1-one having a substituent introduced at a position No. 4 of a product by an intramolecular annulation may not be synthesized. Recently, a synthesis method of novel phosphaisoquinoline-1-one and a derivative thereof by an olefin reaction with alkyne, and a subsequent annulation reaction through an activation reaction of a carbon-hydrogen bond using a phosphonyl group as a directing group has not been recently reported, and thus, a novel synthesis method of various phosphaisoquinoline-1-one compounds using the same is required to be developed.

SUMMARY

An embodiment of the present invention is directed to providing a novel phosphinine oxide derivative having a pharmacologic activity and a physiological activity.

In addition, another embodiment of the present invention is directed to providing a preparation method thereof.

In one general aspect, the present invention provides a phosphinine oxide derivative represented by the following Chemical Formula 1:

[Chemical Formula 1]

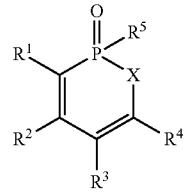

in Chemical Formula (1),

X is NR' or O;

R' is C1-C20 alkyl or C6-C20 aryl;

$R^1$ and $R^2$ are each independently hydrogen, C1-C20 alkyl or C6-C20 aryl, or $R^1$ and $R^2$ may be linked to each other by —$CR^{11}$=$CR^{12}$—$CR^{13}$=$CR^{14}$— or -L-$CR^{15}$=$CR^{16}$— to form a fused ring;

$R^{11}$ to $R^{16}$ are each independently hydrogen, C1-C20 alkyl, halo C1-C20 alkyl, C1-C20 alkoxy, C6-C20 aryl, halogen, C1-C20 alkylcarbonyl or hydroxyl, or may be linked to an adjacent substituent by C2-C7 alkenylene, C2-C7 alkylenedioxy or —$CR^{17}$=$CR^{18}$—OC(=O)— to form a fused ring;

$R^{17}$ and $R^{18}$ are each independently C1-C20 alkyl or C6-C20 aryl;

L is NR", O or S;

R" is hydrogen or C1-C20 alkyl;

$R^3$ and $R^4$ are each independently C1-C20 alkyl or C6-C20 aryl; and $R^5$ is C1-C20 alkoxy, C6-C20 aryl or C3-C20 heteroaryl, wherein the alkyl and aryl of $R^1$, $R^2$, $R^3$ and $R^4$, and the alkoxy, aryl, and heteroaryl of $R^5$ may be further substituted with at least one substituent selected from the group consisting of halogen, C1-C20 alkyl, C1-C20 alkoxy and halo C1-C20 alkyl, respectively.

In another general aspect, the present invention provides a preparation method of a phosphinine oxide derivative represented by the Chemical Formula 1, by an intramolecular annulation between a phosphinic derivative represented by the following Chemical Formula 5 and an alkyne derivative represented by the following Chemical Formula 6, in the presence of a catalyst and an oxidant:

[Chemical Formula 5]

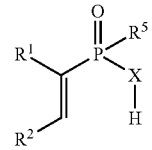

-continued

[Chemical Formula 6]

Hereinafter, the present invention will be described in detail.

Here, unless technical and scientific terms used herein are defined otherwise, they have meanings generally understood by those skilled in the art to which the present invention pertains. In addition, the repeated descriptions for technical constitution and function as the same as the related art will be omitted.

The present invention provides a phosphinine oxide derivative represented by the following Chemical Formula 1:

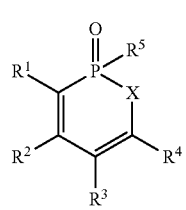
[Chemical Formula 1]

in Chemical Formula (1),

X is NR' or O;

R' is C1-C20 alkyl or C6-C20 aryl;

$R^1$ and $R^2$ are each independently hydrogen, C1-C20 alkyl or C6-C20 aryl, or $R^1$ and $R^2$ may be linked to each other by —$CR^{11}$=$CR^{12}$—$CR^{13}$=$CR^{14}$— or -L-$CR^{15}$=$CR^{16}$— to form a fused ring;

$R^{11}$ to $R^{16}$ are each independently hydrogen, C1-C20 alkyl, halo C1-C20 alkyl, C1-C20 alkoxy, C6-C20 aryl, halogen, C1-C20 alkylcarbonyl or hydroxyl, or may be linked to an adjacent substituent by C2-C7 alkenylene, C2-C7 alkylenedioxy or —$CR^{17}$=$CR^{18}$—OC(=O)— to form a fused ring;

$R^{17}$ and $R^{18}$ are each independently C1-C20 alkyl or C6-C20 aryl;

L is NR'', O or S;

R'' is hydrogen or C1-C20 alkyl;

$R^3$ and $R^4$ are each independently C1-C20 alkyl or C6-C20 aryl; and $R^5$ is C1-C20 alkoxy, C6-C20 aryl or C3-C20 heteroaryl, wherein the alkyl and aryl of R', $R^2$, $R^3$ and $R^4$, and the alkoxy, aryl, and heteroaryl of $R^5$ may be further substituted with at least one substituent selected from the group consisting of halogen, C1-C20 alkyl, C1-C20 alkoxy and halo C1-C20 alkyl, respectively.

Terms: alkyl, alkoxy described in the present invention include both of linear type and branched type.

Term: aryl described in the present invention, which is an organic radical derived from aromatic hydrocarbon due to removal of one hydrogen, includes a single ring system or a fused ring system including 4 to 7 ring atoms, and preferably, 5 or 6 ring atoms in each ring, and even includes a form in which a plurality of aryls are connected by a single bond. Specific examples of the aryl include aromatic groups such as phenyl, naphthyl, biphenyl, indenyl, fluorenyl, phenanthrenyl, anthracenyl, triphenylenyl, pyrenyl, crycenyl and naphthacenyl.

Term: heteroaryl described in the present invention, which means an aryl group containing 1 to 4 heteroatoms selected from N, O, and S as an aromatic ring framework atom and carbon as the remaining aromatic ring framework atom, is a 5- to 6-membered monocyclic heteroaryl and a polycyclic heteroaryl condensed with at least one benzene ring, and may be partially saturated. In addition, heteroaryl in the present invention includes a form in which one or more heteroaryls are connected by a single bond. Examples of the heteroaryl group include pyrrole, quinoline, isoquinoline, pyridine, pyrimidine, oxazole, thiazole, thiadiazole, triazole, imidazole, benzimidazole, isoxazole, thiophene, benzothiophene, furan and benzofuran.

The novel phosphinine oxide derivative represented by the Chemical Formula 1 of the present invention may include an oxaphosphinine oxide derivative and an azaphosphinine oxide derivative, and preferably, may be represented by the following Chemical Formula 2, 3, or 4:

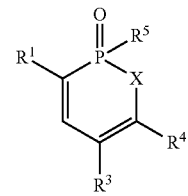
[Chemical Formula 2]

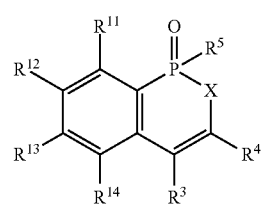
[Chemical Formula 3]

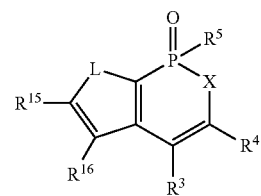
[Chemical Formula 4]

in Chemical Formulas 2 to 4, X, $R^3$, $R^4$ and $R^5$ are the same as defined above, $R^1$ is C1-C20 alkyl or C6-C20 aryl;

$R^{11}$ to $R^{16}$ are each independently hydrogen, C1-C20 alkyl, halo C1-C20 alkyl, C1-C20 alkoxy, C6-C20 aryl, halogen, C1-C20 alkylcarbonyl, or hydroxyl, or may be linked to an adjacent substituent by

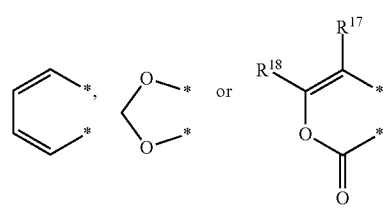

to form a fused ring;

L is NR'' or S; and

R'' is hydrogen or C1-C20 alkyl.

Specifically, in Chemical Formulas 2 to 4, X may be NR' or O; R' may be methyl, ethyl, propyl, butyl, pentyl, hexyl, phenyl or naphthyl; $R^1$ may be methyl, ethyl, propyl, butyl, pentyl, hexyl, heptyl, octyl, phenyl, naphthyl, fluorenyl, wherein the phenyl, naphthyl or fluorenyl of $R^1$ may be further substituted with at least one substituent selected from the group consisting of methyl, ethyl, propyl, butyl, pentyl, hexyl, chloro, bromo, fluoro and iodo; $R^{11}$ to $R^{16}$ may be each independently hydrogen, methyl, ethyl, propyl, butyl, pentyl, hexyl, methoxy, ethoxy, propoxy, butoxy, pentyloxy, hexyloxy, fluoro, chloro, iodo, bromo, acetyl, trifluoromethyl, phenyl, naphthyl, or hydroxyl, or $R^{11}$ to $R^{14}$ may be linked to an adjacent substituent by

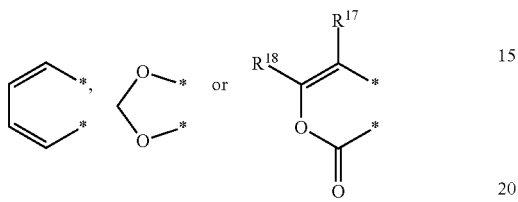

to form a fused ring, and $R^{15}$ and $R^{16}$ may be linked to each other by

to form a fused ring; $R^{17}$ and $R^{18}$ may be each independently methyl, ethyl, propyl, butyl, pentyl, hexyl, phenyl or naphthyl; L may be NH or S; $R^3$ and $R^4$ may be each independently methyl, ethyl, propyl, butyl, pentyl, hexyl, phenyl or naphthyl, wherein the phenyl or naphthyl of $R^3$ and $R^4$ may be further substituted with at least one substituent selected from the group consisting of methyl, ethyl, propyl, butyl, pentyl, hexyl, chloro, bromo, fluoro and iodo; $R^5$ may be methoxy, ethoxy, propoxy, butoxy, pentyloxy, hexyloxy, phenyl, naphthyl, thiophenyl, furyl, pyrrolyl, pyridyl, pyrimidinyl, quinolyl, triazolyl, oxazolyl or thiazolyl, wherein the phenyl of $R^5$ may be further substituted with at least one substituent selected from the group consisting of methyl, ethyl, propyl, butyl, pentyl, hexyl, trifluoromethyl, methoxy, ethoxy, propoxy, butoxy, pentyloxy, hexyloxy, chloro, bromo, fluoro and iodo.

The phosphinine oxide derivative may be selected from the following compounds, but the present invention is not limited thereto:

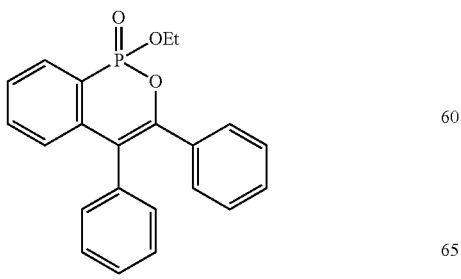

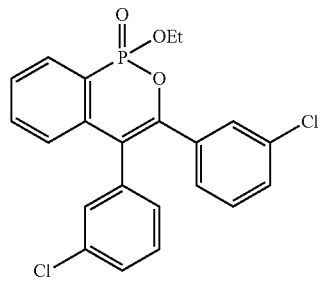

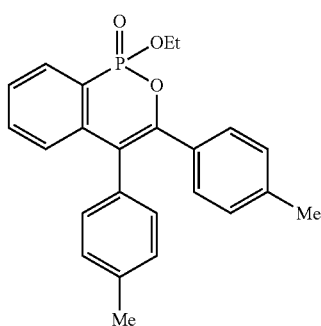

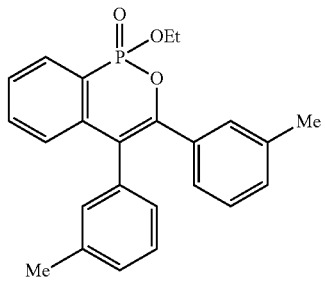

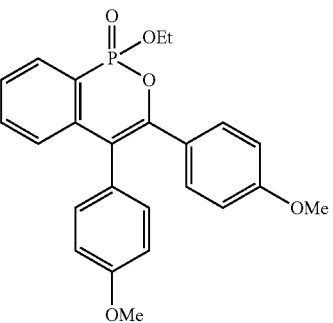

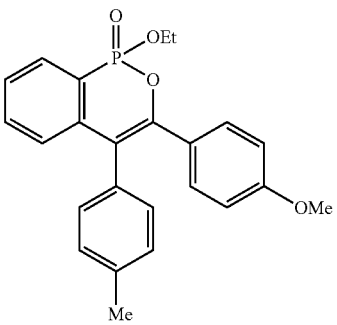

-continued
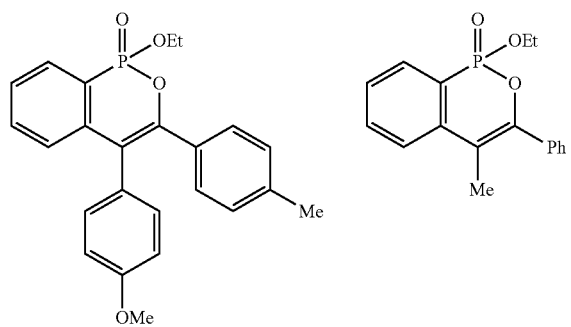
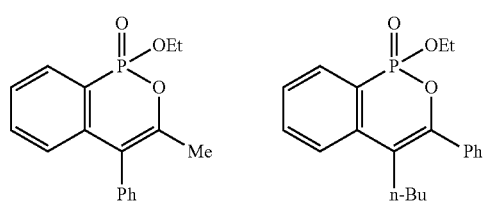
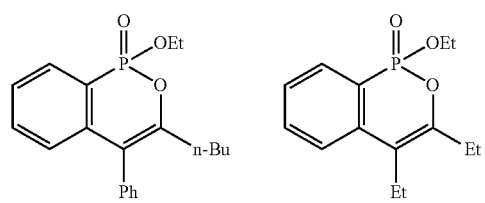
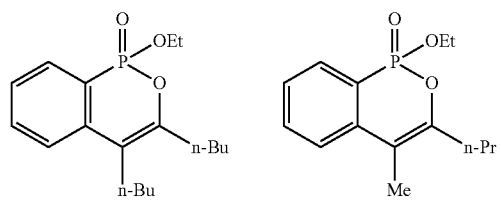
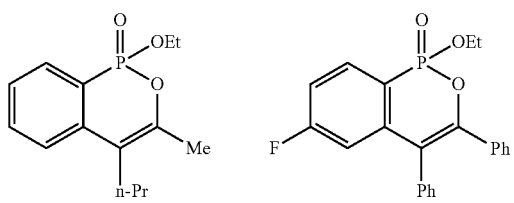
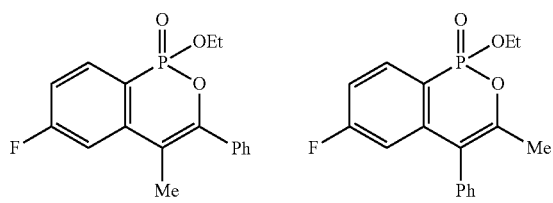
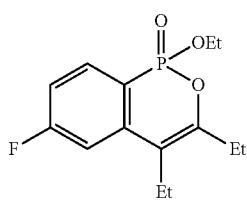
-continued
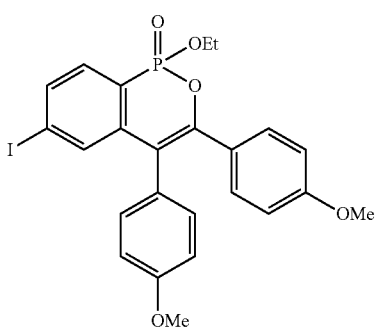
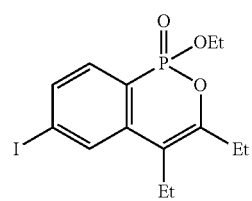
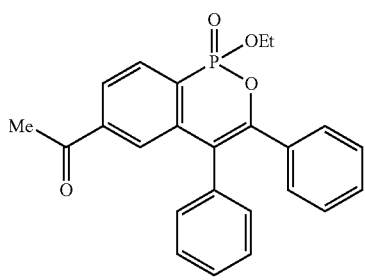
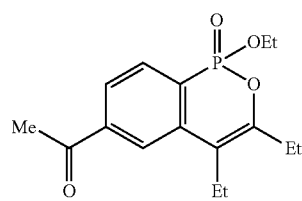
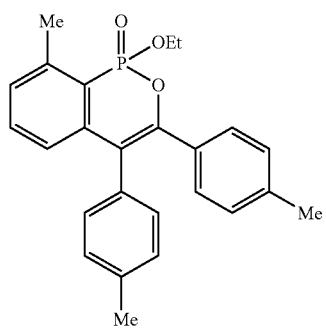
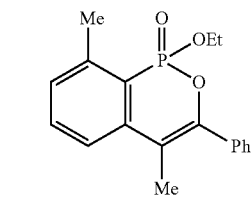
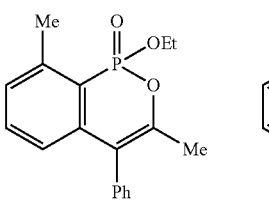
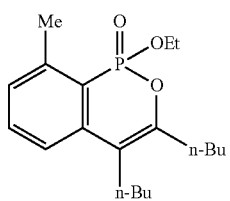

-continued
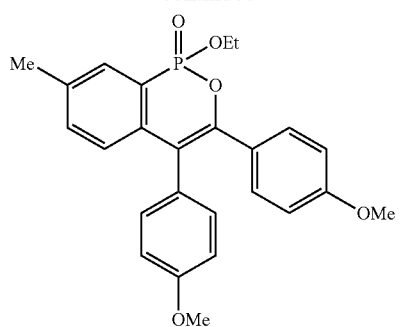
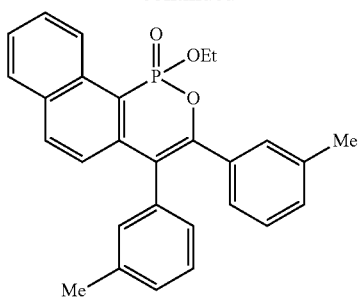
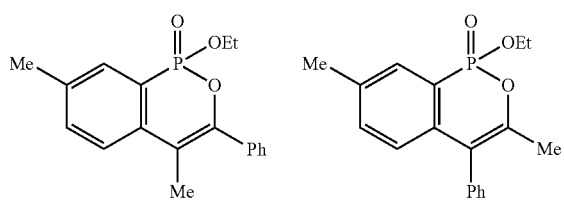
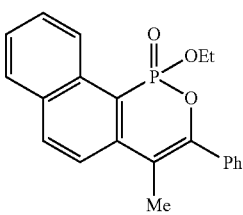
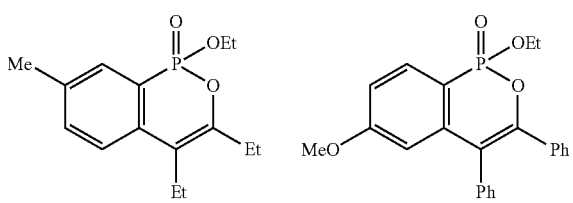
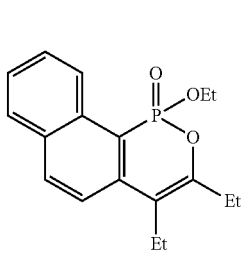
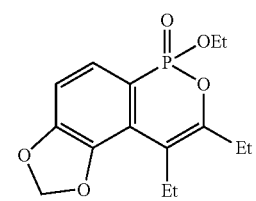
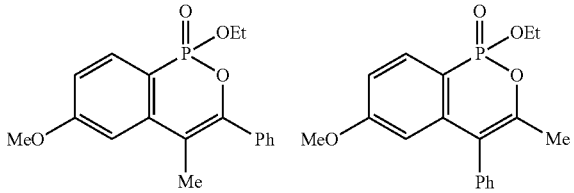
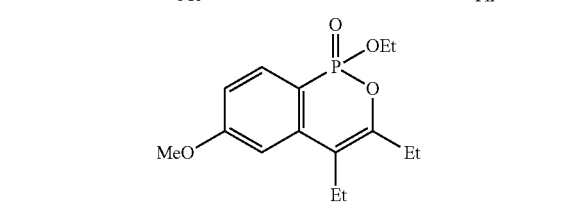
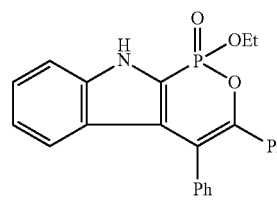
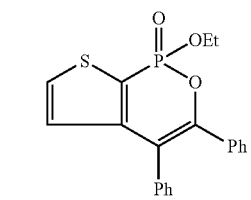
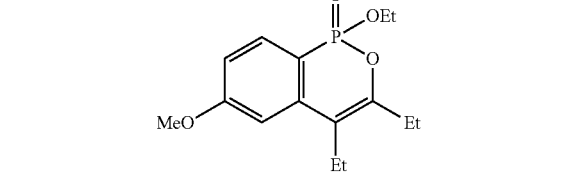
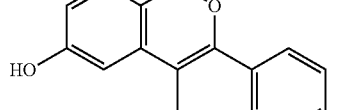
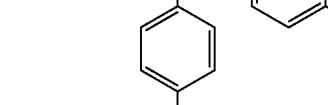
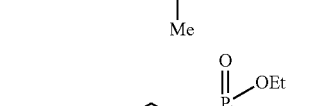
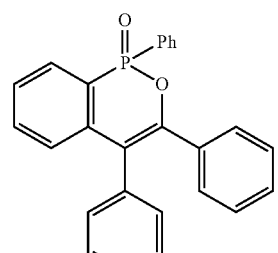
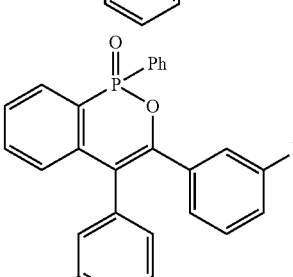

-continued
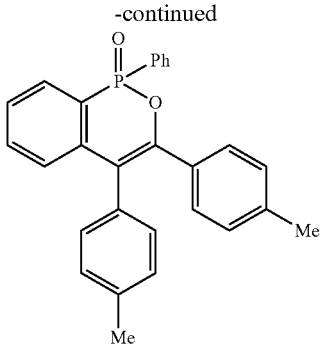
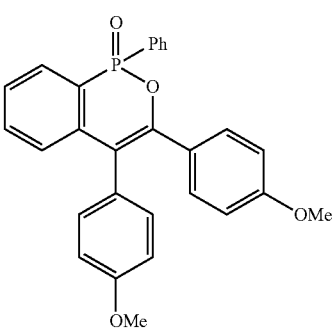
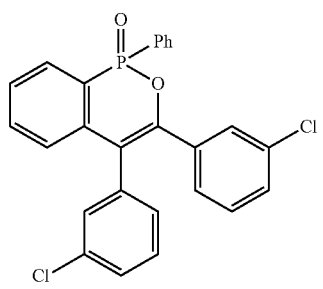
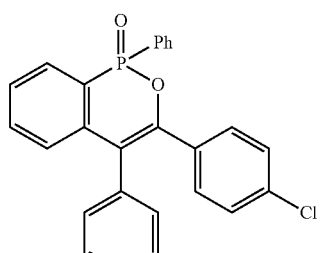
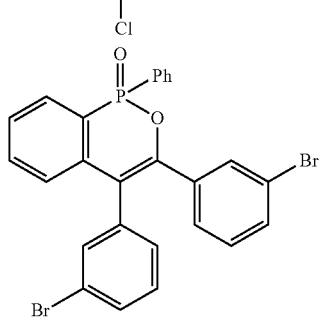
-continued
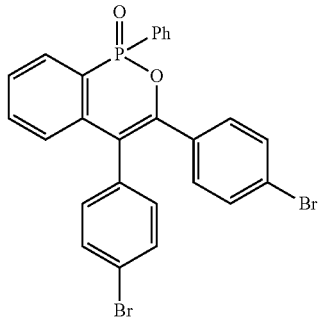
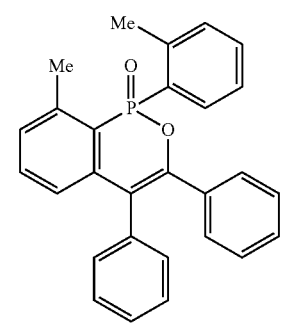
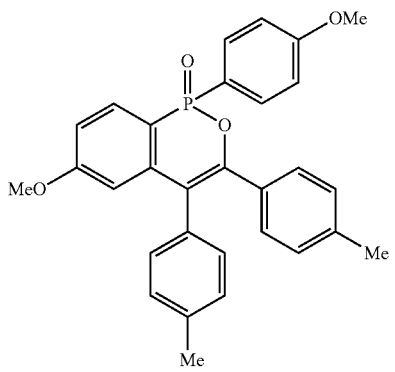
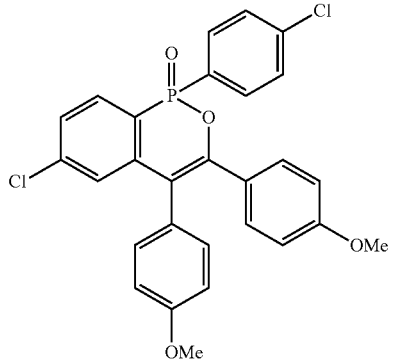

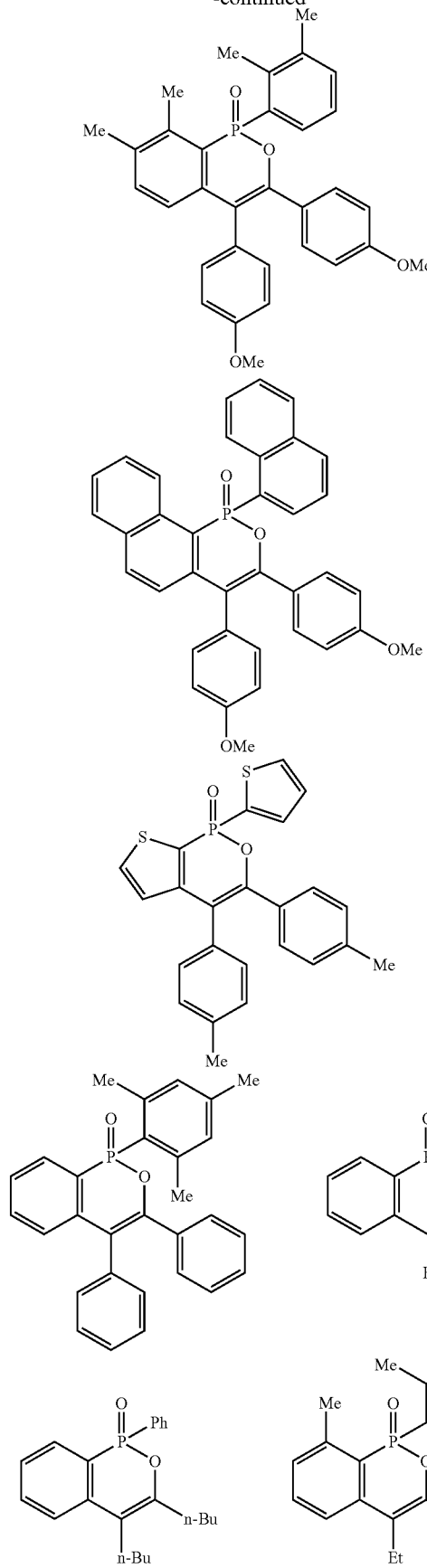
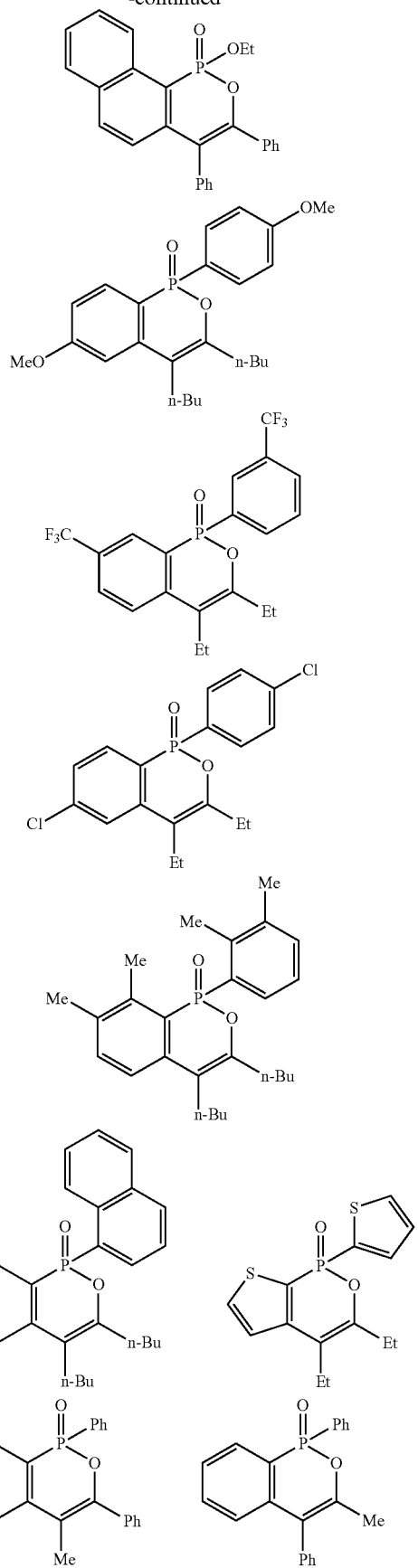

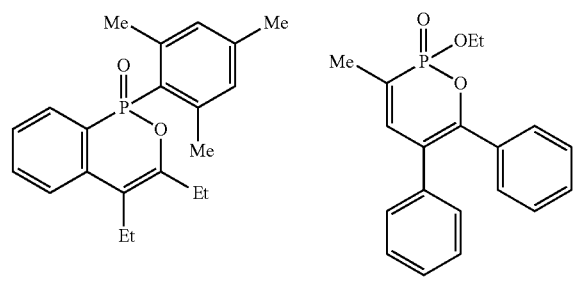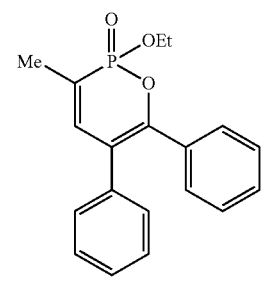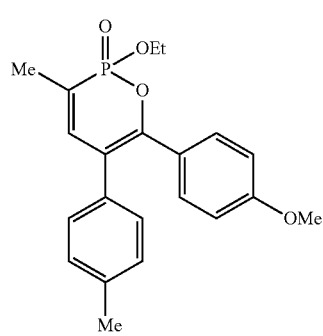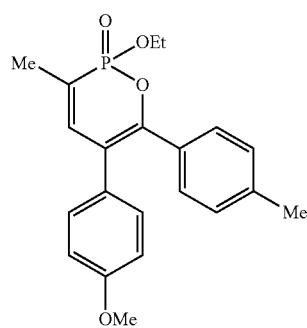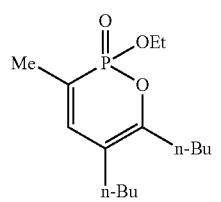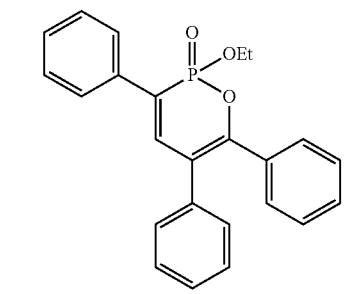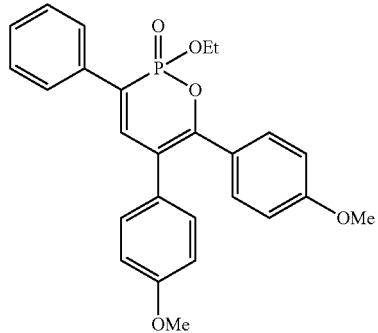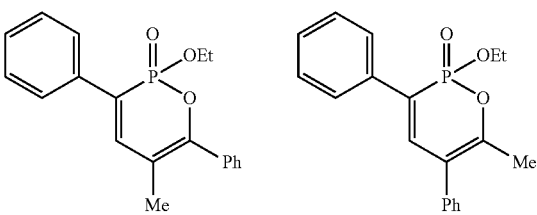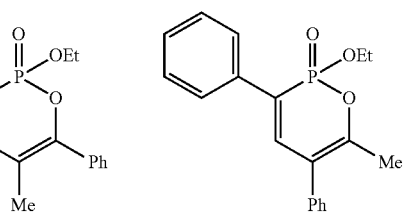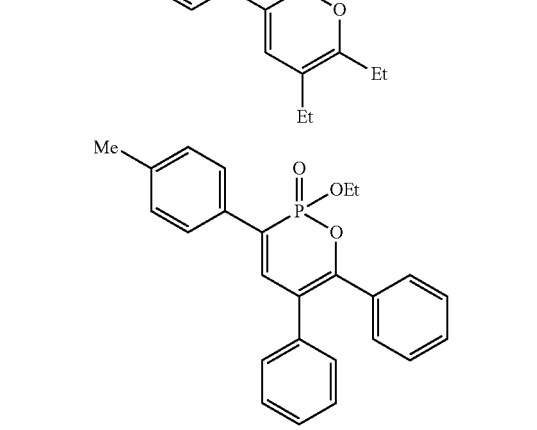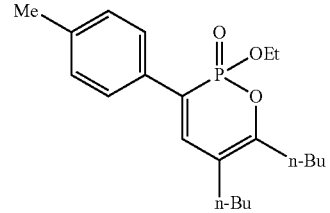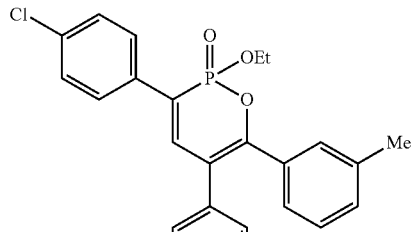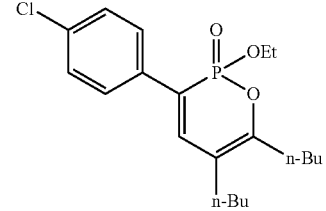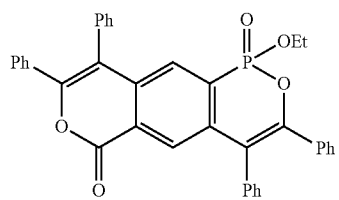

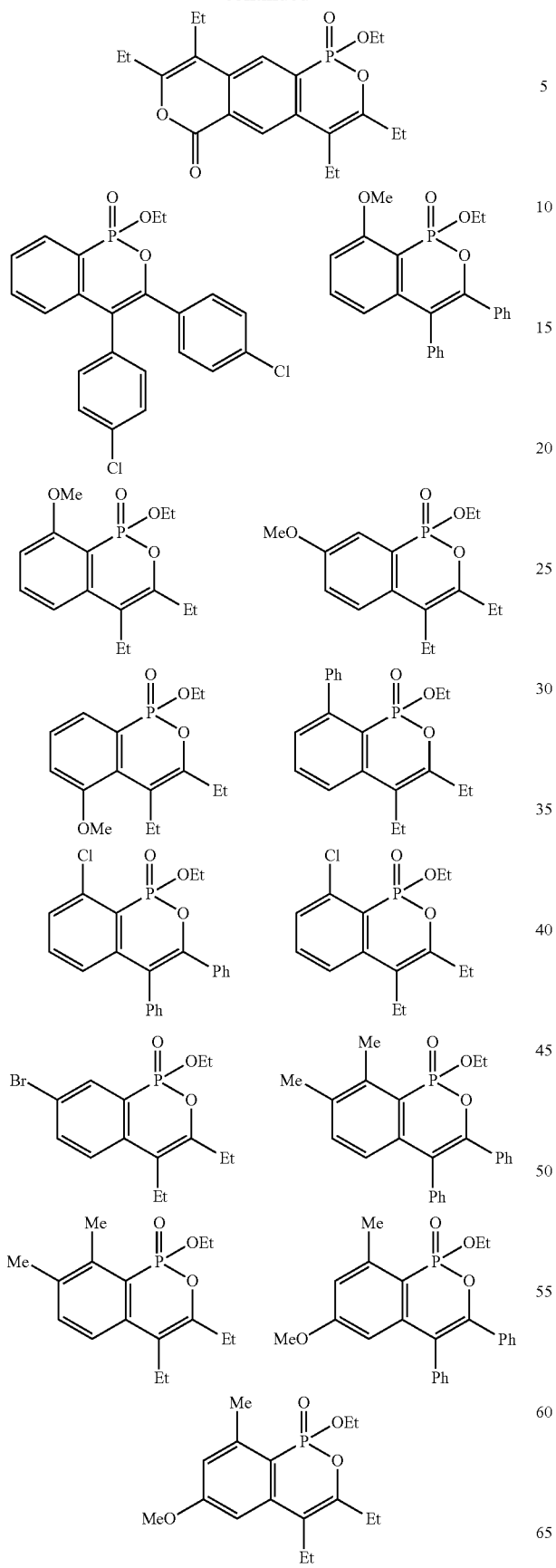
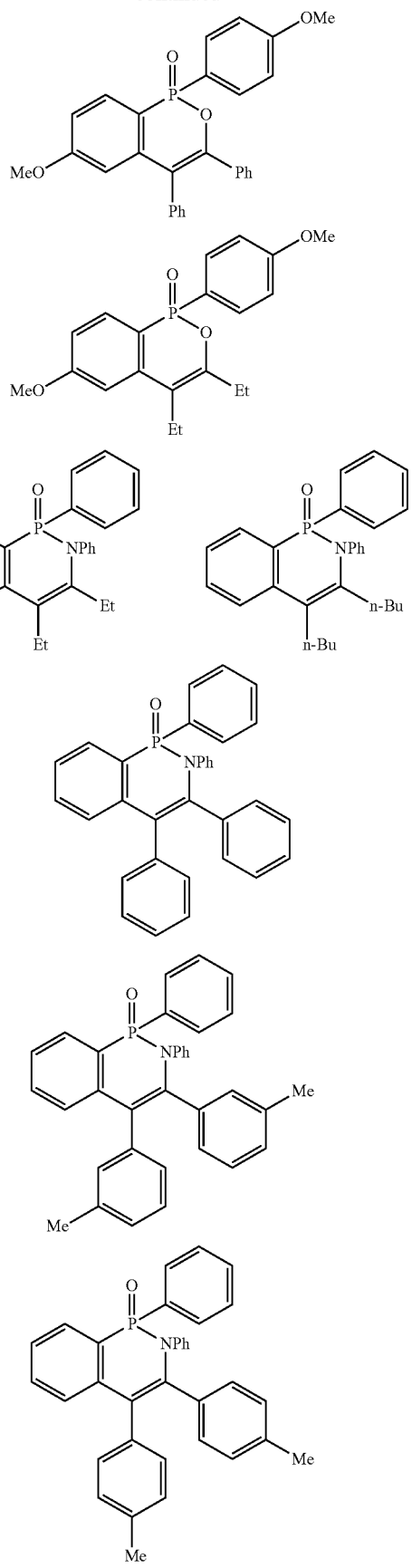

-continued
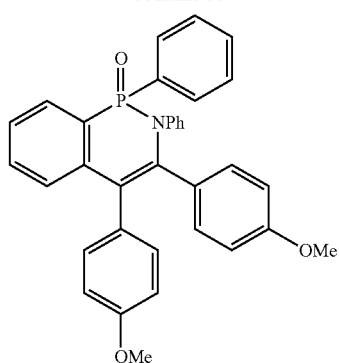
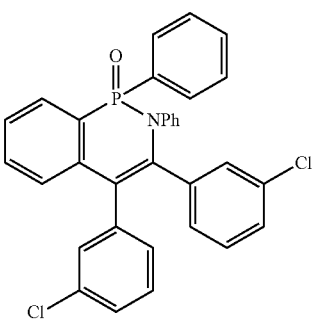
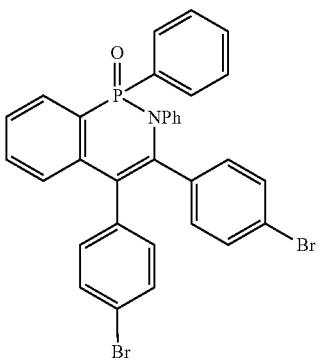
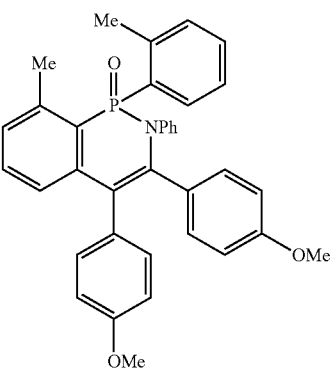
-continued
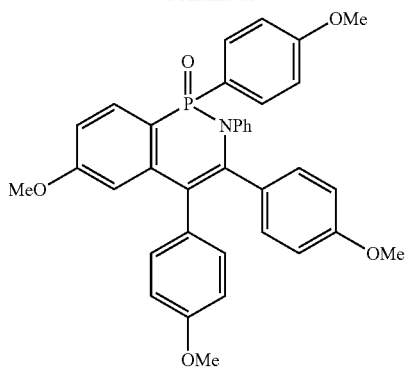
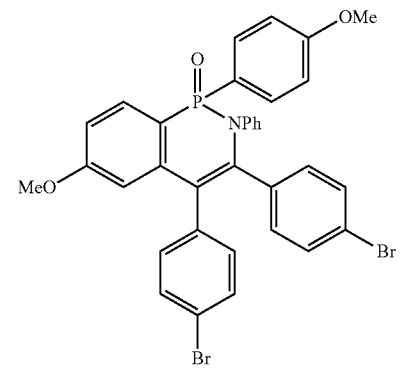
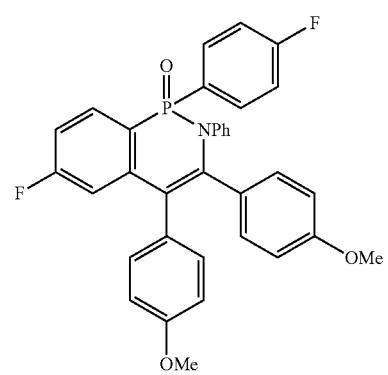
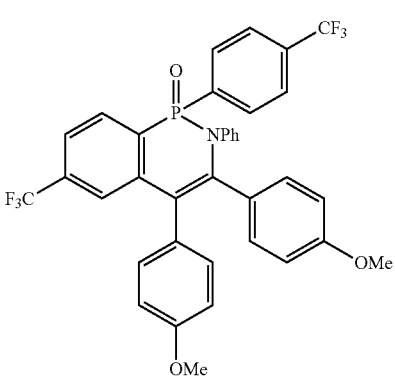

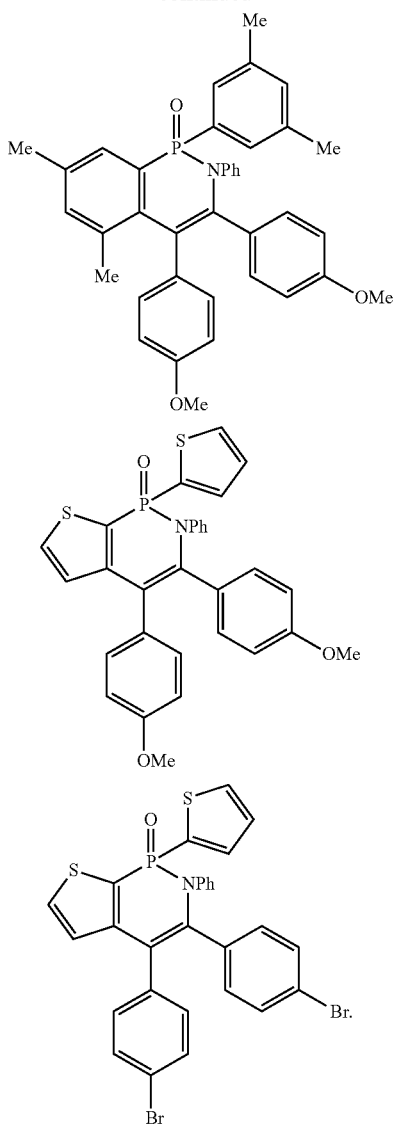

Hereinafter, a preparation method of a phosphinine oxide derivative according to the present invention will be described in detail.

In another general aspect, the present invention provides a preparation method of a phosphinine oxide derivative represented by the following Chemical Formula 1, by an intramolecular annulation between a phosphinic derivative represented by the following Chemical Formula 5 and an alkyne derivative represented by the following Chemical Formula 6, in the presence of a catalyst and an oxidant:

[Chemical Formula 1]

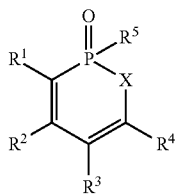

[Chemical Formula 5]

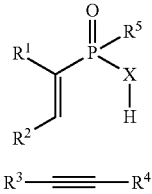

[Chemical Formula 6]

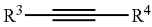

in Chemical Formulas 1, 5, and 6,

X is NR' or O;

R' is C1-C20 alkyl or C6-C20 aryl;

$R^1$ and $R^2$ are each independently hydrogen, C1-C20 alkyl or C6-C20 aryl, or $R^1$ and $R^2$ may be linked to each other by —$CR^{11}$=$CR^{12}$—$CR^{13}$=$CR^{14}$— or -L-$CR^{15}$=$CR^{16}$— to form a fused ring;

$R^{11}$ to $R^{16}$ are each independently hydrogen, C1-C20 alkyl, halo C1-C20 alkyl, C1-C20 alkoxy, C6-C20 aryl, halogen, C1-C20 alkylcarbonyl or hydroxyl, or may be linked to an adjacent substituent by C2-C7 alkenylene, C2-C7 alkylenedioxy or —$CR^{17}$=$CR^{18}$—OC(=O)— to form a fused ring;

$R^{17}$ and $R^{18}$ are each independently C1-C20 alkyl or C6-C20 aryl;

L is NR", O or S;

R" is hydrogen or C1-C20 alkyl;

$R^3$ and $R^4$ are each independently C1-C20 alkyl or C6-C20 aryl; and $R^5$ is C1-C20 alkoxy, C6-C20 aryl or C3-C20 heteroaryl, wherein the alkyl and aryl of R', $R^2$, $R^3$ and $R^4$, and the alkoxy, aryl, and heteroaryl of $R^5$ may be further substituted with at least one substituent selected from the group consisting of halogen, C1-C20 alkyl, C1-C20 alkoxy and halo C1-C20 alkyl, respectively.

The preparation method of the phosphinine oxide derivative represented by the Chemical Formula 1 according to the present invention is a significantly effective method capable of obtaining a product with a high yield and purity by a simple process and under a mild condition in the presence of the catalyst and the oxidant.

The catalyst used in the preparation method of the phosphinine oxide derivative according to the present invention may be a rhodium (Rh) catalyst or a ruthenium (Ru) catalyst, wherein the rhodium (Rh) catalyst may be one or a mixture of two or more selected from the group consisting of di-chlorobis(1,5-cyclooctadiene)dirhodium(I)([RhCl(cod)]$_2$), chlorobis(ethylene)rhodium(I)dimer ([RhCl(C$_2$H$_4$)$_2$]$_2$), rhodium(III)acetylacetonate(Rh(acac)$_3$), anhydrous rhodium chloride (III)(RhCl$_3$), rhodium chloride (III) hydrate (RhCl$_3$.xH$_2$O, x is an integer of 1 to 3), rhodium (III) bromide hydrate (RhBr$_3$.xH$_2$O, x is an integer of 1 to 3), rhodium (III) oxide (Rh$_2$O$_3$), rhodium (III) oxide hydrate (Rh$_2$O$_3$.xH$_2$O), tris(acetonitrile)pentamethyl cyclopentadienyl rhodium (III) hexafluoroantimonate ([(C$_5$Me$_5$)Rh(MeCN)$_3$][SbF$_6$]$_2$), dichloro(pentamethylcyclopentadienyl) rhodium(III) dimer ([Rh(C$_5$Me$_5$)Cl$_2$]$_2$), trichlorotri(ethylenediamine) rhodium(III) trihydrate ((H$_2$NCH$_2$CH$_2$NH$_2$)$_3$RhCl$_3$.3H$_2$O), chlorobis(2-phenylpyridine)rhodium(III) dimer, dichloro(dimethylglyoximato)(dimethylglyoxime) rhodium(III)), trichloro[1,1,1-tri(diphenylphosphinomethyl)ethane]rhodium(III), rhodium (III) iodide (RhI$_3$), rhodium (III) 2,4-pentene dionate and rhodium (III) sulfate tetrahydrate (Rh$_2$(SO$_4$)$_3$.4H$_2$O), and the ruthenium (Ru)

catalyst may be one or a mixture of two or more selected from the group consisting of dichloro(p-cymene)ruthenium (II)dimer ($[RuCl_2(p\text{-cymene})]_2$), benzene ruthenium (II) chloride dimer ($[RuCl_2(benzene)]_2$), tris(acetonitrile)pentamethylcyclopentadienyl ruthenium (II) hexafluorophosphate (($C_5Me_5)Ru(CH_3CN)_3PF_6$), dicarbonyltris(triphenylphosphine)ruthenium(0) ($Ru(CO)_2(PPh_3)_3$), carbonyldihydridotris(triphenylphosphine)ruthenium(II) ($RuH_2(CO)(PPh_3)_3$), triruthenium dodecacarbonyl ($Ru_3(CO)_{12}$), dichloro(1,5-cyclooctadiene)ruthenium(II) ($[Ru(COD)Cl_2]_x$), tris(triphenylphosphine)ruthenium(II) dichloride ($RuCl_2(PPh_3)_3$), dihydridotetrakis(triphenylphosphine)ruthenium(II) ($RuH_2(PPh_3)_4$), $RuH_2(H_2)_2(PCy_3)_2$ (Cy=cyclohexyl), ruthenium(III) chloride ($RuCl_3$), ruthenium(III) chloride hydrate ($RuCl_3.3H_2O$) and ruthenium(III) acetylacetonate ($Ru(acac)_3$). Preferably, $[Rh(C_5Me_5)Cl_2]_2$ may be used as the rhodium (Rh) catalyst, and $[RuCl_2(p\text{-cymene})]_2$ may be used as the ruthenium (Ru) catalyst.

The rhodium (Rh) catalyst may be used in an amount of 0.01 to 0.05 equivalents based on the phosphinic derivative represented by Chemical Formula 5, and preferably, may be used in an amount of 0.02 equivalents. In addition, the ruthenium (Ru) catalyst may be used in an amount of 0.02 to 0.2 equivalents based on the phosphinic derivative represented by Chemical Formula 5, and preferably, may be used in an amount of 0.1 to 0.2 equivalents. Only in the case where the rhodium (Rh) catalyst or the ruthenium (Ru) catalyst is used in the above-described range, the phosphinine oxide derivative with a high yield may be prepared and when the amount of the catalyst is out of the range, yield and economical efficiency may be deteriorated.

The oxidant may be one or a mixture of two or more selected from the group consisting of silver (I) oxide (AgO), silver (II) oxide ($Ag_2O$), silver acetate (AgOAc), silver (II) carbonate ($Ag_2CO_3$), silver hexafluoroantimonate (V) ($AgSbF_6$), silver triflate (AgOTf), copper (II) acetate monohydrate ($Cu(OAc)_2.H_2O$), copper (II) oxide (CuO), copper (I) oxide ($Cu_2O$), copper (I) acetate (CuOAc), copper (II) acetate ($Cu(OAc)_2$), copper triflate ($Cu(OTf)_2$), sodium persulfate ($Na_2S_2O_8$), potassium persulfate ($K_2S_2O_8$), copper (II) bromide ($CuBr_2$), 2,2,6,6-tetramethyl-1-piperidinyloxy (free radical) (TEMPO), iodosobenzene diacetate (PhI(OAc)$_2$), ammonium persulfate (($NH_4)_2S_2O_8$), oxygen, cesium pivalate, p-benzoquinone and tert-butylhydroperoxide (TBHP). More preferably, as the oxidant, AgOAc, $Ag_2CO_3$, or a mixture thereof may be the most preferred in view of reactivity and yield.

The oxidant may be used in an amount of 0.2 to 4.0 equivalents based on the phosphinic derivative represented by Chemical Formula 5, and more preferably, one oxidant may be used in an amount of 2.0 equivalents or two oxidants may be used in an amount of 1 equivalent or 2 equivalents each.

The alkyne derivative represented by Chemical Formula 6 may be used in an amount of 1.0 to 3.0 equivalents based on the phosphinic derivative represented by Chemical Formula 5, and 1.5 to 2.5 equivalents may be the most preferred in view of reactivity and yield.

The preparation method may further contain: an additive or a base.

The additive may be one or a mixture of two or more selected from the group consisting of LiOAc, $Li_2CO_3$, NaOAc, $Na_2CO_3$, $Na_2HPO_4$, $NaHCO_3$, KOAc, $K_2CO_3$, $K_3PO_4$, $K_2HPO_4$, $KH_2PO_4$, $KPF_6$, CsF, CsOAc and CsOPiv, and preferably, $KPF_6$. The additive may be used in an amount of 0.2 to 1.0 equivalents based on the phosphinic derivative represented by Chemical Formula 5, and preferably, may be used in an amount of 0.2 to 0.4 equivalents.

The base may be one or a mixture of two or more selected from the group consisting of triethylamine, tetrabutylammonium chloride, lithium chloride, potassium t-butoxide, silver acetate, cesium fluoride, cesium acetate, cesium pivalate, sodium acetate, lithium acetate, potassium acetate, cesium carbonate, sodium carbonate, lithium carbonate, potassium carbonate, potassium phosphate monobasic, potassium phosphate dibasic, and potassium phosphate tribasic, and preferably, potassiumphosphate monobasic. The base may be used in an amount of 0.5 to 2.0 equivalents based on the phosphinic derivative represented by Chemical Formula 5, and preferably, may be used in an amount of 1.0 equivalent.

A solvent used in the preparation method of the phosphinine oxide derivative according to the present invention may be any general organic solvent; however, 1,4-dioxane, dichloroethane (DCE), toluene, trifluoromethyl benzene, xylene, acetonitrile (MeCN), nitromethane, tetrahydrofuran (THF), N,N-dimethylformamide (DMF), acetamide, mesitylene, chlorobenzene, N,N-dimethylacetamide (DMA), tert-amyl alcohol, tert-butanol (t-BuOH) or mixed solvents thereof may be preferably used, and more preferably, tert-butyl alcohol or N,N-dimethylformamide.

A reaction temperature in the preparation method of the phosphinine oxide derivative according to the present invention may be any general temperature used in the organic synthesis; however, may be varied depending on a reaction time, a reaction material, and an amount of a starting material. In order to prevent deterioration of a reaction yield due to an extremely long reaction time or by-products, an annulation reaction may be performed at a temperature range of room temperature to 130° C., and preferably, 90 to 130° C. More preferably, when X is O in the phosphinine derivative represented by Chemical Formula 5, the annulation reaction may be performed at 90 to 120° C., and when X is NR' in the phosphinine derivative represented by Chemical Formula 5, the annulation reaction may be performed at 110 to 130° C.

The reaction time may be varied depending on a reaction material, an amount of the reaction material, a kind of a solvent, and an amount of the solvent, and after complete consumption of the phosphinine derivative represented by Chemical Formula 5 which is the starting material is confirmed by TLC, and the like, the reaction is allowed to be completed. When the reaction is completed, the solvent is distilled under reduced pressure, and a target material may be separated and purified by general methods such as column chromatography, and the like.

DETAILED DESCRIPTION OF EMBODIMENTS

Hereinafter, the present invention will be described in detail with reference to examples. These examples are only for exemplifying the present invention, and it will be obvious to those skilled in the art that the scope of the present invention is not construed to be limited to these examples.

EXAMPLE 1

Preparation of 3,4-Diphenyl-1-ethoxybenz[c-1,2]oxaphinine 1-oxide

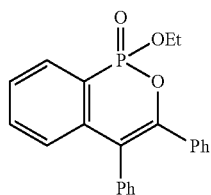 [SMILES: CCOP1(=O)OC(c2ccccc2)=C(c2ccccc2)c2ccccc21]

Phenylphosphonic monoethyl ester (28.0 mg, 0.15 mmol), diphenylacetylene (40.0 mg, 0.23 mmol), dichloro(pentamethylcyclopentadienyl)rhodium(III)dimer ([Rh(C$_5$Me$_5$)Cl$_2$]$_2$) (1.9 mg, 0.003 mmol), silver carbonate (Ag$_2$CO$_3$)(41.0 mg, 0.15 mmol), silver acetate (AgOAc) (26.0 mg, 0.15 mmol), tert-butanol (t-BuOH)(1.0 mL) were added dropwise to a V-vial and stirred at 90° C. for 16 hours. Whether or not the reaction proceeds was confirmed by TLC, and extraction with dichloromethane (DCM) and filtration through celite were performed to complete the reaction. The extracted organic layer was dried over anhydrous magnesium sulfate and filtered. A solvent was removed and then separation was performed by column chromatography to obtain 3,4-diphenyl-1-ethoxybenz[c-1,2]oxaphinine 1-oxide (49.0 mg, 90%) as a target compound.

$^1$H NMR (400 MHz, CDCl$_3$) δ 7.94-7.92 (m, 1H), 7.50-7.40 (m, 2H), 7.39-7.33 (m, 3H), 7.25-7.11 (m, 7H), 6.98-6.93 (m, 1H), 4.33-4.19 (m, 2H), 1.32 (t, J=7.08 Hz, 3H)

EXAMPLE 2

Preparation of 3,4-Bis(3-chlorophenyl)-1-ethoxybenz[c-1,2]oxaphinine 1-oxide

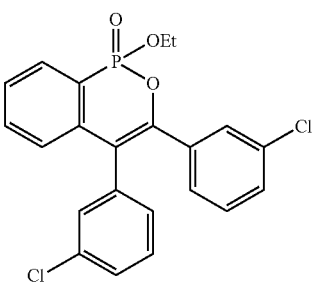 [SMILES: CCOP1(=O)OC(c2cccc(Cl)c2)=C(c2cccc(Cl)c2)c2ccccc21]

3,4-Bis(3-chlorophenyl)-1-ethoxybenz[c-1,2]oxaphinine 1-oxide (45 mg, 70%) as a target compound was obtained under the condition of 90° C. for 30 hours, by the same reaction as the Example 1 above, except for using (3-chlorophenyl)ethyne (55.0 mg, 0.23 mmol) instead of using diphenylacetylene of the Example 1 above.

$^1$H NMR (400 MHz, CDCl$_3$) δ 7.99-7.93 (m, 1H), 7.54-7.45 (m, 2H), 7.39-7.30 (m, 3H), 7.26-7.18 (m, 2H), 7.11-7.02 (m, 3H), 6.95-6.91 (m, 1H), 4.35-4.21 (m, 2H), 1.34 (t, J=7.06 Hz, 3H)

EXAMPLE 3

Preparation of 3,4-Bis(4-methylphenyl)-1-ethoxybenz-[c-1,2]oxaphinine 1-oxide

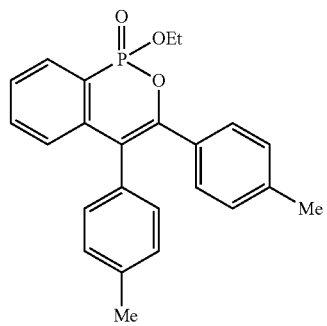 [SMILES: CCOP1(=O)OC(c2ccc(C)cc2)=C(c2ccc(C)cc2)c2ccccc21]

3,4-Bis(4-methylphenyl)-1-ethoxybenz-[c-1,2]oxaphinine 1-oxide (50.0 mg, 85%) as a target compound was obtained under the condition of 90° C. for 16 hours, by the same reaction as the Example 1 above, except for using 1,2-bis(4-methylphenyl)ethyne (46.0 mg, 0.23 mmol) instead of using diphenylacetylene of the Example 1 above.

$^1$H NMR (400 MHz, CDCl$_3$) δ 7.96-7.90 (m, 1H), 7.46-7.37 (m, 2H), 7.25-7.07 (m, 6H), 6.97-6.94 (m, 3H), 4.30-4.16 (m, 2H), 2.38 (s, 3H), 2.26 (s, 3H), 1.30 (t, J=7.06 Hz, 3H)

EXAMPLE 4

Preparation of 3,4-Bis(3-methylphenyl)-1-ethoxybenz[c-1,2]oxaphinine 1-oxide

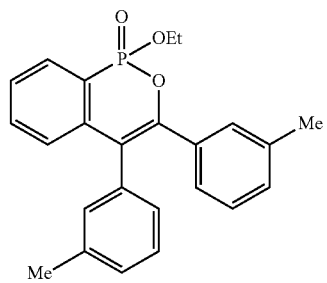 [SMILES: CCOP1(=O)OC(c2cccc(C)c2)=C(c2cccc(C)c2)c2ccccc21]

3,4-Bis(3-methylphenyl)-1-ethoxybenz-[c-1,2]oxaphinine 1-oxide (47.0 mg, 80%) as a target compound was obtained under the condition of 90° C. for 16 hours, by the same reaction as the Example 1 above, except for using 1,2-bis(3-methylphenyl)ethyne (46.0 mg, 0.23 mmol) instead of using diphenylacetylene of the Example 1 above.

$^1$H NMR (400 MHz, CDCl$_3$) δ 7.97-7.91 (m, 1H), 7.49-7.39 (m, 2H), 7.26-7.15 (m, 4H), 7.02-6.94 (m, 5H), 4.30-4.17 (m, 2H), 2.31 (s, 3H), 2.20 (s, 3H), 1.31 (t, J=7.06 Hz, 3H)

EXAMPLE 5

Preparation of 3,4-Bis(4-methoxyphenyl)-1-ethoxybenz[c-1,2]oxaphosphinine 1-oxide

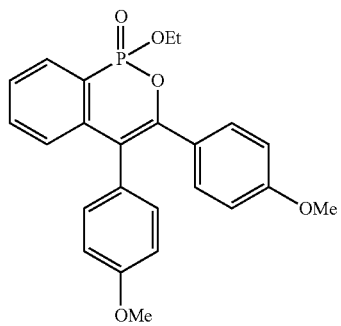 [SMILES: CCOP1(=O)OC(c2ccc(OC)cc2)=C(c2ccc(OC)cc2)c2ccccc21]

3,4-Bis(4-methoxyphenyl)-1-ethoxybenz[c-1,2]oxaphosphinine 1-oxide (57.0 mg, 90%) as a target compound was obtained under the condition of 90° C. for 12 hours, by the same reaction as the Example 1 above, except for using 1,2-bis(4-methoxyphenyl)ethyne (54.0 mg, 0.23 mmol) instead of using diphenylacetylene of the Example 1 above.

$^1$H NMR (400 MHz, CDCl$_3$) δ 7.95-7.89 (m, 1H), 7.48-7.43 (m, 1H), 7.41-7.37 (m, 1H), 7.19 (dt, J=9.17 Hz, 2.56 Hz, 2H), 7.14-7.10 (m, 2H), 7.00-6.96 (m, 1H), 6.93-6.89 (m, 2H), 7.19 (dt, J=9.20 Hz, 2.52 Hz, 2H), 4.30-4.15 (m, 2H), 3.84 (s, 3H), 3.75 (s, 3H), 1.31 (t, J=4.82 Hz, 3H)

EXAMPLE 6

Preparation of 3-(4-Methoxyphenyl)-4-(4-methylphenyl)-1-ethoxybenz[c-1,2]oxaphosphinine 1-oxide and 4-(4-Methoxyphenyl)-3-(4-methylphenyl)-1-ethoxybenz[c-1,2]oxaphosphinine 1-oxide

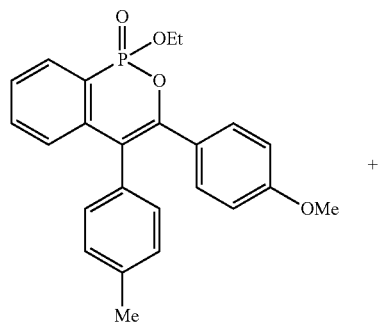

(3-(4-methoxyphenyl)-4-(4-methylphenyl)-1-ethoxybenz[c-1,2]oxaphosphinine 1-oxide and 4-(4-methoxyphenyl)-3-(4-methylphenyl)-1-ethoxybenz[c-1,2]oxaphosphinine 1-oxide (56.0 mg, 92%) as a target product were obtained at an isomer ratio of 1:1 under the condition of 90° C. for 16 hours, by the same reaction as the Example 1 above, except for using 1-methoxy-4-(p-tolylethynyl)benzene (50.0 mg, 0.23 mmol) instead of using diphenylacetylene of the Example 1 above.

$^1$H NMR (400 MHz, CDCl$_3$) data for the major isomer; δ 7.96-7.89 (m, 1H), 7.48-7.36 (m, 2H), 7.21-7.08 (m, 5H), 7.00-6.89 (m, 3H), 6.69-6.65 (m, 1H), 4.30-4.16 (m, 2H), 3.83 (s, 3H), 2.39 (s, 3H), 1.31 (t, J=7.08 Hz, 3H); data for the minor isomer; δ 7.96-7.89 (m, 1H), 7.48-7.36 (m, 2H), 7.21-7.08 (m, 5H), 7.00-6.89 (m, 3H), 6.69-6.65 (m, 1H), 4.30-4.16 (m, 2H), 3.74 (s, 3H), 2.26 (s, 3H), 1.30 (t, J=7.08 Hz, 3H)

EXAMPLE 7

Preparation of 3-Phenyl-4-methyl-1-ethoxybenz[c-1,2]oxaphosphinine 1-oxide and 4-Phenyl-3-methyl-1-ethoxybenz[c-1,2]oxaphosphinine 1-oxide

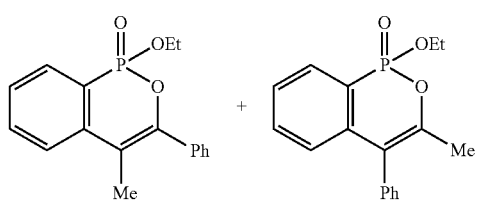

3-phenyl-4-methyl-1-ethoxybenz[c-1,2]oxaphosphinine 1-oxide and 4-phenyl-3-methyl-1-ethoxybenz[c-1,2]oxaphosphinine 1-oxide (41.0 mg, 91%) as a target product were obtained at an isomer ratio of 10.7:1 under the condition of 90° C. for 4 hours, by the same reaction as the Example 1 above, except for using 1-propynylbenzene (26.0 mg, 0.23 mmol) instead of using diphenylacetylene of the Example 1 above.

$^1$H NMR (400 MHz, CDCl$_3$) data for the major isomer; δ 7.94-7.88 (m, 1H), 7.69-7.65 (m, 1H), 7.56-7.52 (m, 3H), 7.49-7.39 (m, 4H), 4.28-4.19 (m, 2H), 2.21 (d, J=0.92, 3H), 1.33 (t, J=7.08 Hz, 3H); data for the minor isomer; δ 7.89-7.88 (m, 1H), 7.49-7.39 (m, 3H), 7.39-7.32 (m, 2H), 7.23-7.22 (m, 2H), 6.76-6.73 (m, 1H), 4.30-4.17 (m, 2H), 1.96 (s, 3H), 1.38 (t, J=7.08 Hz, 3H)

EXAMPLE 8

Preparation of 3-Phenyl-4-butyl-1-ethoxybenz[c-1,2]oxaphosphinine 1-oxide and 4-Phenyl-3-butyl-1-ethoxybenz[c-1,2]oxaphosphinine 1-oxide

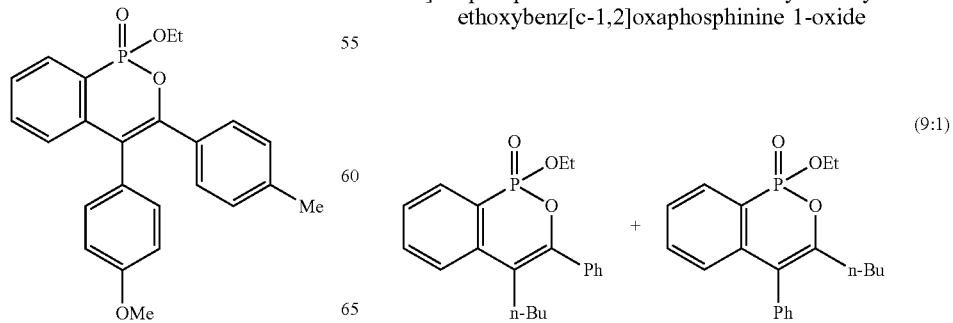

3-phenyl-4-butyl-1-ethoxybenz[c-1,2]oxaphosphinine 1-oxide and 4-phenyl-3-butyl-1-ethoxybenz[c-1,2]oxaphosphinine 1-oxide (41.0 mg, 80%) as a target product were obtained at an isomer ratio of 9:1 under the condition of 90° C. for 10 hours, by the same reaction as the Example 1 above, except for using 1-hexynyl benzene (36.0 mg, 0.23 mmol) instead of using diphenylacetylene of the Example 1 above.

$^{1}$H NMR (400 MHz, CDCl$_{3}$) data for the major isomer; δ 7.95-7.89 (m, 1H), 7.68-7.64 (m, 1H), 7.55-7.53 (m, 1H), 7.51-7.40 (m, 6H), 4.24-4.17 (m, 2H), 2.67-2.53 (m, 2H), 1.58-1.43 (m, 2H), 1.31 (t, J=7.06 Hz, 3H), 1.28-1.21 (m, 2H), 0.86 (t, J=7.32 Hz, 3H); data for the minor isomer; δ 7.90-7.84 (m, 1H), 7.55-7.53 (m, 3H), 7.39-7.32 (m, 2H), 7.24-7.19 (m, 2H), 6.74-6.70 (m, 1H), 4.30-4.18 (m, 2H), 2.22-2.16 (m, 2H), 1.58-1.43 (m, 2H), 1.37 (t, J=7.08 Hz, 3H), 1.29-1.21 (m, 2H), 0.86 (t, J=7.32, 3H)

EXAMPLE 9

Preparation of 3,4-Diethyl-1-ethoxybenz[c-1,2]oxaphosphinine 1-oxide

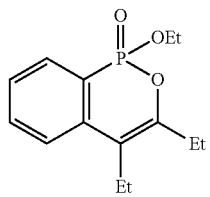 [SMILES: CCOP1(=O)OC(CC)=C(CC)c2ccccc21]

3,4-diethyl-1-ethoxybenz[c-1,2]oxaphosphinine 1-oxide (35.0 mg, 88%) as a target compound was obtained under the condition of 90° C. for 9 hours, by the same reaction as the Example 1 above, except for using 3-hexyne (18.0 mg, 0.23 mmol) instead of using diphenylacetylene of the Example 1 above.

$^{1}$H NMR (400 MHz, CDCl$_{3}$) δ 7.89-7.82 (m, 1H), 7.63-7.58 (m, 1H), 7.45 (t, J=7.26 Hz, 1H), 7.40-7.35 (m, 1H), 4.23-4.09 (m, 2H), 2.60-2.42 (m, 4H), 1.31 (t, J=7.25 Hz, 3H), 1.23 (t, J=7.50 Hz, 3H), 1.16 (t, J=7.25 Hz, 3H)

EXAMPLE 10

Preparation of 3,4-Dibutyl-1-ethoxybenz[c-1,2]oxaphosphinine 1-oxide

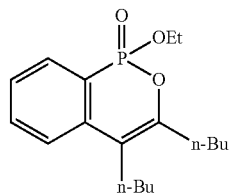

3,4-dibutyl-1-ethoxybenz[c-1,2]oxaphosphinine 1-oxide (42.0 mg, 87%) as a target compound was obtained under the condition of 90° C. for 16 hours, by the same reaction as the Example 1 above, except for using 5-decyne (31.0 mg, 0.23 mmol) instead of using diphenylacetylene of the Example 1 above.

$^{1}$H NMR (400 MHz, CDCl$_{3}$) δ 7.87-7.82 (m, 1H), 7.62-7.57 (m, 1H), 7.44-7.35 (m, 2H), 4.22-4.08 (m, 2H), 2.58-2.41 (m, 2H), 1.69-1.61 (m, 2H), 1.53-1.36 (m, 6H), 1.30 (t, J=7.06 Hz, 3H), 0.95 (dt, J=7.25 Hz, 1.62 Hz, 6H)

EXAMPLE 11

Preparation of 3-Propyl-4-methyl-1-ethoxybenz[c-1,2]oxaphosphinine 1-oxide and 4-Propyl-3-methyl-1-ethoxybenz[c-1,2]oxaphosphinine 1-oxide

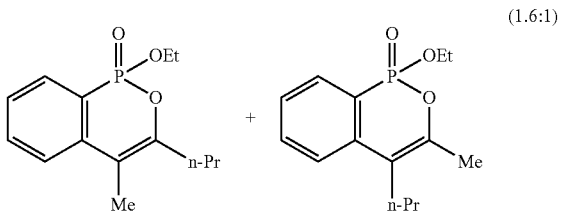

(1.6:1)

3-propyl-4-methyl-1-ethoxybenz[c-1,2]oxaphosphinine 1-oxide and 4-propyl-3-methyl-1-ethoxybenz[c-1,2]oxaphosphinine 1-oxide (33.0 mg, 83%) as a target product were obtained at an isomer ratio of 1.6:1 under the condition of 90° C. for 12 hours, by the same reaction as the Example 1 above, except for using 2-hexyne (18.0 mg, 0.23 mmol) instead of using diphenylacetylene of the Example 1 above.

$^{1}$H NMR (400 MHz, CDCl$_{3}$) data for the major isomer; δ 7.87-7.81 (m, 1H), 7.63-7.57 (m, 1H), 7.43-7.35 (m, 2H), 4.22-4.12 (m, 2H), 2.58-2.41 (m, 2H), 2.19 (s, 3H), 1.62-1.47 (m, 2H), 1.32 (t, J=7.06 Hz, 3H), 0.98 (t, J=7.36 Hz, 3H); data for the minor isomer; δ 7.87-7.81 (m, 1H), 7.63-7.57 (m, 1H), 7.43-7.35 (m, 2H), 4.22-4.12 (m, 2H), 2.58-2.41 (m, 2H), 2.16 (s, 3H), 1.74-1.64 (m, 2H), 1.32 (t, J=7.06 Hz, 3H), 0.98 (t, J=7.04 Hz, 3H)

EXAMPLE 12

Preparation of 3,4-Diphenyl-1-ethoxy-6-fluoro-benz[c-1,2]oxaphosphinine 1-oxide

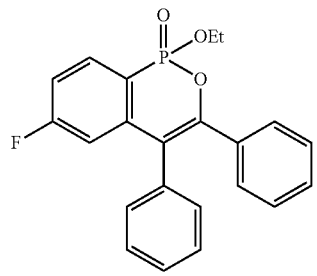 [SMILES: CCOP1(=O)OC(c2ccccc2)=C(c2ccccc2)c2cc(F)ccc21]

3,4-diphenyl-1-ethoxy-6-fluoro-benz[c-1,2]oxaphosphinine 1-oxide (47.0 mg, 82%) as a target product was obtained under the condition of 90° C. for 16 hours, by the same reaction as the Example 1 above, except for using 4-fluorophenylphosphonic monoethyl ester (31.0 mg, 0.15 mmol) instead of using phenylphosphonic monoethyl ester of the Example 1 above, and using 2-hexyne (18.0 mg, 0.23 mmol) instead of using diphenylacetylene of the Example 1 above.

¹H NMR (400 MHz, CDCl₃) δ 7.98-7.91 (m, 1H), 7.39-7.35 (m, 3H), 7.26-7.10 (m, 8H), 6.67-6.62 (m, 1H), 4.33-4.19 (m, 2H), 1.32 (t, J=7.06 Hz, 3H)

EXAMPLE 13

Preparation of 3-Phenyl-4-methyl-1-ethoxy-6-fluoro-benz[c-1,2]oxaphosphinine 1-oxide and 4-Phenyl-3-methyl-1-ethoxy-6-fluoro-benz[c-1,2]oxaphosphinine 1-oxide

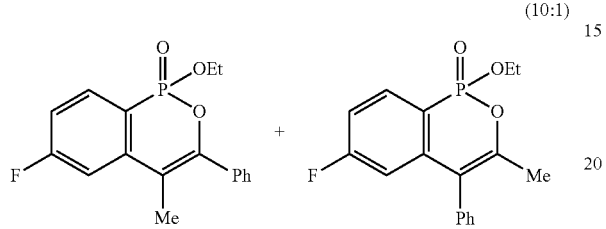

3-Phenyl-4-methyl-1-ethoxy-6-fluoro-benz[c-1,2]oxaphosphinine 1-oxide and 4-phenyl-3-methyl-1-ethoxy-6-fluoro-benz[c-1,2]oxaphosphinine 1-oxide (40.0 mg, 84%) as a target product were obtained at an isomer ratio of 10:1 under the condition of 90° C. for 5 hours, by the same reaction as the Example 1 above, except for using 4-fluorophenylphosphonic monoethyl ester (31.0 mg, 0.15 mmol) instead of using phenylphosphonic monoethyl ester of the Example 1 above, and using 1-propynylbenzene (26.0 mg, 0.23 mmol) instead of using diphenylacetylene of the Example 1 above.

¹H NMR (400 MHz, CDCl₃) data for the major isomer; δ 7.95-7.86 (m, 1H), 7.56-7.39 (m, 5H), 7.24-7.14 (m, 2H), 4.31-4.19 (m, 2H), 2.18 (d, J=0.80 Hz, 3H), 1.34 (t, J=7.08 Hz, 3H); data for the minor isomer; δ 7.90-7.83 (m, 1H), 7.56-7.39 (m, 3H), 7.24-7.14 (m, 2H), 7.08-7.02 (m, 1H), 6.46-6.41 (m, 1H), 4.31-4.19 (m, 2H), 1.97 (s, 3H), 1.39 (t, J=7.08 Hz, 3H)

EXAMPLE 14

Preparation of 3,4-Diethyl-1-ethoxy-6-fluoro-benz[c-1,2]oxaphosphinine 1-oxide

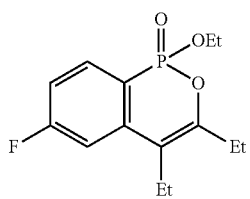 [SMILES: CCOP1(=O)OC(CC)=C(CC)c2cc(F)ccc21]

3,4-Diethyl-1-ethoxy-6-fluoro-benz[c-1,2]oxaphosphinine 1-oxide (34.0 mg, 80%) as a target product was obtained under the condition of 90° C. for 16 hours, by the same reaction as the Example 1 above, except for using 4-fluorophenylphosphonic monoethyl ester (31.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

¹H NMR (400 MHz, CDCl₃) δ 7.88-7.81 (m, 1H), 7.14-7.05 (m, 2H), 4.24-4.12 (m, 2H), 1.32 (t, J=4.92 Hz, 3H), 1.23 (t, J=7.50 Hz, 3H), 1.16 (t, J=7.54 Hz, 3H)

EXAMPLE 15

Preparation of 3,4-Bis(4-methoxyphenyl)-1-ethoxy-6-iodobenz[c-1,2]oxaphosphinine 1-oxide

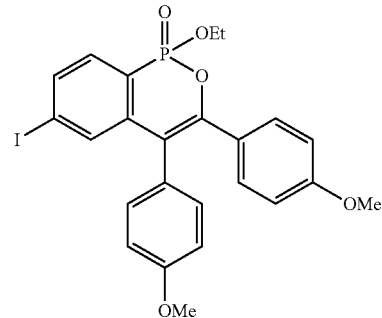 [SMILES: CCOP1(=O)OC(c2ccc(OC)cc2)=C(c2ccc(OC)cc2)c2cc(I)ccc21]

3,4-bis(4-methoxyphenyl)-1-ethoxy-6-iodobenz[c-1,2]oxaphosphinine 1-oxide (71.0 mg, 86%) as a target product was obtained under the condition of 90° C. for 16 hours, by the same reaction as the Example 1 above, except for using 4-iodophenylphosphonic monoethyl ester (47.0 mg, 0.15 mmol) instead of using phenylphosphonic monoethyl ester of the Example 1 above, and using 1,2-bis(4-methylphenyl)ethyne (54.0 mg, 0.23 mmol) instead of using diphenylacetylene of the Example 1 above.

¹H NMR (400 MHz, CDCl₃) δ 7.76-7.73 (m, 1H), 7.60 (dd, J=14.60 Hz, 7.92 Hz, 1H), 7.32 (dd, J=5.52 Hz, 1.40 Hz, 1H), 7.18-7.14 (m, 2H), 7.10-6.91 (m, 4H), 6.68 (dt, J=9.18 Hz, 2.54 Hz, 2H), 4.30-4.16 (m, 2H), 3.86 (s, 3H), 3.75 (s, 3H), 1.30 (t, J=7.08 Hz, 3H)

EXAMPLE 16

Preparation of 3,4-Diethyl-1-ethoxy-6-iodobenz[c-1,2]oxaphosphinine 1-oxide

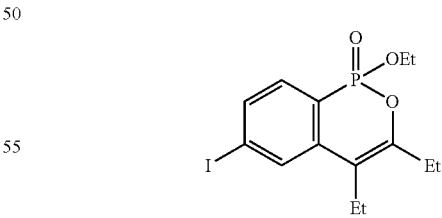

3,4-diethyl-1-ethoxy-6-iodobenz[c-1,2]oxaphosphinine 1-oxide (48.0 mg, 82%) as a target product was obtained under the condition of 90° C. for 10 hours, by the same reaction as the Example 1 above, except for using 4-iodophenylphosphonic monoethyl ester (47.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

¹H NMR (400 MHz, CDCl₃) δ 7.79-7.72 (m, 2H), 7.54 (dd, J=14.60 Hz, 7.92 Hz, 1H), 4.23-4.09 (m, 2H), 2.58-2.41 (m, 4H), 1.31 (t, J=7.08 Hz, 3H), 1.22 (t, J=7.50 Hz, 3H), 1.15 (t, J=7.52 Hz, 3H)

EXAMPLE 17

Preparation of 3,4-Diphenyl-1-ethoxy-6-acetyl-benz[c-1,2]oxaphosphinine 1-oxide

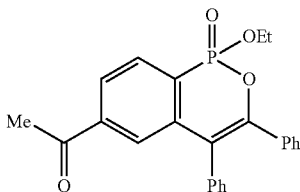 [SMILES: CCOP1(=O)OC(c2ccccc2)=C(c2ccccc2)c2cc(C(C)=O)ccc21]

3,4-diphenyl-1-ethoxy-6-acetyl-benz[c-1,2]oxaphosphinine 1-oxide (47.0 mg, 78%) as a target compound was obtained under the condition of 90° C. for 16 hours, by the same reaction as the Example 1 above, except for using 4-acetylphenylphosphonic monoethyl ester (34.0 mg, 0.15 mmol) instead of using phenylphosphonic monoethyl ester of the Example 1 above.

¹H NMR (400 MHz, CDCl₃) δ 8.08-8.02 (m, 1H), 7.98-7.95 (m, 1H), 7.53-7.51 (m, 1H), 7.39-7.37 (m, 3H), 7.26-7.13 (m, 7H), 4.36-4.22 (m, 2H), 2.44 (s, 3H), 1.33 (t, J=7.08 Hz, 3H)

EXAMPLE 18

Preparation of 3,4-Diethyl-1-ethoxy-6-acetyl-benz[c-1,2]oxaphosphinine 1-oxide

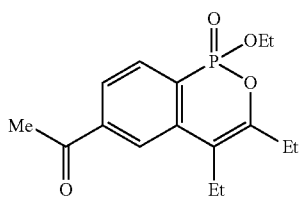 [SMILES: CCOP1(=O)OC(CC)=C(CC)c2cc(C(C)=O)ccc21]

3,4-diethyl-1-ethoxy-6-acetyl-benz[c-1,2]oxaphosphinine 1-oxide (33.0 mg, 72%) as a target product was obtained under the condition of 90° C. for 10 hours, by the same reaction as the Example 1 above, except for using 4-acetylphenylphosphonic monoethyl ester (34.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

¹H NMR (400 MHz, CDCl₃) δ 8.03-7.89 (m, 3H), 4.24-4.15 (m, 2H), 2.66 (s, 3H), 2.63-2.48 (m, 4H), 1.32 (t, J=7.06 Hz, 3H), 1.24 (t, J=7.48 Hz, 3H), 1.18 (t, J=7.52 Hz, 3H)

EXAMPLE 19

Preparation of 3,4-Bis(4-methylphenyl)-1-ethoxy-8-methylbenz[c-1,2]oxaphosphinine 1-oxide

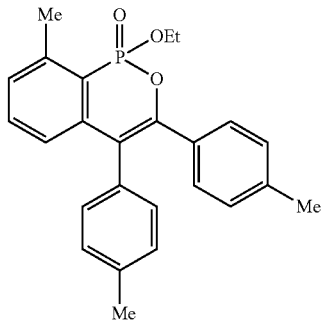 [SMILES: CCOP1(=O)OC(c2ccc(C)cc2)=C(c2ccc(C)cc2)c2cccc(C)c21]

3,4-bis(4-methylphenyl)-1-ethoxy-8-methylbenz[c-1,2]oxaphosphinine 1-oxide (56.0 mg, 92%) as a target product was obtained under the condition of 90° C. for 16 hours, by the same reaction as the Example 1 above, except for using 2-methylphenylphosphonic monoethyl ester (30.0 mg, 0.15 mmol) instead of using phenylphosphonic monoethyl ester of the Example 1 above, and using 1,2-bis(4-methylphenyl)ethyne (46.0 mg, 0.23 mmol) instead of using diphenylacetylene of the Example 1 above.

¹H NMR (400 MHz, CDCl₃) δ 7.32-7.26 (m, 1H), 7.18-7.11 (m, 5H), 7.07-7.05 (m, 2H), 6.95 (d, J=8.04 Hz, 2H), 6.79-6.76 (m, 1H), 4.31-4.14 (m, 2H), 2.75 (d, J=1.04 Hz, 3H), 2.37 (s, 3H), 2.25 (s, 3H), 1.33 (t, J=7.08 Hz, 3H)

EXAMPLE 20

Preparation of 3-Phenyl-4-methyl-1-ethoxy-8-methylbenz[c-1,2]oxaphosphinine 1-oxide and 4-Phenyl-3-methyl-1-ethoxy-8-methylbenz[c-1,2]oxaphosphinine 1-oxide

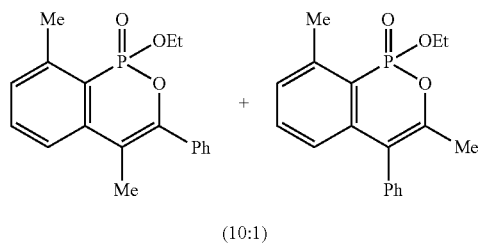 [SMILES: CCOP1(=O)OC(c2ccccc2)=C(C)c2cccc(C)c21 ; CCOP1(=O)OC(C)=C(c2ccccc2)c2cccc(C)c21]

(10:1)

3-phenyl-4-methyl-1-ethoxy-8-methylbenz[c-1,2]oxaphosphinine 1-oxide and 4-phenyl-3-methyl-1-ethoxy-8-methylbenz[c-1,2]oxaphosphinine 1-oxide (45.0 mg, 95%) as a target product were obtained at an isomer ratio of 10:1 under the condition of 90° C. for 6 hours, by the same reaction as the Example 1 above, except for using 2-methylphenylphosphonic monoethyl ester (30.0 mg, 0.15 mmol) instead of using phenylphosphonic monoethyl ester of the Example 1 above, and using 1-propynylbenzene (26.0 mg, 0.23 mmol) instead of using diphenylacetylene of the Example 1 above.

¹H NMR (400 MHz, CDCl₃) data for the major isomer; δ 7.55-7.51 (m, 3H), 7.45-7.36 (m, 4H), 7.28-7.22 (m, 1H), 4.29-4.15 (m, 2H), 2.73 (d, J=1.60 Hz, 3H), 2.18 (d, J=0.60 Hz, 3H), 1.34 (t, J=7.08 Hz, 3H); data for the minor isomer; δ 7.45-7.36 (m, 3H), 7.28-7.22 (m, 1H), 7.20-7.18 (m, 2H), 7.14-7.11 (m, 1H), 6.57-6.54 (m, 2H), 4.29-4.15 (m, 2H), 2.71 (d, J=1.52 Hz, 3H), 1.93 (s, 3H), 1.40 (t, J=7.08 Hz, 3H)

EXAMPLE 21

Preparation of 3,4-Dibutyl-1-ethoxy-8-methylbenz[c-1,2]oxaphosphinine 1-oxide

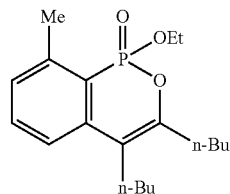

3,4-dibutyl-1-ethoxy-8-methylbenz[c-1,2]oxaphosphinine 1-oxide (48.0 mg, 95%) as a target product was obtained under the condition of 90° C. for 12 hours, by the same reaction as the Example 1 above, except for using 2-methylphenylphosphonic monoethyl ester (30.0 mg, 0.15 mmol) instead of using phenylphosphonic monoethyl ester of the Example 1 above, and using 5-decyne (31.0 mg, 0.23 mmol) instead of using diphenylacetylene of the Example 1 above.

$^1$H NMR (400 MHz, CDCl$_3$) δ 7.48-7.44 (m, 1H), 7.27-7.24 (m, 1H), 7.16-7.13 (m, 1H), 4.16-4.04 (m, 2H), 2.68 (d, J=1.06 Hz, 3H), 2.53-2.45 (m, 4H), 1.69-1.61 (m, 2H), 1.51-1.36 (m, 6H), 1.33 (t, J=7.06 Hz, 3H), 0.95 (dt, J=7.22 Hz, 1.92 Hz, 6H)

EXAMPLE 22

Preparation of 3,4-Bis(4-methoxyphenyl)-1-ethoxy-7-methylbenz[c-1,2]oxaphosphinine 1-oxide

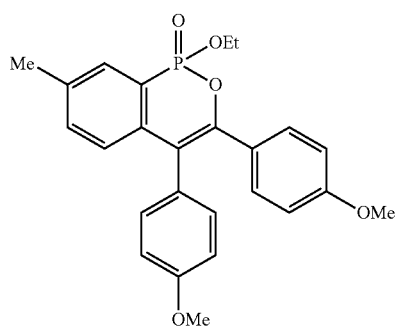 [SMILES: CCOP1(=O)OC(c2ccc(OC)cc2)=C(c2ccc(OC)cc2)c2ccc(C)cc21]

3,4-bis(4-methoxyphenyl)-1-ethoxy-7-methylbenz[c-1,2]oxaphosphinine 1-oxide (56.0 mg, 86%) as a target product was obtained under the condition of 90° C. for 16 hours, by the same reaction as the Example 1 above, except for using 3-methylphenylphosphonic monoethyl ester (30.0 mg, 0.15 mmol) instead of using phenylphosphonic monoethyl ester of the Example 1 above, and using 1,2-bis(4-methoxyphenyl)ethyne (54.0 mg, 0.23 mmol) instead of using diphenylacetylene of the Example 1 above.

$^1$H NMR (400 MHz, CDCl$_3$) δ 7.75-7.71 (m, 1H), 7.27-7.09 (m, 5H), 6.91-6.84 (m, 3H), 6.69-6.65 (m, 2H), 4.29-4.16 (m, 2H), 3.84 (s, 3H), 3.75 (s, 3H), 2.40 (s, 3H), 1.30 (t, J=7.08 Hz, 3H)

EXAMPLE 23

Preparation of 3-Phenyl-4-methyl-1-ethoxy-7-methylbenz[c-1,2]oxaphosphinine 1-oxide and 4-Phenyl-3-methyl-1-ethoxy-7-methylbenz[c-1,2]oxaphosphinine 1-oxide

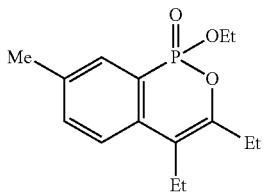 [SMILES: CCOP1(=O)OC(CC)=C(CC)c2ccc(C)cc21]

(8:8:1)

3-phenyl-4-methyl-1-ethoxy-7-methylbenz[c-1,2]oxaphosphinine 1-oxide and 4-phenyl-3-methyl-1-ethoxy-7-methylbenz[c-1,2]oxaphosphinine 1-oxide (40.0 mg, 85%) as a target product were obtained at an isomer ratio of 8.8:1 under the condition of 90° C. for 10 hours, by the same reaction as the Example 1 above, except for using 3-methylphenylphosphonic monoethyl ester (30.0 mg, 0.15 mmol) instead of using phenylphosphonic monoethyl ester of the Example 1 above, and using 1-propynylbenzene (26.0 mg, 0.23 mmol) instead of using diphenylacetylene of the Example 1 above.

$^1$H NMR (400 MHz, CDCl$_3$) data for the major isomer; δ 7.74-7.70 (m, 1H), 7.54-7.51 (m, 2H), 7.48-7.36 (m, 5H), 4.27-4.19 (m, 2H), 2.44 (s, 3H), 2.19 (d, J=0.80 Hz, 3H), 1.33 (t, J=7.08 Hz, 3H); data for the minor isomer; δ 7.71-7.66 (m, 1H), 7.41-7.36 (m, 3H), 7.22-7.20 (m, 3H), 6.66-6.62 (m, 1H), 4.29-4.18 (m, 2H), 2.37 (s, 3H), 1.95 (s, 3H), 1.39 (t, J=7.08 Hz, 3H)

EXAMPLE 24

Preparation of 3,4-Diethyl-1-ethoxy-7-methylbenz[c-1,2]oxaphosphinine 1-oxide 3,4-diethyl-1-ethoxy-7-methylbenz[c-1,2]oxaphosphinine 1-oxide (34.0 mg, 81%) as a target product was obtained under the condition of 90° C. for 14 hours, by the same reaction as the Example 1 above, except for using 3-methylphenylphosphonic monoethyl ester (30.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

$^1$H NMR (400 MHz, CDCl$_3$) δ 7.69-7.64 (m, 1H), 7.42-7.31 (m, 2H), 4.20-4.10 (m, 2H), 2.58-2.44 (m, 4H), 1.31 (t, J=7.08 Hz, 3H), 1.22 (t, J=7.50 Hz, 3H), 1.14 (t, J=7.52 Hz, 3H)

EXAMPLE 25

Preparation of 3,4-Diphenyl-1-ethoxy-6-methoxy-benz[c-1,2]oxaphosphinine 1-oxide

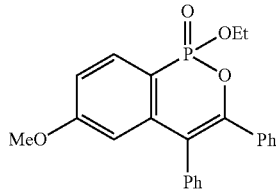 [SMILES: CCOP1(=O)OC(c2ccccc2)=C(c2ccccc2)c2cc(OC)ccc21]

3,4-diphenyl-1-ethoxy-6-methoxy-benz[c-1,2]oxaphosphinine 1-oxide (55.0 mg, 93%) as a target compound was obtained under the condition of 90° C. for 16 hours, by the same reaction as the Example 1 above, except for using 4-methoxyphenylphosphonic monoethyl ester (32.0 mg, 0.15 mmol) instead of using phenylphosphonic monoethyl ester of the Example 1 above.

$^1$H NMR (400 MHz, CDCl$_3$) δ 7.88 (dd, J=14.40 Hz, 8.40 Hz, 1H), 7.36-7.32 (m, 3H), 7.25-7.11 (m, 7H), 6.96 (td, J=8.42 Hz, 2.57 Hz, 1H), 6.45 (dd, J=5.40 Hz, 2.36 Hz, 1H), 4.25-4.15 (m, 2H), 3.68 (s, 3H), 1.30 (t, J=7.08 Hz, 3H)

EXAMPLE 26

Preparation of 3-Phenyl-4-methyl-1-ethoxy-6-methoxy-benz[c-1,2]oxaphosphinine 1-oxide and 4-Phenyl-3-methyl-1-ethoxy-6-methoxy-benz[c-1,2]oxaphosphinine 1-oxide

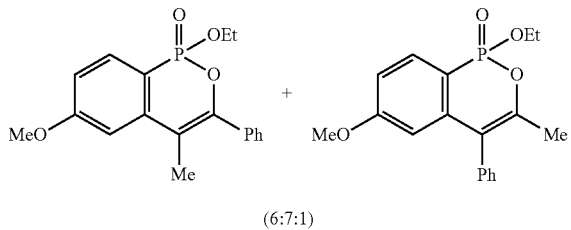 [SMILES: CCOP1(=O)OC(c2ccccc2)=C(C)c2cc(OC)ccc21 ; CCOP1(=O)OC(C)=C(c2ccccc2)c2cc(OC)ccc21]

(6.7:1)

3-phenyl-4-methyl-1-ethoxy-6-methoxy-benz[c-1,2]oxaphosphinine 1-oxide and 4-phenyl-3-methyl-1-ethoxy-6-methoxy-benz[c-1,2]oxaphosphinine 1-oxide (45.0 mg, 90%) as a target product were obtained at an isomer ratio of 6.7:1 under the condition of 90° C. for 6 hours, by the same reaction as the Example 1 above, except for using 4-methoxyphenylphosphonic monoethyl ester (32.0 mg, 0.15 mmol) instead of using phenylphosphonic monoethyl ester of the Example 1 above, and using 1-propynylbenzene (26.0 mg, 0.23 mmol) instead of using diphenylacetylene of the Example 1 above.

$^1$H NMR (400 MHz, CDCl$_3$) data for the major isomer; δ 7.85 (q, J=7.54 Hz, 1H), 7.54-7.51 (m, 2H), 7.45-7.39 (m, 3H), 7.03-6.97 (m, 2H), 4.27-4.13 (m, 2H), 2.18 (d, J=0.64 Hz, 3H), 1.32 (t, J=7.08 Hz, 3H); data for the minor isomer; δ 7.81 (q, J=7.57 Hz, 1H), 7.45-7.39 (m, 3H), 7.26-7.21 (m, 2H), 6.90-6.87 (m, 1H), 6.24-6.22 (m, 1H), 4.27-4.13 (m, 2H), 3.66 (s, 3H), 1.95 (s, 3H), 1.37 (t, J=7.06 Hz, 3H)

EXAMPLE 27

Preparation of 3,4-Diethyl-1-ethoxy-6-methoxy-benz[c-1,2]oxaphosphinine 1-oxide

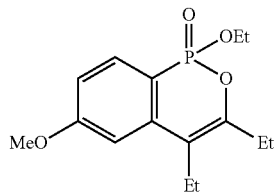 [SMILES: CCOP1(=O)OC(CC)=C(CC)c2cc(OC)ccc21]

3,4-diethyl-1-ethoxy-6-methoxy-benz[c-1,2]oxaphosphinine 1-oxide (40.0 mg, 89%) as a target product was obtained under the condition of 90° C. for 10 hours, by the same reaction as the Example 1 above, except for using 4-methoxyphenylphosphonic monoethyl ester (32.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

$^1$H NMR (400 MHz, CDCl$_3$) δ 7.79 (dd, J=14.56 Hz, 8.48 Hz, 1H), 6.94-6.90 (m, 2H), 4.20-4.05 (m, 2H), 3.87 (s, 3H), 2.57-2.42 (m, 4H), 1.30 (t, J=7.06 Hz, 3H), 1.22 (t, J=7.38 Hz, 3H), 1.16 (t, J=7.52 Hz, 3H)

EXAMPLE 28

Preparation of 3,4-Diethyl-7,8-(methylenedioxy)-1-ethoxy-benz[c-1,2]oxaphosphinine 1-oxide

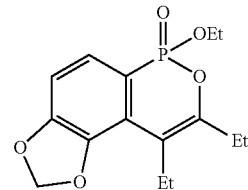 [SMILES: CCOP1(=O)OC(CC)=C(CC)c2c1ccc1c2OCO1]

3,4-diethyl-7,8-(methylene dioxy)-1-ethoxy-benz[c-1,2]oxaphosphinine 1-oxide (42.0 mg, 90%) as a target product was obtained under the condition of 90° C. for 16 hours, by the same reaction as the Example 1 above, except for using 1,3-benzodioxol-5-ylphosphonic monoethyl ester (35.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

$^1$H NMR (400 MHz, CDCl$_3$) δ 7.42 (q, J=7.72 Hz, 1H), 6.87 (q, J=3.69 Hz, 1H), 6.02 (dd, J=6.30 Hz, 1.38 Hz, 2H), 4.18-4.07 (m, 2H), 2.72-2.37 (m, 4H), 1.29 (t, J=7.06 Hz, 3H), 1.21 (t, J=7.48 Hz, 3H), 1.10 (t, J=7.36 Hz, 3H)

EXAMPLE 29

Preparation of 3,4-Bis(4-methylphenyl)-1-ethoxy-6-hydroxy-benz[c-1,2]oxaphosphinine 1-oxide

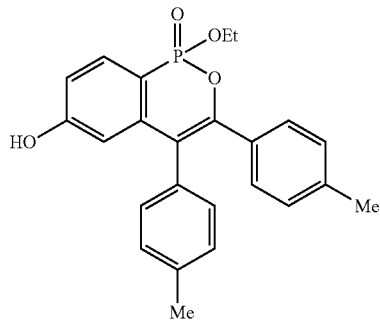 [SMILES: CCOP1(=O)OC(c2ccc(C)cc2)=C(c2ccc(C)cc2)c2cc(O)ccc21]

3,4-bis(4-methylphenyl)-1-ethoxy-6-hydroxy-benz[c-1,2]oxaphosphinine 1-oxide (46.0 mg, 76%) as a target product was obtained under the condition of 90° C. for 16 hours, by the same reaction as the Example 1 above, except for using 4-hydroxyphenylphosphonic monoethyl ester (30.0 mg, 0.15 mmol) instead of using phenylphosphonic monoethyl ester of the Example 1 above, and using 1,2-bis(4-methylphenyl)ethyne (46.0 mg, 0.23 mmol) instead of using diphenylacetylene of the Example 1 above.

$^1$H NMR (400 MHz, CDCl$_3$) δ 8.96 (s, 1H), 7.61 (dd, J=14.58 Hz, 8.30 Hz, 1H), 7.09-6.91 (m, 9H), 6.50-6.49 (m, 1H), 4.18-4.07 (m, 2H), 2.31 (s, 3H), 2.25 (s, 3H), 1.26 (t, J=7.08 Hz, 3H)

EXAMPLE 30

Preparation of 3,4-Dibutyl-1-ethoxy-6-hydroxy-benz[c-1,2]oxaphosphinine 1-oxide

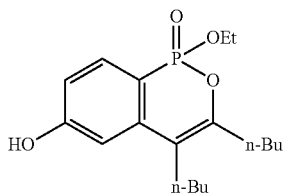

3,4-dibutyl-1-ethoxy-6-hydroxy-benz[c-1,2]oxaphosphinine 1-oxide (37.0 mg, 73%) as a target product was obtained under the condition of 90° C. for 16 hours, by the same reaction as the Example 1 above, except for using 4-hydroxyphenylphosphonic monoethyl ester (30.0 mg, 0.15 mmol) instead of using phenylphosphonic monoethyl ester of the Example 1 above, and using 5-decyne (31.0 mg, 0.23 mmol) instead of using diphenylacetylene of the Example 1 above.

$^1$H NMR (400 MHz, CDCl$_3$) δ 9.23 (s, 1H), 7.58 (dd, J=14.6 Hz, 8.28 Hz, 1H), 6.94 (dd, J=5.82 Hz, 1.98 Hz, 1H), 6.88 (dt, J=8.24 Hz, 2.32 Hz, 1H), 4.15-4.00 (m, 2H), 2.49-2.33 (m, 4H), 1.65-1.57 (m, 2H), 1.48-1.32 (m, 6H), 1.28 (t, J=7.08 Hz, 3H), 0.93 (t, J=7.26 Hz, 3H), 0.90 (t, J=7.10 Hz, 3H)

EXAMPLE 31

Preparation of 3,4-Bis(3-methylphenyl)-1-ethoxynaphthal[c-1,2]oxaphosphinine 1-oxide

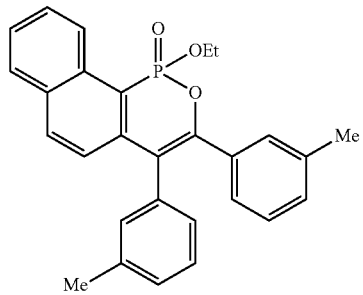 [SMILES: CCOP1(=O)OC(c2cccc(C)c2)=C(c2cccc(C)c2)c2ccc3ccccc3c21]

3,4-bis(3-methylphenyl)-1-ethoxynaphthal[c-1,2]oxaphosphinine 1-oxide (59.0 mg, 89%) as a target product was obtained under the condition of 90° C. for 16 hours, by the same reaction as the Example 1 above, except for using 1-naphthylphenylphosphonic monoethyl ester (30.0 mg, 0.15 mmol) instead of using phenylphosphonic monoethyl ester of the Example 1 above, and using 1,2-bis(3-methylphenyl)ethyne (46.0 mg, 0.23 mmol) instead of using diphenylacetylene of the Example 1 above.

$^1$H NMR (400 MHz, CDCl$_3$) δ 8.84 (d, J=8.52 Hz, 1H), 7.87-7.80 (m, 2H), 7.68-7.63 (m, 1H), 7.56-7.53 (m, 1H), 7.30-7.18 (m, 3H), 7.09-7.01 (m, 6H), 4.36-4.18 (m, 2H), 2.33 (s, 3H), 2.22 (s, 3H), 1.32 (t, J=7.08 Hz, 3H)

EXAMPLE 32

Preparation of 3-Phenyl-4-methyl-1-ethoxynaphthal[c-1,2]oxaphosphinine 1-oxide and 4-Phenyl-3-methyl-1-ethoxynaphthal[c-1,2]oxaphosphinine 1-oxide

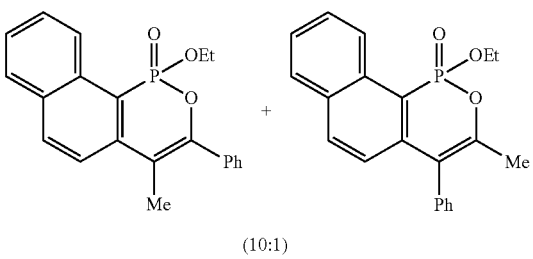 [SMILES: CCOP1(=O)OC(c2ccccc2)=C(C)c2ccc3ccccc3c21 ; CCOP1(=O)OC(C)=C(c2ccccc2)c2ccc3ccccc3c21]

(10:1)

3-phenyl-4-methyl-1-ethoxynaphthal[c-1,2]oxaphosphinine 1-oxide and 4-phenyl-3-methyl-1-ethoxynaphthal[c-1,2]oxaphosphinine 1-oxide (43.0 mg, 82%) as a target product were obtained at an isomer ratio of 10:1 under the condition of 90° C. for 8 hours, by the same reaction as the Example 1 above, except for using 1-naphthylphosphonic monoethyl ester (30.0 mg, 0.15 mmol) instead of using phenylphosphonic monoethyl ester of the Example 1 above, and using 1-propynylbenzene (26.0 mg, 0.23 mmol) instead of using diphenylacetylene of the Example 1 above.

$^1$H NMR (400 MHz, CDCl$_3$) data for the major isomer; δ 8.82 (d, J=8.52 Hz, 1H), 8.09 (d, J=8.84 Hz, 1H), 7.88 (d, J=8.20 Hz, 1H), 7.69-7.53 (m, 5H), 7.48-7.42 (m, 3H), 4.31-4.14 (m, 2H), 2.31 (d, J=0.64 Hz, 3H), 1.31 (t, J=7.08

Hz, 3H); data for the minor isomer; δ 8.74 (d, J=8.56 Hz, 1H), 7.82-7.77 (m, 2H), 7.69-7.40 (m, 7H), 6.86 (dd, J=8.80 Hz, 5.84 Hz, 1H), 4.31-4.14 (m, 2H), 2.02 (s, 3H), 1.37 (t, J=7.08 Hz, 3H)

EXAMPLE 33

Preparation of 3,4-Diethyl-1-ethoxynaphthal[c-1,2]oxaphosphinine 1-oxide

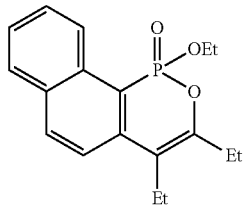 [SMILES: CCOP1(=O)OC(CC)=C(CC)c2ccc3ccccc3c21]

3,4-diethyl-1-ethoxynaphthal[c-1,2]oxaphosphinine 1-oxide (38.0 mg, 80%) as a target product was obtained under the condition of 90° C. for 12 hours, by the same reaction as the Example 1 above, except for using 1-naphthyl phosphonic monoethyl ester (30.0 mg, 0.15 mmol) instead of using phenylphosphonic monoethyl ester of the Example 1 above, and using 3-hexyne (18.0 mg, 0.23 mmol) instead of using diphenylacetylene of the Example 1 above.

$^1$H NMR (400 MHz, CDCl$_3$) δ 8.77 (d, J=8.52 Hz, 1H), 8.02 (d, J=8.46 Hz, 1H), 7.82 (d, J=8.16 Hz, 3H), 7.62-7.49 (m, 3H), 4.23-4.06 (m, 2H), 2.68-2.48 (m, 4H), 1.29 (dt, J=10.83 Hz, 4.97 Hz, 6H), 1.20 (t, J=7.50 Hz, 3H)

EXAMPLE 34

Preparation of 1-Ethoxy-3,4-diphenyl-1H-indolo[2,3-c][1,2]oxaphosphinine 1-oxide

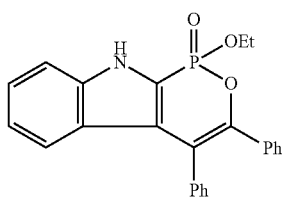 [SMILES: CCOP1(=O)OC(c2ccccc2)=C(c2ccccc2)c2c1[nH]c1ccccc21]

1-ethoxy-3,4-diphenyl-1H-indolo[2,3-c][1,2]oxaphosphinine 1-oxide (36.0 mg, 60%) as a target compound was obtained under the condition of 90° C. for 12 hours, by the same reaction as the Example 1 above, except for using 1H-indol-2-yl phosphonic monoethyl ester (34.0 mg, 0.15 mmol) instead of using phenylphosphonic monoethyl ester of the Example 1 above.

$^1$H NMR (400 MHz, CDCl$_3$) δ 11.74 (s, 1H), 7.59 (d, J=8.32 Hz, 1H), 7.44-7.32 (m, 7H), 7.26-7.17 (m, 4H), 6.81 (t, J=7.60 Hz, 1H), 6.23 (d, J=8.28 Hz, 1H), 4.25-4.11 (m, 2H), 1.30 (t, J=7.06 Hz, 3H)

EXAMPLE 35

Preparation of 1-Ethoxy-3,4-diphenyl-1H-thieno[2,3-c][1,2]oxaphosphinine 1-oxide

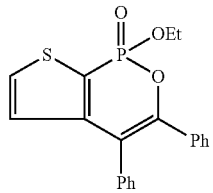 [SMILES: CCOP1(=O)OC(c2ccccc2)=C(c2ccccc2)c2ccsc21]

1-ethoxy-3,4-diphenyl-1H-thieno[2,3-c][1,2]oxaphosphinine 1-oxide (42.0 mg, 76%) as a target compound was obtained under the condition of 90° C. for 12 hours, by the same reaction as the Example 1 above, except for using 2-thienyl phosphonic monoethyl ester (29.0 mg, 0.15 mmol) instead of using phenylphosphonic monoethyl ester of the Example 1 above.

$^1$H NMR (400 MHz, CDCl$_3$) δ 7.61 (q, J=3.89 Hz, 1H), 7.36-7.32 (m, 3H), 7.26-7.12 (m, 7H), 6.73 (q, J=2.80 Hz, 1H), 4.34-4.20 (m, 2H), 1.38 (t, J=7.08 Hz, 3H)

EXAMPLE 36

Preparation of Following Chemical Compound

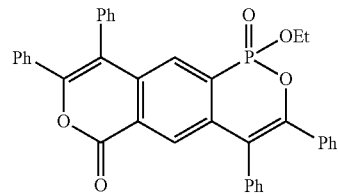 [SMILES: CCOP1(=O)OC(c2ccccc2)=C(c2ccccc2)c2cc3c(=O)oc(-c4ccccc4)c(-c4ccccc4)c3cc21]

A target compound (54.0 mg, 62%) was obtained under the condition of 90° C. for 30 hours, by the same reaction as the Example 1 above, except for using 4-(diethoxyphosphinyl)benzoic acid (35.0 mg, 0.15 mmol) instead of using phenylphosphonic monoethyl ester of the Example 1 above and using diphenylacetylene (67.0 mg, 0.38 mmol) of the Example 1 above.

$^1$H NMR (400 MHz, CDCl$_3$) δ 8.02-8.00 (m, 1H), 7.80-7.76 (m, 1H), 7.44-7.40 (m, 6H), 7.35-7.13 (m, 14H), 4.26-4.15 (m, 2H), 1.24 (t, J=7.06 Hz, 3H)

EXAMPLE 37

Preparation of Following Chemical Compound

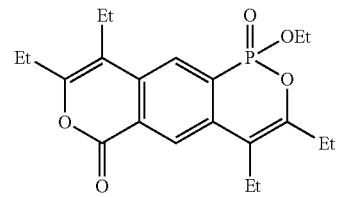 [SMILES: CCOP1(=O)OC(CC)=C(CC)c2cc3c(=O)oc(CC)c(CC)c3cc21]

A target compound (35.0 mg, 59%) was obtained under the condition of 90° C. for 30 hours, by the same reaction as the Example 1 above, except for using 4-(diethoxyphosphinyl)benzoic acid (35.0 mg, 0.15 mmol) instead of using phenylphosphonic monoethyl ester of the Example 1 above and using 3-hexyne (31.0 mg, 0.38 mmol) instead of using diphenylacetylene of the Example 1 above.

$^1$H NMR (400 MHz, CDCl$_3$) δ 8.36 (d, J=6.36, 1H), 8.02 (d, J=16.08, 1H), 4.28-4.15 (m, 2H), 2.74-2.45 (m, 8H), 1.34-1.17 (m, 15H)

EXAMPLE 38

Preparation of 1,3,4-Triphenyl-1H-2,1-benzoxaphosphinine 1-oxide

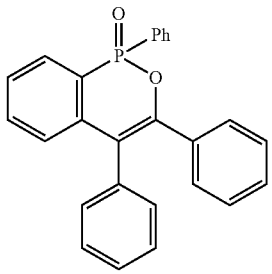 [SMILES: O=P1(c2ccccc2)OC(c2ccccc2)=C(c2ccccc2)c2ccccc21]

1,3,4-triphenyl-1H-2,1-benzoxaphosphinine 1-oxide (52.0 mg, 88%) as a target product was obtained under the condition of 90° C. for 16 hours, by the same reaction as the Example 1 above, except for using diphenylphosphinic acid (32.7 mg, 0.15 mmol) instead of using phenylphosphonic monoethyl ester of the Example 1 above, and using 1,2-diphenyl ethyne (40.0 mg, 0.23 mmol) instead of using diphenylacetylene of the Example 1 above.

$^1$H NMR (400 MHz, CDCl$_3$) δ 7.98-7.92 (m, 2H), 7.64-7.57 (m, 2H), 7.55-7.50 (m, 2H), 7.45 (tt, J=7.8, 1.3 Hz, 1H), 7.41-7.30 (m, 4H), 7.29-7.27 (m, 2H), 7.24 (t, J=1.6 Hz, 1H), 7.23 (t, J=2.0 Hz, 1H), 7.18-7.08 (m, 3H), 7.05 (dd, J=7.9, 4.8, 1H)

EXAMPLE 39

Preparation of 3,4-Bis(3-methylphenyl)-1-phenyl-1H-2,1-benzoxaphosphinine 1-oxide

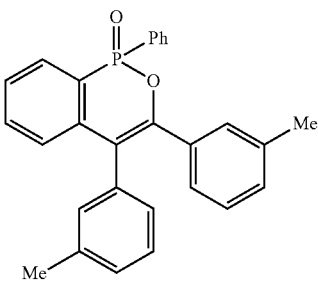 [SMILES: Cc1cccc(C2=C(c3cccc(C)c3)c3ccccc3P(=O)(c3ccccc3)O2)c1]

3,4-Bis(3-methylphenyl)-1-phenyl-1H-2,1-benzoxaphosphinine 1-oxide (48.2 mg, 76%) as a target product was obtained under the condition of 90° C. for 16 hours, by the same reaction as the Example 1 above, except for using diphenylphosphinic acid (32.7 mg, 0.15 mmol) instead of using phenylphosphonic monoethyl ester of the Example 1 above, and using 1,2-di-m-tolylethyne (46.4 mg, 0.23 mmol) instead of using diphenylacetylene of the Example 1 above.

$^1$H NMR (400 MHz, CDCl$_3$) δ 7.96-7.91 (m, 2H), 7.63-7.49 (m, 4H), 7.44 (tt, J=7.4, 1.3 Hz, 1H), 7.35-7.25 (m, 2H), 7.18-7.15 (m, 2H), 7.10 (s, 1H), 7.08-7.05 (m, 2H), 6.98-6.95 (m, 3H), 2.33 (s, 3H), 2.17 (s, 3H)

EXAMPLE 40

Preparation of 3,4-Bis(4-methylphenyl)-1-phenyl-1H-2,1-benzoxaphosphinine 1-oxide

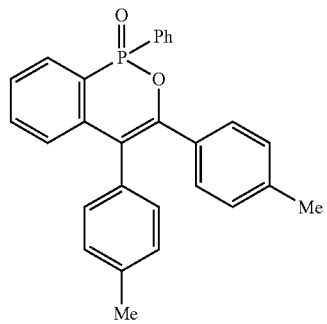 [SMILES: Cc1ccc(C2=C(c3ccc(C)cc3)c3ccccc3P(=O)(c3ccccc3)O2)cc1]

3,4-Bis(4-methylphenyl)-1-phenyl-1H-2,1-benzoxaphosphinine 1-oxide (54.5 mg, 86%) as a target product was obtained under the condition of 90° C. for 16 hours, by the same reaction as the Example 1 above, except for using diphenylphosphinic acid (32.7 mg, 0.15 mmol) instead of using phenylphosphonic monoethyl ester of the Example 1 above, and using 1,2-di-p-tolylethyne (46.4 mg, 0.23 mmol) instead of using diphenylacetylene of the Example 1 above.

$^1$H NMR (400 MHz, CDCl$_3$) δ 7.95-7.90 (m, 2H), 7.62-7.48 (m, 4H), 7.43 (t, J =7.7 Hz, 1H), 7.33-7.29 (m, 1H), 7.21-7.13 (m, 6H), 7.05 (dd, J=8.4, 4.8 Hz, 1H), 6.92 (d, J =8.1, 2H), 2.40 (s, 3H), 2.24 (s, 3H)

EXAMPLE 41

Preparation of 3,4-Bis(4-methoxyphenyl)-1-phenyl-1H-2,1-benzoxaphosphinine 1-oxide

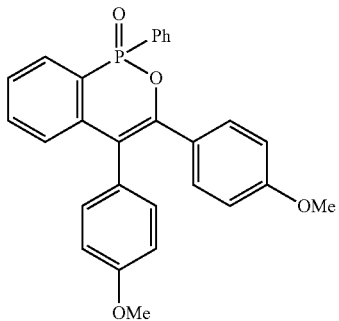 [SMILES: COc1ccc(C2=C(c3ccc(OC)cc3)c3ccccc3P(=O)(c3ccccc3)O2)cc1]

3,4-Bis(4-methoxyphenyl)-1-phenyl-1H-2,1-benzoxaphosphinine 1-oxide (62.7 mg, 92%) as a target product was obtained under the condition of 90° C. for 16 hours, by the same reaction as the Example 1 above, except for using diphenylphosphinic acid (32.7 mg, 0.15 mmol) instead of using phenylphosphonic monoethyl ester of the Example 1 above, and using 1,2-bis(4-methoxyphenyl)ethyne (53.6 mg, 0.23 mmol) instead of using diphenylacetylene of the Example 1 above.

$^1$H NMR (400 MHz, CDCl$_3$) δ 7.95-7.90 (m, 2H), 7.63-7.49 (m, 4H), 7.43 (t, J=7.7 Hz, 1H), 7.33-7.28 (m, 1H), 7.19 (app d, J=8.9 Hz, 4H), 7.07 (dd, J=8.04, 4.82 Hz, 1H), 6.94 (d, J=8.7 Hz, 2H), 6.65 (app d, J=9.0, 2H), 3.85 (s, 3H), 3.73 (s, 3H).

EXAMPLE 42

Preparation of 3,4-Bis(3-chlorophenyl)-1-phenyl-1H-2,1-benzoxaphinine 1-oxide

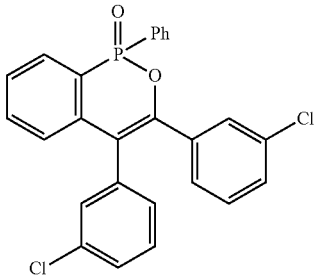 [SMILES: O=P1(c2ccccc2)OC(c2cccc(Cl)c2)=C(c2cccc(Cl)c2)c2ccccc21]

3,4-bis(3-chlorophenyl)-1-phenyl-1H-2,1-benzoxaphosphinine 1-oxide (47.3 mg, 68%) as a target product was obtained under the condition of 90° C. for 30 hours, by the same reaction as the Example 1 above, except for using diphenylphosphinic acid (32.7 mg, 0.15 mmol) instead of using phenylphosphonic monoethyl ester of the Example 1 above, and using 1,2-bis(3-chlorophenyl)ethyne (55.6 mg, 0.23 mmol) instead of using diphenylacetylene of the Example 1 above.

$^1$H NMR (400 MHz, CDCl$_3$) δ 7.95-7.90 (m, 2H), 7.67-7.47 (m, 5H), 7.41-7.33 (m, 3H), 7.31 (d, J=1.5 Hz, 2H), 7.18-7.15 (m, 2H), 7.07-7.01 (m, 3H).

EXAMPLE 43

Preparation of 3,4-Bis(4-chlorophenyl)-1-phenyl-1H-2,1-benzoxaphinine 1-oxide

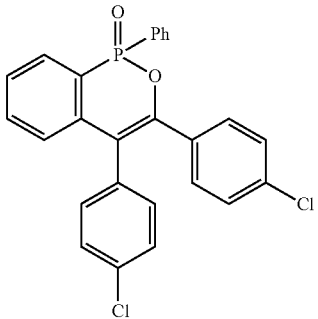 [SMILES: O=P1(c2ccccc2)OC(c2ccc(Cl)cc2)=C(c2ccc(Cl)cc2)c2ccccc21]

3,4-Bis(4-chlorophenyl)-1-phenyl-1H-2,1-benzoxaphosphinine 1-oxide (38.3 mg, 55%) as a target product was obtained under the condition of 90° C. for 30 hours, by the same reaction as the Example 1 above, except for using diphenylphosphinic acid (32.7 mg, 0.15 mmol) instead of using phenylphosphonic monoethyl ester of the Example 1 above, and using 1,2-bis(4-chlorophenyl)ethyne (55.6 mg, 0.23 mmol) instead of using diphenylacetylene of the Example 1 above.

$^1$H NMR (400 MHz, CDCl$_3$) δ 7.95-7.89 (m, 2H), 7.66-7.45 (m, 5H), 7.40-7.34 (m, 3H), 7.21 (d, J=8.2 Hz, 2H), 7.17-7.11 (m, 4H), 7.01 (dd, J=7.9, 4.8 Hz, 1H).

EXAMPLE 44

Preparation of 3,4-Bis(3-bromophenyl)-1-phenyl-1H-2,1-benzoxaphinine 1-oxide

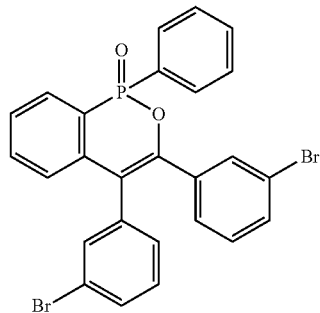 [SMILES: O=P1(c2ccccc2)OC(c2cccc(Br)c2)=C(c2cccc(Br)c2)c2ccccc21]

3,4-Bis(3-bromophenyl)-1-phenyl-1H-2,1-benzoxaphosphinine 1-oxide (48.0 mg, 58%) as a target product was obtained under the condition of 90° C. for 30 hours, by the same reaction as the Example 1 above, except for using diphenylphosphinic acid (32.7 mg, 0.15 mmol) instead of using phenylphosphonic monoethyl ester of the Example 1 above, and using 1,2-bis(3-bromophenyl)ethyne (75.6 mg, 0.23 mmol) instead of using diphenylacetylene of the Example 1 above.

$^1$H NMR (400 MHz, CDCl$_3$) δ 7.95-7.89 (m, 2H), 7.67-7.52 (m, 5H), 7.50-7.46 (m, 3H), 7.40-7.36 (m, 1H), 7.33-7.26 (m, 2H), 7.21 (d, J=7.6 Hz, 1H), 7.08-6.97 (m, 3H).

EXAMPLE 45

Preparation of 3,4-Bis(4-bromophenyl)-1-phenyl-1H-2,1-benzoxaphinine 1-oxide

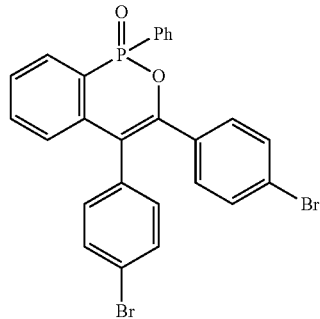 [SMILES: O=P1(c2ccccc2)OC(c2ccc(Br)cc2)=C(c2ccc(Br)cc2)c2ccccc21]

3,4-Bis(4-bromophenyl)-1-phenyl-1H-2,1-benzoxaphosphinine 1-oxide (47.2 mg, 57%) as a target product was obtained under the condition of 90° C. for 30 hours, by the same reaction as the Example 1 above, except for using diphenylphosphinic acid (32.7 mg, 0.15 mmol) instead of using phenylphosphonic monoethyl ester of the Example 1 above, and using 1,2-bis(4-bromophenyl)ethyne (75.6 mg, 0.23 mmol) instead of using diphenylacetylene of the Example 1 above.

¹H NMR (400 MHz, CDCl₃) δ 7.94-7.89 (m, 2H), 7.66-7.51 (m, 6H), 7.47 (tt, J=7.7, 1.2 Hz, 1H), 7.39-7.34 (m, 1H), 7.28 (app d, J=8.7 Hz, 2H), 7.15 (d, J=8.2 Hz, 2H), 7.09 (app d, J=8.7 Hz, 2H), 7.01 (dd, J=8.0, 4.7 Hz, 1H).

EXAMPLE 46

Preparation of 8-Methyl-1-(2-methylphenyl)-3,4-diphenyl-1H-2,1-benzoxaphosphinine 1-oxide

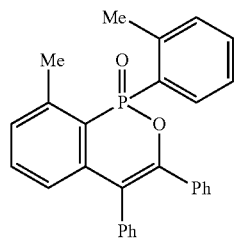 [SMILES: Cc1ccccc1P1(=O)OC(c2ccccc2)=C(c2ccccc2)c2cccc(C)c21]

8-methyl-1-(2-methylphenyl)-3,4-diphenyl-1H-2,1-benzoxaphosphinine 1-oxide (55.8 mg, 88%) as a target product was obtained under the condition of 90° C. for 16 hours, by the same reaction as the Example 1 above, except for using di-o-tolylphosphinic acid (36.9 mg, 0.15 mmol) instead of using phenylphosphonic monoethyl ester of the Example 1 above, and using 1.2-diphenyl ethyne (40.0 mg, 0.23 mmol) instead of using diphenylacetylene of the Example 1 above.

¹H NMR (400 MHz, CDCl₃) δ 8.28-8.22 (m, 1H), 7.49 (tt, J=7.5, 1.4 Hz, 1H), 7.42-7.30 (m, 5H), 7.25-7.21 (m, 3H), 7.20-7.18 (m, 2H), 7.13-7.06 (m, 4H), 6.88 (dd, J=8.1, 4.5 Hz, 1H), 2.29 (s, 3H), 2.19 (s, 3H).

EXAMPLE 47

Preparation of 6-Methoxy-1-(4-methoxyphenyl)-3,4-bis(4-methylphenyl)-1H-2,1-benzoxaphosphinine 1-oxide

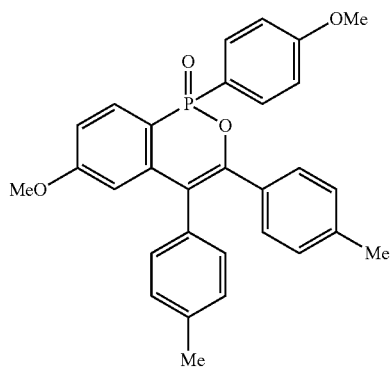 [SMILES: COc1ccc(P2(=O)OC(c3ccc(C)cc3)=C(c3ccc(C)cc3)c3cc(OC)ccc32)cc1]

6-Methoxy-1-(4-methoxyphenyl)-3,4-bis(4-methylphenyl)-1H-2,1-benzoxaphosphinine 1-oxide (60.8 mg, 84%) as a target product was obtained under the condition of 90° C. for 16 hours, by the same reaction as the Example 1 above, except for using bis(4-methoxyphenyl)phosphinic acid (41.7 mg, 0.15 mmol) instead of using phenylphosphonic monoethyl ester of the Example 1 above, and using 1,2-di-p-tolylethyne (46.4 mg, 0.23 mmol) instead of using diphenylacetylene of the Example 1 above.

¹H NMR (400 MHz, CDCl₃) δ 7.86-7.80 (m, 2H), 7.53 (dd, J=13.7, 8.4 Hz, 1H), 7.19-7.11 (m, 6H), 7.01-6.98 (m, 2H), 6.91 (d, J=8.0 Hz, 2H), 6.85 (app d, J=8.4 Hz, 1H), 6.54 (t, J=2.5 Hz, 1H), 3.86 (s, 3H), 3.68 (s, 3H), 2.39 (s, 3H), 2.23 (s, 3H).

EXAMPLE 48

Preparation of 6-Chloro-1-(4-chlorophenyl)-3,4-bis(4-methoxyphenyl)-1H-2,1-benzoxaphosphinine 1-oxide

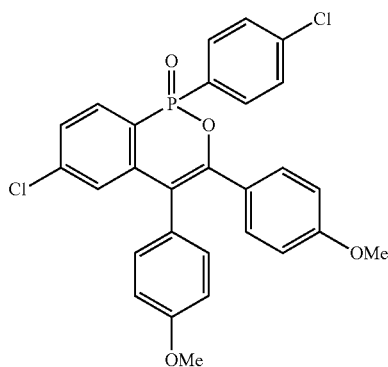 [SMILES: COc1ccc(C2=C(c3ccc(OC)cc3)c3cc(Cl)ccc3P(=O)(c3ccc(Cl)cc3)O2)cc1]

6-chloro-1-(4-chlorophenyl)-3,4-bis(4-methoxyphenyl)-1H-2,1-benzoxaphosphinine 1-oxide (69.1 mg, 88%) as a target product was obtained under the condition of 90° C. for 16 hours, by the same reaction as the Example 1 above, except for using bis(4-chlorophenyl)phosphinic acid (43.0 mg, 0.15 mmol) instead of using phenylphosphonic monoethyl ester of the Example 1 above, and using 1,2-bis(4-methoxyphenyl)ethyne (53.6 mg, 0.23 mmol) instead of using diphenylacetylene of the Example 1 above.

¹H NMR (400 MHz, CDCl₃) δ 7.87-7.81 (m, 2H), 7.52-7.44 (m, 3H), 7.29 (td, J=8.1, 2.1 Hz, 1H), 7.17-7.14 (m, 4H), 7.05 (dd, J=4.1, 4.8 Hz, 1H), 6.95 (app d, J=8.7 Hz, 2H), 6.67-6.63 (m, 2H), 3.87 (s, 3H), 3.73 (s, 3H).

EXAMPLE 49

Preparation of 7,8-Dimethyl-1-(2,3-dimethylphenyl)-3,4-bis(4-methoxyphenyl)-1H-2,1-benzoxaphosphinine 1-oxide

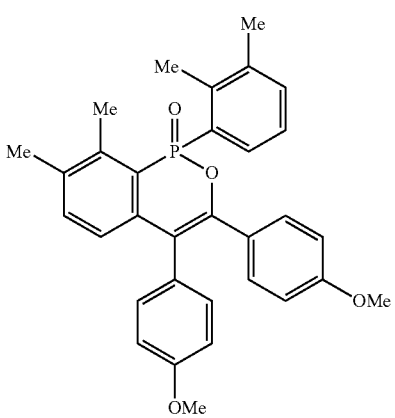 [SMILES: COc1ccc(C2=C(c3ccc(OC)cc3)c3ccc(C)c(C)c3P(=O)(c3cccc(C)c3C)O2)cc1]

7,8-dimethyl-1-(2,3-dimethylphenyl)-3,4-bis(4-methoxyphenyl)-1H-2,1-benzoxaphosphinine 1-oxide (70.5 mg, 92%) as a target product was obtained under the condition of 90 for 16 hours, by the same reaction as the Example 1 above, except for using bis(2,3-dimethylphenyl)phosphinic acid (41.1 mg, 0.15 mmol) instead of using phenylphosphonic monoethyl ester of the Example 1 above, and using 1,2-bis(4-methoxyphenyl)ethyne (53.6 mg, 0.23 mmol) instead of using diphenylacetylene of the Example 1 above.

$^1$H NMR (400 MHz, CDCl$_3$) δ 8.05 (dd, J=14.6, 7.5 Hz, 1H), 7.36 (d, J=7.4 Hz, 1H), 7.27 (td, J=7.6, 3.4 Hz, 1H), 7.16-7.10 (m, 4H), 6.91 (d, J=8.8 Hz, 2H), 6.80 (dd, J=8.2, 4.9 Hz, 1H), 6.63-6.59 (m, 2H), 3.84 (s, 3H), 3.70 (s, 3H), 2.26 (s, 6H), 2.23 (s, 3H), 2.13 (s, 3H).

EXAMPLE 50

Preparation of 1-(Naphthalen-1-yl)-3,4-di(p-methoxyphenyl)-1H-naphtho[1,2-c][1,2]oxaphosphinine 1-oxide

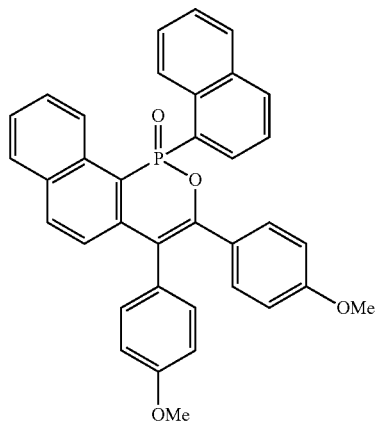 [SMILES: COc1ccc(C2=C(c3ccc(OC)cc3)c3ccc4ccccc4c3P(=O)(c3cccc4ccccc34)O2)cc1]

1-(naphthalen-1-yl)-3,4-di(p-methoxyphenyl)-1H-naphtho[1,2-c][1,2]oxaphosphinine 1-oxide (67.4 mg, 82%) as a target product was obtained under the condition of 90 for 16 hours, by the same reaction as the Example 1 above, except for using dinaphthalen-1-ylphosphinic acid (47.7 mg, 0.15 mmol) instead of using phenylphosphonic monoethyl ester of the Example 1 above, and using 1,2-bis(4-methoxyphenyl)ethyne (53.6 mg, 0.23 mmol) instead of using diphenylacetylene of the Example 1 above.

$^1$H NMR (400 MHz, CDCl$_3$) δ 8.43-8.38 (m, 2H), 8.24 (d, J=8.0 Hz, 1H), 8.05 (d, J=8.2 Hz, 1H), 7.87-7.85 (m, 2H), 7.73 (d, J=8.1 Hz, 1H), 7.58 (td, J=7.6, 2.9 Hz, 1H), 7.44-7.40 (m, 2H), 7.35 (d, J=7.8 Hz, 1H), 7.32-7.23 (m, 4H), 7.11 (d, J=8.7 Hz, 2H), 6.98 (d, J=8.4 Hz, 2H), 6.56 (d, J=8.8 Hz, 2H), 3.86 (s, 3H), 3.66 (s, 3H).

EXAMPLE 51

Preparation of 1-Thiophen-2-yl-3,4-di(p-methylphenyl)-1,2-dihydrothieno[2,3-c][1,2]oxaphosphinine 1-oxide

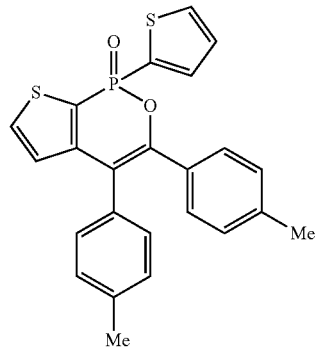 [SMILES: Cc1ccc(C2=C(c3ccc(C)cc3)c3ccsc3P(=O)(c3cccs3)O2)cc1]

1-Thiophen-2-yl-3,4-di(p-methylphenyl)-1,2-dihydrothieno[2,3-c][1,2]oxaphosphinine 1-oxide (48.2 mg, 74%) as a target product was obtained under the condition of 90 for 16 hours, by the same reaction as the Example 1 above, except for using dithiophen-2-ylphosphinic acid (34.5 mg, 0.15 mmol) instead of using phenylphosphonic monoethyl ester of the Example 1 above, and using 1,2-di-p-tolylethyne (46.4 mg, 0.23 mmol) instead of using diphenylacetylene of the Example 1 above.

$^1$H NMR (400 MHz, CDCl$_3$) δ 7.81-7.75 (m, 2H), 7.61 (dd, J=6.2, 4.9 Hz, 1H), 7.24-7.21 (m, 1H), 7.18-7.15 (m, 6H), 6.95 (d, J=8.1 Hz, 2H), 6.78 (dd, J=4.9, 2.5 Hz, 1H), 2.39 (s, 3H), 2.25 (s, 3H)

EXAMPLE 52

Preparation of 1-(2,4,6-trimethylphenyl)-3,4-diphenyl-1H-2,1-benzoxaphosphinine 1-oxide

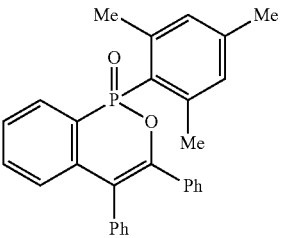 [SMILES: Cc1cc(C)c(P2(=O)OC(c3ccccc3)=C(c3ccccc3)c3ccccc32)c(C)c1]

1-(2,4,6-trimethylphenyl)-3,4-diphenyl-1H-2,1-benzoxaphosphinine 1-oxide (57.6 mg, 88%) as a target compound was obtained under the condition of 90 for 16 hours, by the same reaction as the Example 1 above, except for using mesityl(phenyl)phosphinic acid (39.0 mg, 0.15 mmol) instead of using phenylphosphonic monoethyl ester of the Example 1 above.

$^1$H NMR (400 MHz, CDCl$_3$) δ 7.48-7.43 (m, 1H), 7.41-7.34 (m, 4H), 7.30-7.24 (m, 5H), 7.14-7.08 (m, 3H), 7.02 (dd, J=8.1, 4.6 Hz, 1H), 6.97 (d, J=4.3 Hz), 2.49 (s, 6H), 2.33 (s, 3H)

EXAMPLE 53

Preparation of 1-Phenyl-3,4-diethyl-1H-2,1-benzoxaphinine 1-oxide

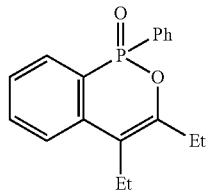 [SMILES: CCC1=C(CC)c2ccccc2P(=O)(c2ccccc2)O1]

1-Phenyl-3,4-diethyl-1H-2,1-benzoxaphinine 1-oxide (41.6 mg, 93%) as a target product was obtained under the condition of 90 for 16 hours, by the same reaction as the Example 1 above, except for using diphenylphosphinic acid (32.7 mg, 0.15 mmol) instead of using phenylphosphonic monoethyl ester of the Example 1 above, and using 3-hexyne (18 mg, 0.23 mmol) instead of using diphenylacetylene of the Example 1 above.

$^1$H NMR (400 MHz, CDCl$_3$) δ 7.82-7.77 (m, 2H), 7.59-7.51 (m, 2H), 7.50-7.44 (m, 3H), 7.30-7.26 (m, 1H), 2.60-2.34 (m, 4H), 1.23-1.16 (m, 6H)

EXAMPLE 54

Preparation of 1-Phenyl-3,4-dibutyl-1H-2,1-benzoxaphinine 1-oxide

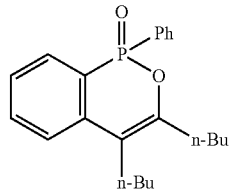

1-Phenyl-3,4-dibutyl-1H-2,1-benzoxaphinine 1-oxide (45.7 mg, 86%) as a target product was obtained under the condition of 90 for 16 hours, by the same reaction as the Example 1 above, except for using diphenylphosphinic acid (32.7 mg, 0.15 mmol) instead of using phenylphosphonic monoethyl ester of the Example 1 above, and using 5-decyne (31.1 mg, 0.23 mmol) instead of using diphenylacetylene of the Example 1 above.

$^1$H NMR (400 MHz, CDCl$_3$) δ 7.81-7.75 (m, 2H), 7.59-7.55 (m, 2H), 7.51-7.44 (m, 4H), 7.31-7.26 (m, 1H), 2.60-2.40 (m, 4H), 1.64-1.50 (m, 4H), 1.49-1.28 (m, 4H), 0.98 (t, J=7.2, 3H), 0.89 (t, J=7.34, 3H)

EXAMPLE 55

Preparation of 8-Methyl-1-(2-methylphenyl)-3,4-diethyl-1H-2,1-benzoxaphinine 1-oxide

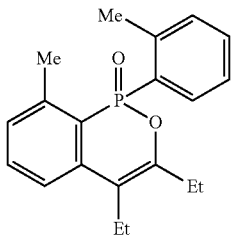 [SMILES: CCC1=C(CC)c2cccc(C)c2P(=O)(c2ccccc2C)O1]

8-methyl-1-(2-methylphenyl)-3,4-diethyl-1H-2,1-benzoxaphinine 1-oxide (42.6 mg, 87%) as a target product was obtained under the condition of 90 for 16 hours, by the same reaction as the Example 1 above, except for using di-o-tolylphosphinic acid (36.9 mg, 0.15 mmol) instead of using phenyl phosphonic monoethyl ester of the Example 1 above, and using 3-hexyne (18 mg, 0.23 mmol) instead of using diphenylacetylene of the Example 1 above.

$^1$H NMR (400 MHz, CDCl$_3$) δ 8.18-8.12 (m, 1H), 7.49-7.43 (m, 2H), 7.38-7.33 (m, 2H), 7.18 (t, J=6.5 Hz, 1H), 7.06 (dd, J=7.6, 4.3 Hz, 1H), 2.66-2.45 (m, 4H), 2.18 (s, 3H), 2.01 (s, 3H), 1.18 (td, J=7.5, 3.2 Hz, 6H).

EXAMPLE 56

Preparation of 6-Methoxy-1-(4-methoxyphenyl)-3,4-dibutyl-1H-2,1-benzoxaphinine 1-oxide

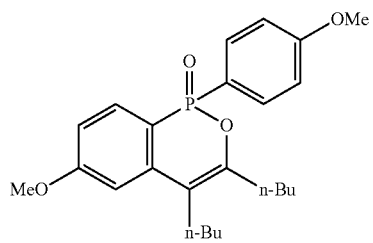

6-methoxy-1-(4-methoxyphenyl)-3,4-dibutyl-1H-2,1-benzoxaphinine 1-oxide (56.6 mg, 91%) as a target product was obtained under the condition of 90 for 16 hours, by the same reaction as the Example 1 above, except for using bis(4-methoxyphenyl)phosphinic acid (41.7 mg, 0.15 mmol) instead of using phenyl phosphonic monoethyl ester of the Example 1 above, and using 5-decyne (31.1 mg, 0.23 mmol) instead of using diphenylacetylene of the Example 1 above.

$^1$H NMR (400 MHz, CDCl$_3$) δ 7.70 (d, J=8.7 Hz, 1H), 7.66 (d, J=8.8 Hz, 1H), 7.43 (dd, J=13.8, 8.4 Hz, 1H), 6.96-6.93 (m, 3H), 6.82 (app d, J=8.4 Hz, 1H), 3.85 (s, 3H), 3.84 (s, 3H), 2.58-2.38 (m, 4H), 1.61-1.25 (m, 8H), 0.98 (t, J=7.2 Hz, 3H), 0.88 (t, J=7.3 Hz, 3H).

EXAMPLE 57

Preparation of 7-Trifluoromethyl-1-(3-trifluoromethylphenyl)-3,4-diethyl-1H-2,1-benzoxaphosphinine 1-oxide

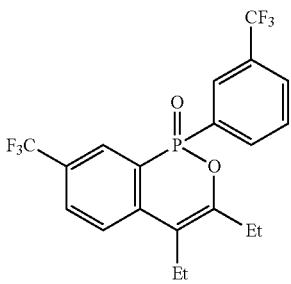 [SMILES: CCC1=C(CC)c2ccc(C(F)(F)F)cc2P(=O)(c2cccc(C(F)(F)F)c2)O1]

7-trifluoromethyl-1-(3-trifluoromethylphenyl)-3,4-diethyl-1H-2,1-benzoxaphosphinine 1-oxide (48.9 mg, 75%) as a target product was obtained under the condition of 90 for 16 hours, by the same reaction as the Example 1 above, except for using bis(3-(trifluoromethyl)phenyl)phosphinic acid (53.1 mg, 0.15 mmol) instead of using phenylphosphonic monoethyl ester of the Example 1 above, and using 3-hexyne (18 mg, 0.23 mmol) instead of using diphenylacetylene of the Example 1 above.

$^1$H NMR (400 MHz, CDCl$_3$) δ 8.07 (d, J=13.4 Hz, 1H), 7.99 (dd, J=12.8, 7.7 Hz, 1H), 7.89 (d, J=7.9 Hz, 1H), 7.85 (d, J=8.1 Hz, 1H), 7.71-7.64 (m, 3H), 2.69-2.48 (m, 4H), 1.25-1.18 (m, 6H).

EXAMPLE 58

Preparation of 6-Chloro-1-(4-chlorophenyl)-3,4-diethyl-1H-2,1-benzoxaphosphinine 1-oxide

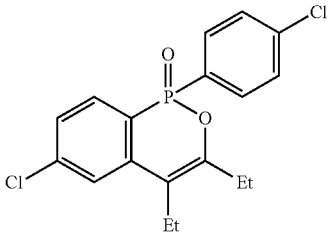 [SMILES: CCC1=C(CC)c2cc(Cl)ccc2P(=O)(c2ccc(Cl)cc2)O1]

6-chloro-1-(4-chlorophenyl)-3,4-diethyl-1H-2,1-benzoxaphosphinine 1-oxide (46.3 mg, 84%) as a target product was obtained under the condition of 90 for 16 hours, by the same reaction as the Example 1 above, except for using bis(4-chlorophenyl)phosphinic acid (53.1 mg, 0.15 mmol) instead of using phenylphosphonic monoethyl ester of the Example 1 above, and using 3-hexyne (18 mg, 0.23 mmol) instead of using diphenylacetylene of the Example 1 above.

$^1$H NMR (400 MHz, CDCl$_3$) δ 7.73-7.68 (m, 2H), 7.48-7.45 (m, 3H), 7.39 (dd, J=13.9, 8.1 Hz, 1H), 7.29-7.26 (m, 1H), 2.63-2.44 (m, 4H), 1.21 (t, J=7.3 Hz, 3H), 1.18 (t, J=7.4 Hz, 3H).

EXAMPLE 59

Preparation of 7,8-Dimethyl-1-(2,3-dimethylphenyl)-3,4-dibutyl-1H-2,1-benzoxaphosphinine 1-oxide

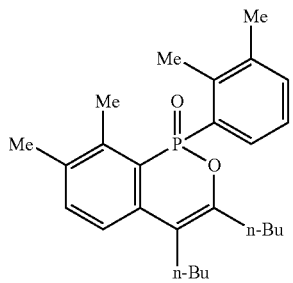

7,8-dimethyl-1-(2,3-dimethylphenyl)-3,4-dibutyl-1H-2,1-benzoxaphosphinine 1-oxide (54.8 mg, 89%) as a target product was obtained under the condition of 90 for 16 hours, by the same reaction as the Example 1 above, except for using bis(2,3-dimethylphenyl)phosphinic acid (41.1 mg, 0.15 mmol) instead of using phenylphosphonic monoethyl ester of the Example 1 above, and using 5-decyne (31.1 mg, 0.23 mmol) instead of using diphenylacetylene of the Example 1 above.

$^1$H NMR (400 MHz, CDCl$_3$) δ 7.90 (dd, J=14.6, 7.4 Hz, 1H), 7.34 (d, J=8.0 Hz, 1H), 7.33 (d, J=5.0 Hz, 1H), 7.26-7.19 (m, 2H), 2.59-2.36 (m, 4H), 2.25 (s, 3H), 2.22 (s, 3H), 2.19 (s, 3H), 2.01 (s, 3H), 1.59-1.25 (m, 8H), 0.94 (t, J=7.1 Hz, 3H), 0.87 (t, 7.3 Hz, 3H).

EXAMPLE 60

Preparation of 1-(Naphthalen-1-yl)-3,4-dibutyl-1H-naphtho[1,2-c][1,2]oxaphosphinine 1-oxide

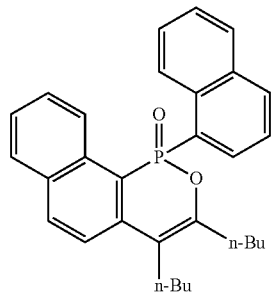

1-(naphthalen-1-yl)-3,4-dibutyl-1H-naphtho[1,2-c][1,2]oxaphosphinine 1-oxide (58.0 mg, 85%) as a target product was obtained under the condition of 90 for 16 hours, by the same reaction as the Example 1 above, except for using dinaphthalen-1-ylphosphinic acid (47.7 mg, 0.15 mmol) instead of using phenylphosphonic monoethyl ester of the Example 1 above, and using 5-decyne (31.1 mg, 0.23 mmol) instead of using diphenylacetylene of the Example 1 above.

$^1$H NMR (400 MHz, CDCl$_3$) δ 8.45 (d, J=8.4 Hz, 1H), 8.18 (d, J=8.3 Hz, 1H), 8.07-7.99 (m, 3H), 7.85 (d, J=7.9 Hz, 1H), 7.78 (d, J=8.0 Hz, 1H), 7.67 (dd, J=9.1, 4.7 Hz, 1H), 7.50-7.36 (m, 4H), 7.33-7.29 (m, 1H), 2.66 (t, J=7.8 Hz,

2H), 2.49-2.40 (m, 2H), 1.64-1.36 (m, 8H), 0.97 (t, J=7.2 Hz, 3H), 0.66 (t, J=7.3 Hz, 3H).

EXAMPLE 61

Preparation of 1-Thiophen-2-yl-3,4-diethyl-1,2-dihydrothieno[2,3-c][1,2]oxaphosphinine 1-oxide

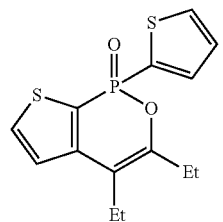 [SMILES: CCC1=C(CC)c2ccsc2P(=O)(c2cccs2)O1]

1-thiophen-2-yl-3,4-diethyl-1,2-dihydrothieno[2,3-c][1,2]oxaphosphinine 1-oxide (34.0 mg, 73%) as a target product was obtained under the condition of 90 for 16 hours, by the same reaction as the Example 1 above, except for using dithiophen-2-ylphosphinic acid (53.1 mg, 0.15 mmol) instead of using phenylphosphonic monoethyl ester of the Example 1 above, and using 3-hexyne (18.0 mg, 0.23 mmol) instead of using diphenylacetylene of the Example 1 above.

$^1$H NMR (400 MHz, CDCl$_3$) δ 7.76-7.71 (m, 2H), 7.65-7.61 (m, 1H), 7.20-7.16 (m, 2H), 2.55 (q, J=7.5 Hz), 2H), 2.50 (q, J=7.36, 2H), 1.19 (td, J=7.5, 3.0 Hz, 6H).

EXAMPLE 62

Preparation of 1,3-Diphenyl-4-methyl-1H-2,1-benzoxaphosphinine 1-oxide and 1,4-Diphenyl-3-methyl-1H-2,1-benzoxaphosphinine 1-oxide

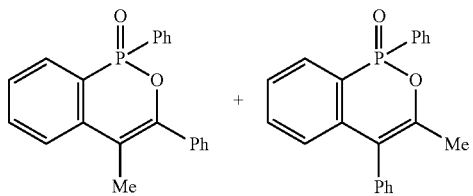

(12.5:1)

1,3-diphenyl-4-methyl-1H-2,1-benzoxaphosphinine 1-oxide and 1,4-diphenyl-3-methyl-1H-2,1-benzoxaphosphinine 1-oxide (44.9 mg, 90%) as a target product were obtained at an isomer ratio of 1:1 under the condition of 90 for 16 hours, by the same reaction as the Example 1 above, except for using diphenylphosphonic acid (32.7 mg, 0.15 mmol) instead of using phenylphosphonic monoethyl ester of the Example 1 above, and using 1-propynylbenzene (26.1 mg, 0.23 mmol) instead of using diphenylacetylene of the Example 1 above.

$^1$H NMR (400 MHz, CDCl$_3$) δ 7.91-7.85 (m, 2H), 7.67-7.55 (m, 5H), 7.53-7.46 (m, 3H), 7.43-7.35 (m, 4H), 2.29 (s, 3H).

EXAMPLE 63

Preparation of 1-(2,4,6-Trimethylphenyl)-3,4-diethyl-1H-2,1-benzoxaphosphinine 1-oxide

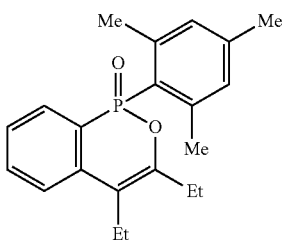 [SMILES: CCC1=C(CC)c2ccccc2P(=O)(c2c(C)cc(C)cc2C)O1]

1-(2,4,6-Trimethylphenyl)-3,4-diethyl-1H-2,1-benzoxaphosphinine 1-oxide (44.4 mg, 87%) as a target product was obtained under the condition of 90 for 16 hours, by the same reaction as the Example 1 above, except for using mesityl (phenyl)phosphinic acid (39.0 mg, 0.15 mmol) instead of using phenylphosphonic monoethylester of the Example 1 above, and using 3-hexyne (18 mg, 0.23 mmol) instead of using diphenylacetylene of the Example 1 above.

$^1$H NMR (400 MHz, CDCl$_3$) δ 7.54-7.47 (m, 2H), 7.35-7.30 (m, 1H), 7.24-7.19 (m, 1H), 6.92 (s, 1H), 6.91 (s, 1H), 2.70-2.49 (m, 4H), 2.36 (s, 6H), 2.31 (s, 3H), 1.23 (t, J=7.9 Hz, 3H), 1.21 (t, J=7.9 Hz, 3H).

EXAMPLE 64

Preparation of 2-Ethoxy-3,5,6-triphenyl-1,2-oxaphosphinine 2-oxide

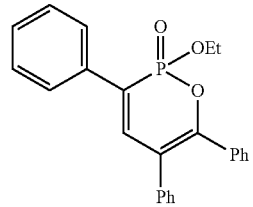 [SMILES: CCOP1(=O)OC(c2ccccc2)=C(c2ccccc2)C=C1c1ccccc1]

1-Phenylethenyl phosphonic monoethylester (32.0 mg, 0.15 mmol), diphenylacetylene (40.0 mg, 0.23 mmol), [Rh(C$_5$Me$_5$)Cl$_2$]$_2$ (1.9 mg, 0.003 mmol), silver carbonate (Ag2CO3)(41.0 mg, 0.15 mmol) and dimethylformamide (DMF)(0.8 mL) were added dropwise to a test tube in a nitrogen atmosphere and stirred at 120 for 10 hours. Whether or not the reaction proceeds was confirmed by TLC, and extraction with dichloromethane (DCM) and filtration through celite were performed to complete the reaction. The extracted organic layer was dried over anhydrous magnesium sulfate and filtered. A solvent was removed and then separation was performed by column chromatography to obtain 2-ethoxy-3,5,6-triphenyl-1,2-oxaphosphinine 2-oxide (47.0 mg, 80%) as a target compound.

$^1$H NMR (400 MHz, CDCl$_3$) δ 7.72-7.70 (m, 2H), 7.42-7.34 (m, 3H), 7.31-7.27 (m, 5H), 7.25-7.17 (m, 6H), 4.28-4.18 (m, 2H), 1.29 (t, J=7.08 Hz, 3H)

EXAMPLE 65

Preparation of 2-Ethoxy-3-phenyl-5,6-bis(4-methoxyphenyl)-1,2-oxaphosphinine 2-oxide

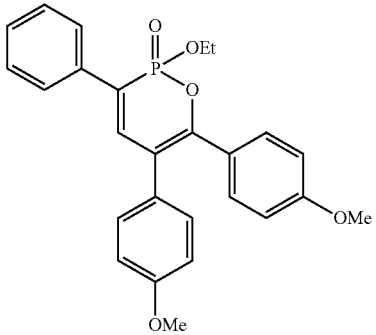 [SMILES: CCOP1(=O)OC(c2ccc(OC)cc2)=C(c2ccc(OC)cc2)C=C1c1ccccc1]

2-Ethoxy-3-phenyl-5,6-bis(4-methoxyphenyl)-1,2-oxaphosphinine 2-oxide (57.0 mg, 85%) as a target compound was obtained under the condition of 120 for 8 hours, by the same reaction as the Example 64 above, except for using 1,2-bis(4-methoxyphenyl)ethyne (53.6 mg, 0.23 mmol) instead of using diphenylacetylene of the Example 64 above.

$^1$H NMR (400 MHz, CDCl$_3$) δ 7.71-7.68 (m, 2H), 7.40-7.32 (m, 3H), 7.27-7.12 (m, 5H), 6.86-6.70 (m, 4H), 4.22-4.16 (m, 2H), 3.80 (s, 3H), 3.77 (s, 3H), 1.28 (t, J=7.08 Hz, 3H)

EXAMPLE 66

Preparation of 2-Ethoxy-3,6-diphenyl-5-methyl-1,2-oxaphosphinine 2-oxide and 2-Ethoxy-3,5-diphenyl-6-methyl-1,2-oxaphosphinine 2-oxide

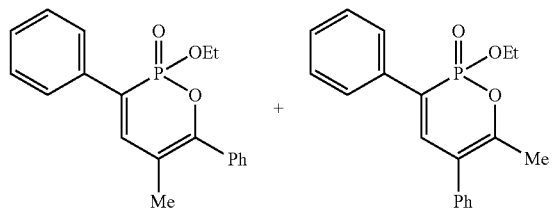

2-Ethoxy-3,6-diphenyl-5-methyl-1,2-oxaphosphinine 2-oxide and 2-ethoxy-3,5-diphenyl-6-methyl-1,2-oxaphosphinine 2-oxide (40.0 mg, 82%) as a target product were obtained at an isomer ratio of 1:1 under the condition of 120 for 6 hours, by the same reaction as the Example 64 above, except for using 1-propynylbenzene (26.0 mg, 0.23 mmol) instead of using diphenylacetylene of the Example 64 above.

$^1$H NMR (400 MHz, CDCl$_3$) data for the major isomer; δ 7.70-7.68 (m, 2H), 7.58-7.56 (m, 2H), 7.46-7.33 (m, 6H), 7.04 (d, J=40.33 Hz, 1H), 4.18-4.11 (m, 2H), 2.12 (d, J=0.92 Hz, 3H), 1.24 (t, J=7.06 Hz, 3H); data for the minor isomer; δ 7.70-7.68 (m, 2H), 7.58-7.56 (m, 2H), 7.46-7.33 (m, 6H), 7.04 (d, J=40.33 Hz, 1H), 4.18-4.11 (m, 2H), 2.12 (d, J=0.92 Hz, 3H), 1.24 (t, J=7.08 Hz, 3H)

EXAMPLE 67

Preparation of 2-Ethoxy-3-phenyl-5,6-diethyl-1,2-oxaphosphinine 2-oxide

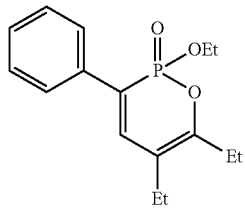 [SMILES: CCOP1(=O)OC(CC)=C(CC)C=C1c1ccccc1]

2-Ethoxy-3-phenyl-5,6-diethyl-1,2-oxaphosphinine 2-oxide (33 mg, 75%) as a target compound was obtained under the condition of 120 for 6 hours, by the same reaction as the Example 64 above, except for using 3-hexyne (18.0 mg, 0.23 mmol) instead of using diphenylacetylene of the Example 64 above.

$^1$H NMR (400 MHz, CDCl$_3$) δ 7.64-7.61 (m, 2H), 7.39-7.29 (m, 3H), 6.90 (d, J=40.53 Hz, 1H), 4.11-4.04 (m, 2H), 2.45-2.39 (m, 2H), 2.29-2.19 (m, 2H), 1.22 (dt, J=14.58 Hz, 5.65 Hz, 6H), 1.10 (t, J=7.54 Hz, 3H)

EXAMPLE 68

Preparation of 2-Ethoxy-3-(4-methylphenyl)-5,6-diphenyl-1,2-oxaphosphinine 2-oxide

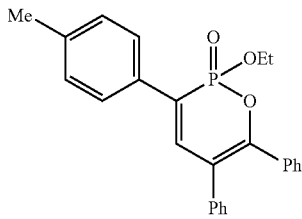 [SMILES: CCOP1(=O)OC(c2ccccc2)=C(c2ccccc2)C=C1c1ccc(C)cc1]

2-Ethoxy-3-(4-methylphenyl)-5,6-diphenyl-1,2-oxaphosphinine 2-oxide (55.0 mg, 91%) as a target compound was obtained under the condition of 120 for 12 hours, by the same reaction as the Example 64 above, except for using 1-(4-methylphenyl)ethenyl phosphonic monoethylester (34.0 mg, 0.15 mmol) instead of using 1-phenylethenyl phosphonic monoethylester of the Example 64 above.

$^1$H NMR (400 MHz, CDCl$_3$) δ 7.61 (d, J=7.00 Hz, 2H), 7.31-7.14 (m, 13H), 4.26-4.16 (m, 2H), 1.29 (t, J=7.08 Hz, 3H)

EXAMPLE 69

Preparation of 2-Ethoxy-3-phenyl-5,6-dibutyl-1,2-oxaphosphinine 2-oxide

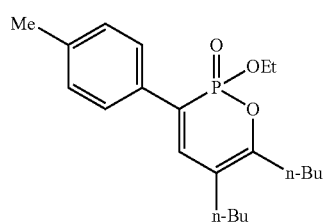

2-Ethoxy-3-phenyl-5,6-dibutyl-1,2-oxaphosphinine 2-oxide (47.0 mg, 87%) as a target compound was obtained under the condition of 120 for 8 hours, by the same reaction as the Example 64 above, except for using 1-(4-methylphenyl)ethenyl phosphonic monoethylester (34.0 mg, 0.15 mmol) instead of using 1-phenylethenyl phosphonic monoethylester of the Example 64 above and using 5-decyne (31.0 mg, 0.23 mmol) instead of using diphenylacetylene of the Example 64 above.

¹H NMR (400 MHz, CDCl₃) δ 7.53-7.51 (m, 2H), 7.17 (d, J=8.24 Hz, 2H), 6.86 (d, J=40.73 Hz, 1H), 4.09-4.02 (m, 2H), 2.39 (d, J=7.46 Hz, 2H), 2.35 (s, 3H), 2.26-2.14 (m, 2H), 1.66-1.58 (m, 2H), 1.45-1.31 (m, 6H), 1.23 (t, J=7.08 Hz, 3H), 0.93 (q, J=7.12 Hz, 6H)

EXAMPLE 70

Preparation of 2-Ethoxy-3-(4-chlorophenyl)-5,6-bis(3-methylphenyl)-1,2-oxaphosphinine 2-oxide

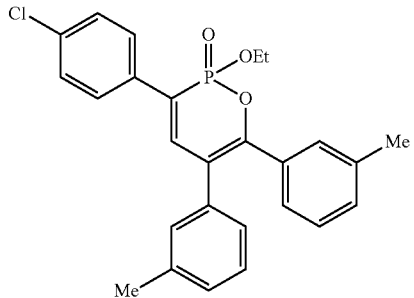 [SMILES: CCOP1(=O)OC(c2cccc(C)c2)=C(c2cccc(C)c2)C=C1c1ccc(Cl)cc1]

2-Ethoxy-3-(4-chlorophenyl)-5,6-bis(3-methylphenyl)-1,2-oxaphosphinine 2-oxide (53.0 mg, 78%) as a target compound was obtained under the condition of 120 for 16 hours, by the same reaction as the Example 64 above, except for using 1-(4-chlorophenyl)ethenyl phosphonic monoethylester (37.0 mg, 0.15 mmol) instead of using 1-phenylethenyl phosphonic monoethylester of the Example 64 above and using 1,2-bis(3-methylphenyl)ethyne (46.0 mg, 0.23 mmol) instead of using diphenylacetylene of the Example 64 above.

¹H NMR (400 MHz, CDCl₃) δ 7.67-7.64 (m, 2H), 7.37-7.35 (m, 2H), 7.24-6.96 (m, 9H), 4.25-4.18 (m, 2H), 2.30 (s, 3H), 2.23 (s, 3H), 1.29 (t, J=7.08 Hz, 3H)

EXAMPLE 71

Preparation of 2-Ethoxy-3-(4-chlorophenyl)-5,6-dibutyl-1,2-oxaphosphinine 2-oxide

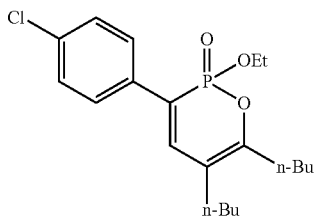

2-Ethoxy-3-(4-chlorophenyl)-5,6-dibutyl-1,2-oxaphosphinine 2-oxide (42.0 mg, 73%) as a target compound was obtained under the condition of 120 for 12 hours, by the same reaction as the Example 64 above, except for using ethenyl phosphonic monoethylester (37.0 mg, 0.15 mmol) instead of using 1-phenylethenyl phosphonic monoethylester of the Example 64 above and using 5-decyne (31.0 mg, 0.23 mmol) instead of using diphenylacetylene of the Example 64 above.

¹H NMR (400 MHz, CDCl₃) δ 7.59-7.55 (m, 2H), 7.35-7.32 (m, 2H), 6.87 (d, J=40.17 Hz, 1H), 4.11-4.03 (m, 2H), 2.41-2.37 (m, 2H), 2.24-2.16 (m, 2H), 1.66-1.58 (m, 2H), 1.47-1.30 (m, 6H), 1.24 (t, J=7.08 Hz, 3H), 0.96-0.91 (m, 6H)

EXAMPLE 72

Preparation of 2-Ethoxy-3-methyl-5,6-diphenyl-1,2-oxaphosphinine 2-oxide

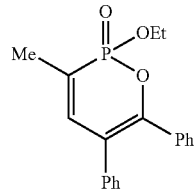

2-Ethoxy-3-methyl-5,6-diphenyl-1,2-oxaphosphinine 2-oxide (42.0 mg, 86%) as a target compound was obtained under the condition of 120 for 10 hours, by the same reaction as the Example 64 above, except for using 1-methylethenyl phosphonic monoethylester (23.0 mg, 0.15 mmol) instead of using 1-phenylethenyl phosphonic monoethylester of the Example 64 above.

¹H NMR (400 MHz, CDCl₃) δ 7.27-7.23 (m, 4H), 7.22-7.12 (m, 6H), 6.79 (dd, J=42.25 Hz, 1.60 Hz, 1H), 4.31-4.22 (m, 2H), 2.17 (dd, J=15.54 Hz, 1.54 Hz, 3H), 1.40 (t, J=7.08 Hz, 3H)

EXAMPLE 73

Preparation of 2-Ethoxy-3-methyl-5-(4-methylphenyl)-6-(4-methoxyphenyl)-1,2-oxaphosphinine 2-oxide and 2-Ethoxy-3-methyl-6-(4-methylphenyl)-5-(4-methoxyphenyl)-1,2-oxaphosphinine 2-oxide

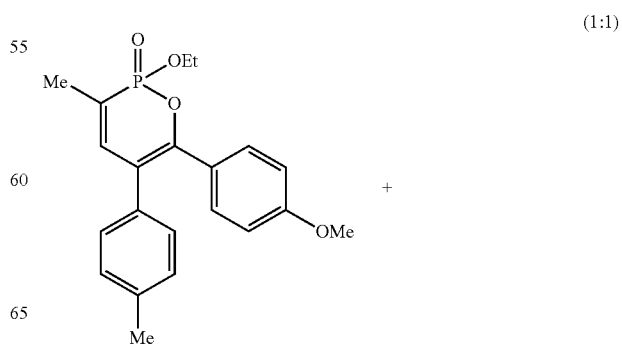

(1:1)

-continued

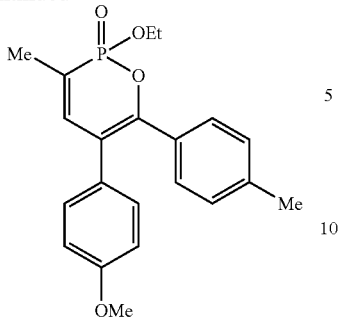

2-Ethoxy-3-methyl-5-(4-methylphenyl)-6-(4-methoxyphenyl)-1,2-oxaphosphinine 2-oxide and 2-ethoxy-3-methyl-6-(4-methylphenyl)-5-(4-methoxyphenyl)-1,2-oxaphosphinine 2-oxide as a target product were obtained at an isomer ratio of 1:1 under the condition of 120 for 10 hours, by the same reaction as the Example 64 above, except for using 1-methylethenyl phosphonic monoethylester (23.0 mg, 0.15 mmol) instead of using 1-phenylethenyl phosphonic monoethylester of the Example 64 above, and using 1-methoxy-4-(p-tolylethynyl)benzene (50.0 mg, 0.23 mmol) instead of using diphenylacetylene of the Example 64 above.

$^1$H NMR (400 MHz, CDCl$_3$) data for the major isomer; δ 7.19-7.11 (m, 2H), 7.09-6.96 (m, 4H), 6.82-6.66 (m, 3H), 4.28-4.19 (m, 2H), 3.79 (s, 3H), 2.33 (s, 3H), 2.17 (q, J=1.50 Hz, 3H), 1.39 (t, J=7.06 Hz, 3H); data for the minor isomer; δ 7.19-7.11 (m, 2H), 7.09-6.96 (m, 4H), 6.82-6.66 (m, 3H), 4.28-4.19 (m, 2H), 3.76 (s, 3H), 2.28 (s, 3H), 2.13 (q, J=1.52 Hz, 3H), 1.38 (t, J=7.08 Hz, 3H)

EXAMPLE 74

Preparation of 2-Ethoxy-3-methyl-5,6-dibutyl-1,2-oxaphosphinine 2-oxide

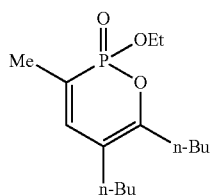

2-Ethoxy-3-methyl-5,6-dibutyl-1,2-oxaphosphinine 2-oxide (33.0 mg, 77%) as a target compound was obtained under the condition of 120 for 8 hours, by the same reaction as the Example 64 above, except for using 1-methylethenyl phosphonic monoethylester (23.0 mg, 0.15 mmol) instead of using 1-phenylethenyl phosphonic monoethylester of the Example 64 above and using 5-decyne (31.0 mg, 0.23 mmol) instead of using diphenylacetylene of the Example 64 above.

$^1$H NMR (400 MHz, CDCl$_3$) δ 6.44 (dd, J=42.13 Hz, 1.56 Hz, 1H), 4.17-4.04 (m, 2H), 2.33-2.29 (m, 3H), 2.10-2.03 (m, 5H), 1.60-1.52 (m, 2H), 1.41-1.25 (m, 9H), 0.90 (dt, J=10.70 Hz, 2.83 Hz, 6H)

EXAMPLE 75

Preparation of 3,4-Diphenyl-1-ethoxybenz[c-1,2]oxaphosphinine 1-oxide

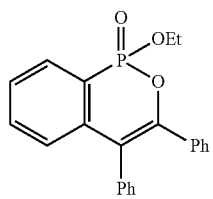

Phenylphosphonic monoethylester (37 mg, 0.2 mmol), diphenylacetylene (53 mg, 0.3 mmol), dichloro(p-cymene)ruthenium(II)dimer ([RuCl$_2$(p-cymene)]$_2$) (12.3 mg, 0.02 mmol), silver carbonate (Ag$_2$CO$_3$) (55 mg, 0.2 mmol), silver acetate (AgOAc) (33 mg, 0.2 mmol), potassium hexafluorophosphate (KPF$_6$) (7 mg, 0.04 mmol), tert-butanol (t-BuOH)(1.3 mL) were added dropwise to a V-vial and stirred at 90 for 30 hours. Whether or not the reaction proceeds was confirmed by TLC, and extraction with dichloromethane (DCM) and filtration through celite were performed to complete the reaction. The extracted organic layer was dried over anhydrous magnesium sulfate and filtered. A solvent was removed and then separation was performed by column chromatography to obtain 3,4-diphenyl-1-ethoxybenz[c-1,2]oxaphosphinine 1-oxide (66 mg, 91%) as a target compound.

$^1$H NMR (400 MHz, CDCl$_3$) δ 7.94-7.92 (m, 1H), 7.50-7.40 (m, 2H), 7.39-7.33 (m, 3H), 7.25-7.11 (m, 7H), 6.98-6.93 (m, 1H), 4.33-4.19 (m, 2H), 1.32 (t, J=7.08 Hz, 3H)

EXAMPLE 76

Preparation of 3,4-Bis(3-methylphenyl)-1-ethoxybenz[c-1,2]oxaphosphinine 1-oxide

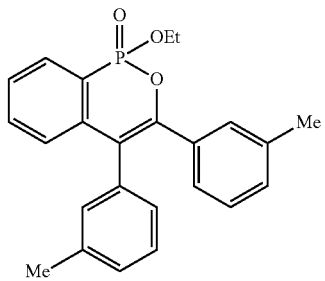 [SMILES: CCOP1(=O)OC(c2cccc(C)c2)=C(c2cccc(C)c2)c2ccccc21]

3,4-Bis(3-methylphenyl)-1-ethoxybenz[c-1,2]oxaphosphinine 1-oxide (64 mg, 82%) as a target compound was obtained under the condition of 90 for 30 hours, by the same reaction as the Example 75 above, except for using 1,2-bis(3-methylphenyl)ethyne (62 mg, 0.3 mmol) instead of using diphenylacetylene of the Example 75 above.

$^1$H NMR (400 MHz, CDCl$_3$) δ 7.97-7.91 (m, 1H), 7.49-7.39 (m, 2H), 7.26-7.15 (m, 4H), 7.02-6.94 (m, 5H), 4.30-4.17 (m, 2H), 2.31 (s, 3H), 2.20 (s, 3H), 1.31 (t, J=7.06 Hz, 3H)

EXAMPLE 77

Preparation of 3,4-Bis(4-methylphenyl)-1-ethoxy-benz[c-1,2]oxaphosphinine 1-oxide

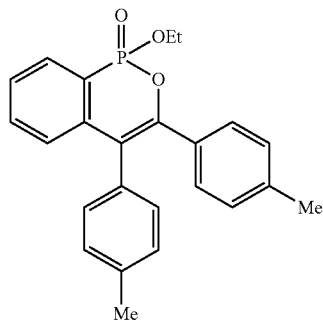 [SMILES: CCOP1(=O)OC(c2ccc(C)cc2)=C(c2ccc(C)cc2)c2ccccc21]

3,4-Bis(4-methylphenyl)-1-ethoxybenz[c-1,2]oxaphosphinine 1-oxide (60 mg, 77%) as a target compound was obtained under the condition of 90 for 30 hours, by the same reaction as the Example 75 above, except for using 1,2-bis(4-methylphenyl)ethyne (62 mg, 0.3 mmol) instead of using diphenylacetylene of the Example 75 above.

$^1$H NMR (400 MHz, CDCl$_3$) δ 7.96-7.90 (m, 1H), 7.46-7.37 (m, 2H), 7.25-7.07 (m, 6H), 6.97-6.94 (m, 3H), 4.30-4.16 (m, 2H), 2.38 (s, 3H), 2.26 (s, 3H), 1.30 (t, J=7.06 Hz, 3H)

EXAMPLE 78

Preparation of 3,4-Bis(4-methoxyphenyl)-1-ethoxy-benz[c-1,2]oxaphosphinine 1-oxide

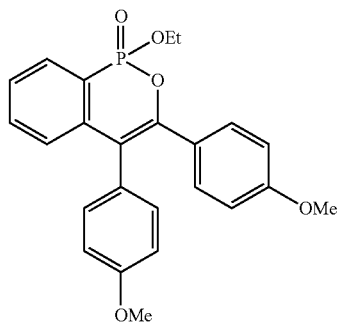 [SMILES: CCOP1(=O)OC(c2ccc(OC)cc2)=C(c2ccc(OC)cc2)c2ccccc21]

3,4-Bis(4-methoxyphenyl)-1-ethoxybenz[c-1,2]oxaphosphinine 1-oxide (70 mg, 83%) as a target compound was obtained under the condition of 90 for 30 hours, by the same reaction as the Example 75 above, except for using 1,2-bis(4-methoxyphenyl)ethyne (72 mg, 0.3 mmol) instead of using diphenylacetylene of the Example 75 above.

$^1$H NMR (400 MHz, CDCl$_3$) δ 7.95-7.89 (m, 1H), 7.48-7.43 (m, 1H), 7.41-7.37 (m, 1H), 7.19 (dt, J=9.17 Hz, 2.56 Hz, 2H), 7.14-7.10 (m, 2H), 7.00-6.96 (m, 1H), 6.93-6.89 (m, 2H), 7.19 (dt, J=9.20 Hz, 2.52 Hz, 2H), 4.30-4.15 (m, 2H), 3.84 (s, 3H), 3.75 (s, 3H), 1.31 (t, J=4.82 Hz, 3H)

EXAMPLE 79

Preparation of 3,4-Bis(3-chlorophenyl)-1-ethoxy-7-methyl-benz[c-1,2]oxaphosphinine 1-oxide

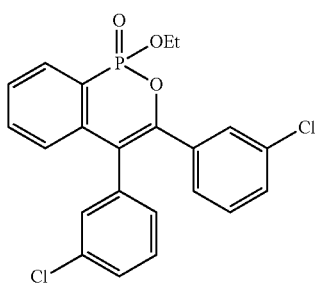 [SMILES: CCOP1(=O)OC(c2cccc(Cl)c2)=C(c2cccc(Cl)c2)c2ccccc21]

3,4-Bis(3-chlorophenyl)-1-ethoxy-7-methyl-benz[c-1,2]oxaphosphinine 1-oxide (45 mg, 52%) as a target compound was obtained under the condition of 90 for 30 hours, by the same reaction as the Example 75 above, except for using 1,2-bis(3-chlorophenyl)ethyne (74 mg, 0.3 mmol) instead of using diphenylacetylene of the Example 75 above.

$^1$H NMR (400 MHz, CDCl$_3$) δ 7.99-7.93 (m, 1H), 7.54-7.45 (m, 2H), 7.39-7.30 (m, 3H), 7.26-7.18 (m, 2H), 7.11-7.02 (m, 3H), 6.95-6.91 (m, 1H), 4.35-4.21 (m, 2H), 1.34 (t, J=7.06 Hz, 3H)

EXAMPLE 80

Preparation of 3,4-Bis(4-chlorophenyl)-1-ethoxy-benz[c-1,2]oxaphosphinine 1-oxide

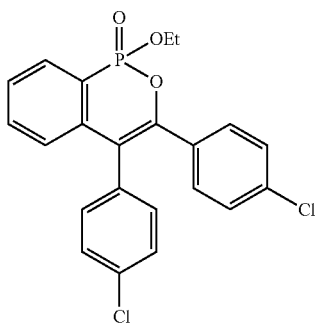 [SMILES: CCOP1(=O)OC(c2ccc(Cl)cc2)=C(c2ccc(Cl)cc2)c2ccccc21]

3,4-Bis(4-chlorophenyl)-1-ethoxybenz[c-1,2]oxaphosphinine 1-oxide (55 mg, 64%) as a target compound was obtained under the condition of 90 for 30 hours, by the same reaction as the Example 75 above, except for using 1,2-bis(4-chlorophenyl)ethyne (74 mg, 0.3 mmol) instead of using diphenylacetylene of the Example 75 above.

$^1$H NMR (400 MHz, CDCl$_3$) δ 7.97-7.91 (m, 1H), 7.53-7.43 (m, 4H), 7.34-7.30 (m, 2H), 7.11-7.08 (m, 4H), 6.93-6.90 (m, 1H), 4.33-4.19 (m, 2H), 1.32 (t, J=7.08 Hz, 3H)

EXAMPLE 81

Preparation of 3,4-Diethyl-1-ethoxybenz[c-1,2]oxaphosphinine 1-oxide

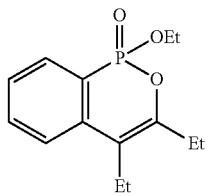 [SMILES: CCOP1(=O)OC(CC)=C(CC)c2ccccc21]

3,4-Diethyl-1-ethoxybenz[c-1,2]oxaphosphinine 1-oxide (51 mg, 96%) as a target compound was obtained under the condition of 90 for 30 hours, by the same reaction as the Example 75 above, except for using 3-hexyne (25 mg, 0.3 mmol) instead of using diphenylacetylene of the Example 75 above.

$^1$H NMR (400 MHz, CDCl$_3$) δ 7.89-7.82 (m, 1H), 7.63-7.58 (m, 1H), 7.45 (t, J=7.26 Hz, 1H), 7.40-7.35 (m, 1H), 4.23-4.09 (m, 2H), 2.60-2.42 (m, 4H), 1.31 (t, J=7.25 Hz, 3H), 1.23 (t, J=7.50 Hz, 3H), 1.16 (t, J=7.25 Hz, 3H)

EXAMPLE 82

Preparation of 3,4-Dibutyl-1-ethoxybenz[c-1,2]oxaphosphinine 1-oxide

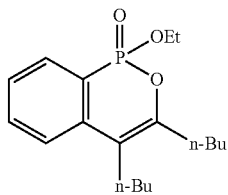

3,4-Dibutyl-1-ethoxybenz[c-1,2]oxaphosphinine 1-oxide (53 mg, 82%) as a target compound was obtained under the condition of 90 for 30 hours, by the same reaction as the Example 75 above, except for using 5-decyne (42 mg, 0.3 mmol) instead of using diphenylacetylene of the Example 75 above.

$^1$H NMR (400 MHz, CDCl$_3$) δ 7.87-7.82 (m, 1H), 7.62-7.57 (m, 1H), 7.44-7.35 (m, 2H), 4.22-4.08 (m, 2H), 2.58-2.41 (m, 2H), 1.69-1.61 (m, 2H), 1.53-1.36 (m, 6H), 1.30 (t, J=7.06 Hz, 3H), 0.95 (dt, J=7.25 Hz, 1.62 Hz, 6H)

EXAMPLE 83

Preparation of 3-Phenyl-4-methyl-1-ethoxybenz[c-1,2]oxaphosphinine 1-oxide

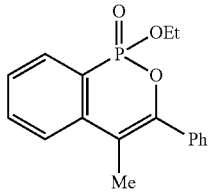

3-Phenyl-4-methyl-1-ethoxybenz[c-1,2]oxaphosphinine 1-oxide (56 mg, 93%) as a target compound was obtained under the condition of 90 for 30 hours, by the same reaction as the Example 75 above, except for using 1-propynylbenzene (35 mg, 0.3 mmol) instead of using diphenylacetylene of the Example 75 above.

$^1$H NMR (400 MHz, CDCl$_3$) δ 7.94-7.88 (m, 1H), 7.69-7.65 (m, 1H), 7.56-7.52 (m, 3H), 7.49-7.39 (m, 4H), 4.28-4.19 (m, 2H), 2.21 (d, J=0.92 Hz, 3H), 1.33 (t, J=7.08 Hz, 3H)

EXAMPLE 84

Preparation of 3,4-Diphenyl-1-ethoxy-8-methoxy-benz[c-1,2]oxa-phosphinine 1-oxide

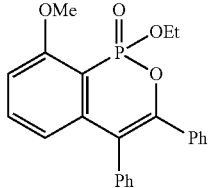 [SMILES: CCOP1(=O)OC(c2ccccc2)=C(c2ccccc2)c2cccc(OC)c21]

3,4-Diphenyl-1-ethoxy-8-methoxybenz[c-1,2]oxa-phosphinine 1-oxide (60 mg, 76%) as a target compound was obtained under the condition of 90 for 30 hours, by the same reaction as the Example 1 above, except for using 2-methoxyphenylphosphonic monoethyl ester (44 mg, 0.2 mmol) instead of using phenylphosphonic monoethyl ester of the Example 75 above.

$^1$H NMR (400 MHz, CDCl$_3$) δ 7.39 (t, J=8.22 Hz, 1H), 7.35-7.33 (m, 3H), 7.24-7.10 (m, 7H), 6.91-6.88 (m, 1H), 6.57-6.54 (m, 1H), 4.41-4.33 (m, 2H), 4.00 (s, 3H), 1.41 (t, J=7.08 Hz, 3H)

EXAMPLE 85

Preparation of 3,4-Diethyl-1-ethoxy-8-methoxybenz[c-1,2]oxaphosphinine 1-oxide

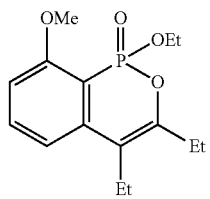 [SMILES: CCOP1(=O)OC(CC)=C(CC)c2cccc(OC)c21]

3,4-Diethyl-1-ethoxy-8-methoxybenz[c-1,2]oxaphosphinine 1-oxide (44 mg, 74%) as a target product was obtained under the condition of 90 for 30 hours, by the same reaction as the Example 75 above, except for using 2-methoxyphenylphosphonic monoethylester (44 mg, 0.2 mmol) instead of using phenylphosphonic monoethylester of the Example 75 above, and using 3-hexyne (25 mg, 0.23 mmol) instead of using diphenylacetylene of the Example 75 above.

$^1$H NMR (400 MHz, CDCl$_3$) δ 7.53 (t, J=8.22 Hz, 1H), 7.06-7.02 (m, 1H), 6.87-6.83 (m, 1H), 4.27-4.20 (m, 2H), 3.95 (s, 3H), 2.53-2.45 (m, 4H), 1.36 (t, J=7.08 Hz, 3H), 7.23 (t, J=7.50 Hz, 3H), 1.13 (t, J=7.50 Hz, 3H)

EXAMPLE 86

Preparation of 3,4-Diethyl-1-ethoxy-7-methoxybenz[c-1,2]oxaphosphinine 1-oxide and 3,4-Diethyl-1-ethoxy-5-methoxybenz[c-1,2]oxaphosphinine 1-oxide

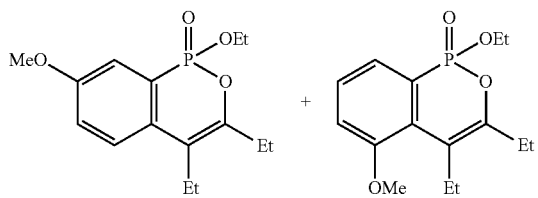 [SMILES: CCOP1(=O)OC(CC)=C(CC)c2ccc(OC)cc21 ; CCOP1(=O)OC(CC)=C(CC)c2c(OC)cccc21]

3,4-Diethyl-1-ethoxy-7-methoxybenz[c-1,2]oxaphosphinine 1-oxide and 3,4-diethyl-1-ethoxy-5-methoxybenz[c-1,2]oxaphosphinine 1-oxide (58 mg, 98%) as a target product were obtained at an isomer ratio of 2:1 under the condition of 90 for 30 hours, by the same reaction as the Example 75 above, except for using 3-methoxyphenylphosphonic monoethylester (44 mg, 0.15 mmol) instead of using phenylphosphonic monoethylester of the Example 75 above, and using 3-hexyne (25 mg, 0.3 mmol) instead of using diphenyl acetylene of the Example 75 above.

$^1$H NMR (400 MHz, CDCl$_3$) data for major isomer; δ 7.49-7.34 (m, 2H), 7.18-7.13 (m, 1H), 4.26-4.11 (m, 2H), 3.88 (s, 3H), 2.65-2.38 (m, 4H), 1.34 (t, J=7.08 Hz, 3H), 1.24 (t, J=7.44 Hz, 3H), 1.17 (t, J=7.50 Hz, 3H); data for minor isomer; δ 7.49-7.34 (m, 2H), 7.18-7.13 (m, 1H), 4.26-4.11 (m, 2H), 3.88 (s, 3H), 2.65-2.38 (m, 4H), 1.33 (t, J=7.08 Hz, 3H), 1.24 (t, J=7.44 Hz, 3H), 1.10 (t, J=7.50 Hz, 3H)

EXAMPLE 87

Preparation of 3,4-Diethyl-1-ethoxy-8-phenylbenz[c-1,2]oxaphosphinine 1-oxide

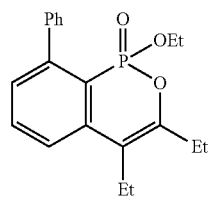 [SMILES: CCOP1(=O)OC(CC)=C(CC)c2cccc(-c3ccccc3)c21]

3,4-Diethyl-1-ethoxy-8-phenylbenz[c-1,2]oxaphosphinine 1-oxide (48 mg, 70%) as a target product was obtained under the condition of 90 for 30 hours, by the same reaction as the Example 75 above, except for using 2-biphenylphosphonic monoethylester (50 mg, 0.2 mmol) instead of using phenylphosphonic monoethylester of the Example 75 above, and using 3-hexyne (25 mg, 0.3 mmol) instead of using diphenylacetylene of the Example 75 above.

$^1$H NMR (400 MHz, CDCl$_3$) δ 7.60-7.55 (m, 3H), 7.48-7.37 (m, 4H), 7.25-7.22 (m, 1H), 3.81-3.71 (m, 1H), 3.51-3.41 (m, 1H), 2.66-2.39 (m, 4H), 1.24-1.19 (m, 6H), 0.94 (t, J=7.06 Hz, 3H)

EXAMPLE 88

Preparation of 3,4-Diphenyl-1-ethoxy-6-fluoro-benz[c-1,2]oxaphosphinine 1-oxide

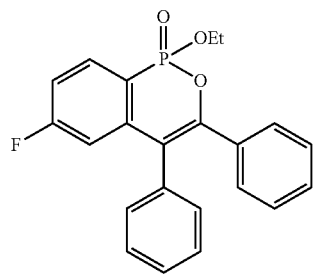 [SMILES: CCOP1(=O)OC(c2ccccc2)=C(c2ccccc2)c2cc(F)ccc21]

3,4-Diphenyl-1-ethoxy-6-fluoro-benz[c-1,2]oxaphosphinine 1-oxide (56 mg, 73%) as a target compound was obtained under the condition of 90 for 30 hours, by the same reaction as the Example 75 above, except for using 4-fluorophenylphosphonic monoethylester (41 mg, 0.2 mmol) instead of using phenylphosphonic monoethyl ester of the Example 75 above.

$^1$H NMR (400 MHz, CDCl$_3$) δ 7.98-7.91 (m, 1H), 7.39-7.35 (m, 3H), 7.26-7.10 (m, 8H), 6.67-6.62 (m, 1H), 4.33-4.19 (m, 2H), 1.32 (t, J=7.06 Hz, 3H)

EXAMPLE 89

Preparation of 3,4-Diethyl-1-ethoxy-6-fluoro-benz[c-1,2]oxaphosphinine 1-oxide

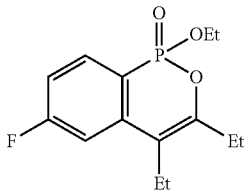 [SMILES: CCOP1(=O)OC(CC)=C(CC)c2cc(F)ccc21]

3,4-Diethyl-1-ethoxy-6-fluoro-benz[c-1,2]oxaphosphinine 1-oxide (44 mg, 77%) as a target product was obtained under the condition of 90 for 30 hours, by the same reaction as the Example 75 above, except for using 4-fluorophenylphosphonic monoethylester (41 mg, 0.2 mmol) instead of using phenylphosphonic monoethylester of the Example 75 above, and using 3-hexyne (25 mg, 0.3 mmol) instead of using diphenylacetylene of the Example 75 above.

$^1$H NMR (400 MHz, CDCl$_3$) δ 7.88-7.81 (m, 1H), 7.14-7.05 (m, 2H), 4.24-4.12 (m, 2H), 1.32 (t, J=4.92 Hz, 3H), 1.23 (t, J=7.50 Hz, 3H), 1.16 (t, J=7.54 Hz, 3H)

EXAMPLE 90

Preparation of 3,4-Diphenyl-1-ethoxy-8-chlorobenz[c-1,2]oxaphosphinine 1-oxide

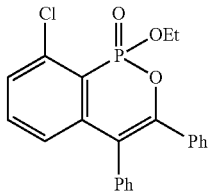

3,4-Diphenyl-1-ethoxy-8-chlorobenz[c-1,2]oxaphosphinine 1-oxide (64 mg, 81%) as a target compound was obtained under the condition of 90 for 30 hours, by the same reaction as the Example 75 above, except for using 2-chlorophenylphosphonic monoethylester (44 mg, 0.2 mmol) instead of using phenylphosphonic monoethylester of the Example 75 above.

$^1$H NMR (400 MHz, CDCl$_3$) δ 7.40-7.33 (m, 5H), 7.25-7.11 (m, 7H), 6.90-6.87 (m, 1H), 4.44-4.37 (m, 2H), 1.43 (t, J=7.08 Hz, 3H)

EXAMPLE 91

Preparation of 3,4-Diethyl-1-ethoxy-8-chlorobenz[c-1,2]oxaphosphinine 1-oxide

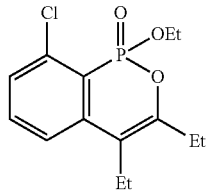 [SMILES: CCOP1(=O)OC(CC)=C(CC)c2cccc(Cl)c21]

3,4-Diethyl-1-ethoxy-8-chlorobenz[c-1,2]oxaphosphinine 1-oxide (51 mg, 85%) as a target product was obtained under the condition of 90 for 30 hours, by the same reaction as the Example 75 above, except for using 2-chlorophenylphosphonic monoethylester (44 mg, 0.2 mmol) instead of using phenylphosphonic monoethylester of the Example 75 above, and using 3-hexyne (25 mg, 0.3 mmol) instead of using diphenylacetylene of the Example 75 above.

$^1$H NMR (400 MHz, CDCl$_3$) δ 7.51 (t, J=8.06 Hz, 1H), 7.37-7.34 (m, 2H), 4.33-4.24 (m, 2H), 2.55-2.48 (m, 4H), 1.40 (t, J=7.08 Hz, 3H), 1.24 (t, J=7.50 Hz, 3H), 1.14 (t, J=7.50 Hz, 3H)

EXAMPLE 92

Preparation of 3,4-Diethyl-1-ethoxy-7-bromobenz[c-1,2]oxaphosphinine 1-oxide

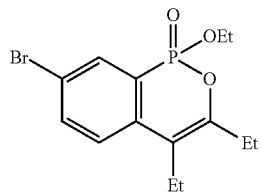

3,4-Diethyl-1-ethoxy-7-bromobenz[c-1,2]oxaphosphinine 1-oxide (51 mg, 74%) as a target product was obtained under the condition of 90 for 30 hours, by the same reaction as the Example 75 above, except for using 3-bromophenylphosphonic monoethylester (53 mg, 0.2 mmol) instead of using phenylphosphonic monoethylester of the Example 75 above, and using 3-hexyne (25 mg, 0.3 mmol) instead of using diphenylacetylene of the Example 75 above.

$^1$H NMR (400 MHz, CDCl$_3$) δ 7.95 (dd, J=2.20 Hz, J=15.16 Hz, 1H), 7.71-7.69 (m, 1H), 7.33-7.28 (m, 1H), 4.23-4.16 (m, 2H), 2.60-2.41 (m, 4H), 1.34 (t, J=7.08 Hz, 3H), 1.23 (t, J=7.50 Hz, 3H), 1.14 (t, J=7.52 Hz, 3H)

EXAMPLE 93

Preparation of 3,4-Diphenyl-1-ethoxy-7,8-dimethylbenz[c-1,2]oxaphosphinine 1-oxide

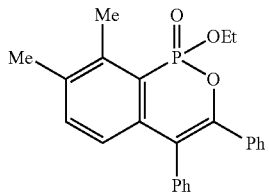 [SMILES: CCOP1(=O)OC(c2ccccc2)=C(c2ccccc2)c2ccc(C)c(C)c21]

3,4-Diphenyl-1-ethoxy-7,8-dimethylbenz[c-1,2]oxaphosphinine 1-oxide (76 mg, 97%) as a target compound was obtained under the condition of 90 for 30 hours, by the same reaction as the Example 75 above, except for using 2,3-dimethylphenylphosphonic monoethylester (43 mg, 0.2 mmol) instead of using phenylphosphonic monoethylester of the Example 75 above.

$^1$H NMR (400 MHz, CDCl$_3$) δ 7.35-7.33 (m, 3H), 7.22-7.11 (m, 8H), 6.69 (t, J=7.34 Hz, 1H), 4.33-4.15 (m, 2H), 2.70 (s, 3H), 2.32 (s, 3H), 1.35 (t, J=7.06 Hz, 3H)

EXAMPLE 94

Preparation of 3,4-Diethyl-1-ethoxy-7,8-dimethyl-benz[c-1,2]oxaphosphinine 1-oxide

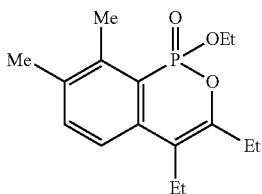 [SMILES: CCOP1(=O)OC(CC)=C(CC)c2ccc(C)c(C)c21]

3,4-Diethyl-1-ethoxy-7,8-dimethylbenz[c-1,2]oxaphosphinine 1-oxide (57 mg, 97%) as a target product was obtained under the condition of 90 for 30 hours, by the same reaction as the Example 75 above, except for using 2,3-dimethylphenylphosphonic monoethylester (43 mg, 0.2 mmol) instead of using phenylphosphonic monoethylester of the Example 75 above, and using 3-hexyne (25 mg, 0.3 mmol) instead of using diphenylacetylene of the Example 75 above.

$^1$H NMR (400 MHz, CDCl$_3$) δ 7.36 (d, J=8.20 Hz, 1H), 7.20 (t, J=7.42 Hz, 1H), 4.22-4.03 (m, 2H), 2.62 (d, J=1.68 Hz, 3H), 2.53-2.45 (m, 4H), 2.31 (s, 3H), 1.33 (t, J=7.06 Hz, 3H), 1.22 (t, J=7.50 Hz, 3H), 1.13 (t, J=7.50 Hz, 3H)

EXAMPLE 95

Preparation of 3,4-Diphenyl-1-ethoxy-6-methoxy-8-methyl-benz[c-1,2]oxaphosphinine 1-oxide

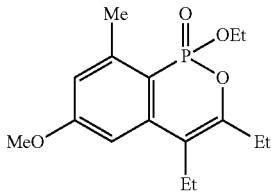 [SMILES: CCOP1(=O)OC(CC)=C(CC)c2cc(OC)cc(C)c21]

3,4-Diphenyl-1-ethoxy-6-methoxy-8-methyl-benz[c-1,2] oxaphosphinine 1-oxide (61 mg, 75%) as a target compound was obtained under the condition of 90 for 30 hours, by the same reaction as the Example 75 above, except for using 2-methyl-4-methoxyphenylphosphonic monoethylester (46 mg, 0.2 mmol) instead of using phenylphosphonic monoethyl ester of the Example 75 above.

$^1$H NMR (400 MHz, CDCl$_3$) δ 7.32 (d, J=1.76 Hz, 3H), 7.23-7.10 (m, 7H), 6.75 (t, J=2.82 Hz, 1H), 6.30-6.28 (m, 1H), 4.31-4.14 (m, 2H), 3.64 (s, 3H), 2.75 (s, 3H), 1.34 (t, J=7.08 Hz, 3H)

EXAMPLE 96

Preparation of 3,4-Diethyl-1-ethoxy-6-methoxy-8-methyl-benz[c-1,2]oxaphosphinine 1-oxide

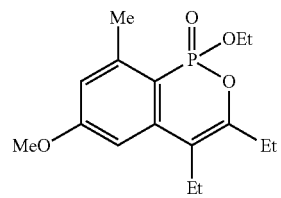 [SMILES: CCOP1(=O)OC(CC)=C(CC)c2cc(OC)cc(C)c21]

3,4-Diethyl-1-ethoxy-6-methoxy-8-methyl-benz[c-1,2] oxaphosphinine 1-oxide (58 mg, 93%) as a target product was obtained under the condition of 90 for 30 hours, by the same reaction as the Example 75 above, except for using 2-methyl-4-methoxyphenylphosphonic monoethylester (46 mg, 0.2 mmol) instead of using phenylphosphonic monoethylester of the Example 75 above, and using 3-hexyne (25 mg, 0.23 mmol) instead of using diphenylacetylene of the Example 75 above.

$^1$H NMR (400 MHz, CDCl$_3$) δ 6.80-6.78 (m, 1H), 6.71-6.70 (m, 1H), 4.20-4.02 (m, 2H), 3.86 (s, 3H), 2.67 (d, J=1.60 Hz, 3H), 2.56-2.41 (m, 4H), 1.32 (t, J=7.08 Hz, 3H), 1.23 (t, J=7.50 Hz, 3H), 1.14 (t, J=7.50 Hz, 3H)

EXAMPLE 97

Preparation of 3,4-Diethyl-7,8-(methylenedioxy)-1-ethoxybenz[c-1,2]oxaphosphinine 1-oxide

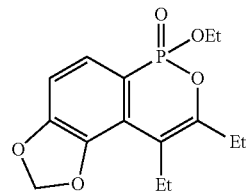 [SMILES: CCOP1(=O)OC(CC)=C(CC)c2c1ccc1c2OCO1]

3,4-Diethyl-7,8-(methylenedioxy)-1-ethoxybenz[c-1,2] oxaphosphinine 1-oxide (50 mg, 81%) as a target product was obtained under the condition of 90 for 30 hours, by the same reaction as the Example 75 above, except for using 1,3-benzodioxol-5-ylphosphonic monoethylester (46 mg, 0.2 mmol) instead of using phenylphosphonic monoethylester of the Example 75 above, and using 3-hexyne (25 mg, 0.23 mmol) instead of using diphenylacetylene of the Example 75 above.

$^1$H NMR (400 MHz, CDCl$_3$) δ 7.42 (q, J=7.72 Hz, 1H), 6.87 (q, J=3.69 Hz, 1H), 6.02 (dd, J=6.30 Hz, 1.38 Hz, 2H), 4.18-4.07 (m, 2H), 2.72-2.37 (m, 4H), 1.29 (t, J=7.06 Hz, 3H), 1.21 (t, J=7.48 Hz, 3H), 1.10 (t, J=7.36 Hz, 3H)

EXAMPLE 98

Preparation of 3,4-Diphenyl-1-ethoxynaphthal[c-1,2]oxaphosphinine 1-oxide

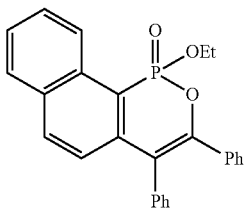 [SMILES: CCOP1(=O)OC(c2ccccc2)=C(c2ccccc2)c2ccc3ccccc3c21]

3,4-Diphenyl-1-ethoxynaphthal[c-1,2]oxaphosphinine 1-oxide (68 mg, 82%) as a target compound was obtained under the condition of 90 for 30 hours, by the same reaction as the Example 75 above, except for using 1-naphthylphosphonic monoethylester (48 mg, 0.2 mmol) instead of using phenylphosphonic monoethylester of the Example 75 above.

$^1$H NMR (400 MHz, CDCl$_3$) δ 8.84 (d, J=8.48 Hz, 1H), 7.88-7.82 (m, 2H), 7.69-7.65 (m, 1H), 7.58-7.54 (m, 1H), 7.40-7.39 (m, 3H), 7.29-7.15 (m, 7H), 7.08-7.04 (m, 1H), 4.37-4.21 (m, 2H), 1.33 (t, J=7.08 Hz, 3H)

EXAMPLE 99

Preparation of Following Chemical Compounds

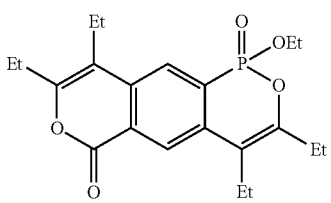 [SMILES: CCOP1(=O)OC(CC)=C(CC)c2cc3c(=O)oc(CC)c(CC)c3cc21]

4-Ethoxy-4-hydroxyphosphinylbenzoicacid (46 mg, 0.2 mmol), 3-hexyne (41 mg, 0.5 mmol), [RuCl$_2$(p-cymene)]$_2$ (24.6 mg, 0.04 mmol)), silver carbonate (Ag$_2$CO$_3$) (110 mg, 0.4 mmol), silver acetate (AgOAc) (66 mg, 0.4 mmol), potassium hexafluorophosphate (KPF$_6$) (14 mg, 0.08 mmol), and tert-butanol (t-BuOH) (1.3 mL) were added dropwise to a V-vial and stirred at 90 for 30 hours. Whether or not the reaction proceeds was confirmed by TLC, and extraction with dichloromethane (DCM) and filtration through celite were performed to complete the reaction. The extracted organic layer was dried over anhydrous magnesium sulfate and filtered. A solvent was removed and then separation was performed by column chromatography to obtain a target compound (71 mg, 91%).

$^1$H NMR (400 MHz, CDCl$_3$) δ 8.36 (d, J=6.36 Hz, 1H), 8.02 (d, J=16.08 Hz, 1H), 4.28-4.15 (m, 2H), 2.74-2.45 (m, 8H), 1.34-1.17 (m, 15H)

EXAMPLE 100

Preparation of 1,3,4-Triphenyl-1H-2,1-benzoxaphosphinine 1-oxide

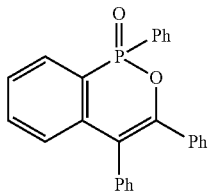 [SMILES: O=P1(c2ccccc2)OC(c2ccccc2)=C(c2ccccc2)c2ccccc21]

Diphenylphosphinic acid (33 mg, 0.15 mmol), diphenylacetylene (41 mg, 0.23 mmol), [RuCl$_2$(p-cymene)]$_2$ (9.2 mg, 0.015 mmol), silver carbonate (Ag$_2$CO$_3$) (41 mg, 0.15 mmol), silver acetate (AgOAc) (25 mg, 0.15 mmol), potassium hexafluorophosphate (KPF$_6$) (5.5 mg, 0.03 mmol), and tert-butanol (t-BuOH) (1.0 mL) were added dropwise to a V-vial and stirred at 90 for 30 hours. Whether or not the reaction proceeds was confirmed by TLC, and extraction with dichloromethane (DCM) and filtration through celite were performed to complete the reaction. The extracted organic layer was dried over anhydrous magnesium sulfate and filtered. A solvent was removed and then separation was performed by column chromatography to obtain 1,3,4-triphenyl-1H-2,1-benzoxaphosphinine 1-oxide (58 mg, 98%) as a target compound.

$^1$H NMR (400 MHz, CDCl$_3$) δ 7.98-7.92 (m, 2H), 7.64-7.57 (m, 2H), 7.55-7.50 (m, 2H), 7.45 (tt, J=7.8 Hz, 1.3 Hz, 1H), 7.41-7.30 (m, 4H), 7.29-7.27 (m, 2H), 7.24 (t, J=1.6 Hz, 1H), 7.23 (t, J=2.0 Hz, 1H), 7.18-7.08 (m, 3H), 7.05 (dd, J=7.9 Hz, 4.8 Hz, 1H)

EXAMPLE 101

Preparation of 3,4-Bis(3-methylphenyl)-1-phenyl-1H-2,1-benzoxaphosphinine 1-oxide

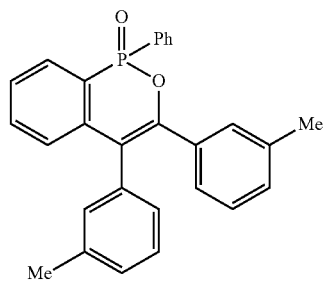 [SMILES: Cc1cccc(C2=C(c3cccc(C)c3)c3ccccc3P(=O)(c3ccccc3)O2)c1]

3,4-Bis(3-methylphenyl)-1-phenyl-1H-2,1-benzoxaphosphinine 1-oxide (38 mg, 62%) as a target compound was obtained under the condition of 90 for 30 hours, by the same reaction as the Example 100 above, except for using bis(3-methylphenyl)ethyne (47 mg, 0.23 mmol) instead of using diphenylacetylene of the Example 100 above.

$^1$H NMR (400 MHz, CDCl$_3$) δ 7.96-7.91 (m, 2H), 7.63-7.49 (m, 4H), 7.44 (tt, J=7.4 Hz, 1.3 Hz, 1H), 7.35-7.25 (m, 2H), 7.18-7.15 (m, 2H), 7.10 (s, 1H), 7.08-7.05 (m, 2H), 6.98-6.95 (m, 3H), 2.33 (s, 3H), 2.17 (s, 3H)

EXAMPLE 102

Preparation of 3,4-Bis(4-methylphenyl)-1-phenyl-1H-2,1-benzoxaphosphinine 1-oxide

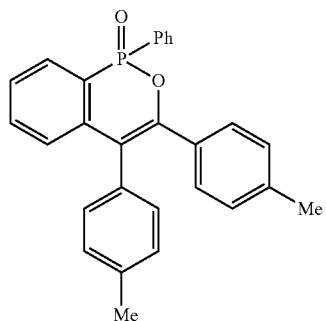 [SMILES: Cc1ccc(C2=C(c3ccc(C)cc3)c3ccccc3P(=O)(c3ccccc3)O2)cc1]

3,4-Bis(4-methylphenyl)-1-phenyl-1H-2,1-benzoxaphosphinine 1-oxide (47 mg, 72%) as a target compound was obtained under the condition of 90 for 30 hours, by the same reaction as the Example 100 above, except for using bis(4-methylphenyl)ethyne (47 mg, 0.23 mmol) instead of using diphenylacetylene of the Example 100 above.

$^1$H NMR (400 MHz, CDCl$_3$) δ 7.95-7.90 (m, 2H), 7.62-7.48 (m, 4H), 7.43 (t, J=7.7 Hz, 1H), 7.33-7.29 (m, 1H), 7.21-7.13 (m, 6H), 7.05 (dd, J=8.4 Hz, 4.8 Hz, 1H), 6.92 (d, J=8.1 Hz, 2H), 2.40 (s, 3H), 2.24 (s, 3H)

EXAMPLE 103

Preparation of 3,4-Bis(4-methoxyphenyl)-1-phenyl-1H-2,1-benzoxaphosphinine 1-oxide

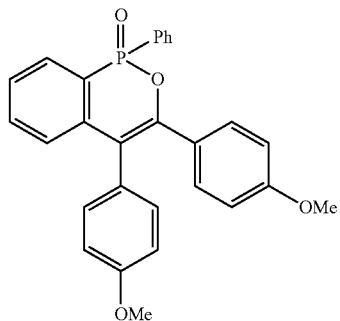 [SMILES: COc1ccc(C2=C(c3ccc(OC)cc3)c3ccccc3P(=O)(c3ccccc3)O2)cc1]

3,4-Bis(4-methoxyphenyl)-1-phenyl-1H-2,1-benzoxaphosphinine 1-oxide (65 mg, 95%) as a target compound was obtained under the condition of 90 for 30 hours, by the same reaction as the Example 100 above, except for using bis(4-methoxyphenyl)ethyne (55 mg, 0.23 mmol) instead of using diphenylacetylene of the Example 100 above.

$^1$H NMR (400 MHz, CDCl$_3$) δ 7.95-7.90 (m, 2H), 7.63-7.49 (m, 4H), 7.43 (t, J=7.7 Hz, 1H), 7.33-7.28 (m, 1H), 7.19 (app d, J=8.9 Hz, 4H), 7.07 (dd, J=8.04 Hz, 4.82 Hz, 1H), 6.94 (d, J=8.7 Hz, 2H), 6.65 (app d, J=9.0 Hz, 2H), 3.85 (s, 3H), 3.73 (s, 3H)

EXAMPLE 104

Preparation of 3,4-Bis(3-chlorophenyl)-1-phenyl-1H-2,1-benzoxaphosphinine 1-oxide

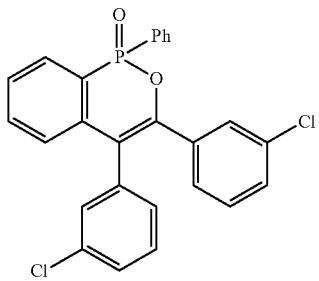 [SMILES: O=P1(c2ccccc2)OC(c2cccc(Cl)c2)=C(c2cccc(Cl)c2)c2ccccc21]

3,4-Bis(3-chlorophenyl)-1-phenyl-1H-2,1-benzoxaphosphinine 1-oxide (42 mg, 60%) as a target compound was obtained under the condition of 90 for 30 hours, by the same reaction as the Example 100 above, except for using bis(3-chlorophenyl)ethyne (57 mg, 0.23 mmol) instead of using diphenylacetylene of the Example 100 above.

$^1$H NMR (400 MHz, CDCl$_3$) δ 7.95-7.90 (m, 2H), 7.67-7.47 (m, 5H), 7.41-7.33 (m, 3H), 7.31 (d, J=1.5 Hz, 2H), 7.18-7.15 (m, 2H), 7.07-7.01 (m, 3H)

EXAMPLE 105

Preparation of 3,4-Bis(4-chlorophenyl)-1-phenyl-1H-2,1-benzoxaphosphinine 1-oxide

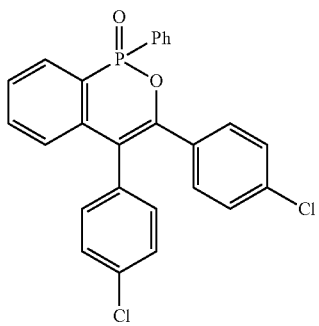 [SMILES: O=P1(c2ccccc2)OC(c2ccc(Cl)cc2)=C(c2ccc(Cl)cc2)c2ccccc21]

3,4-Bis(4-chlorophenyl)-1-phenyl-1H-2,1-benzoxaphosphinine 1-oxide (58 mg, 83%) as a target compound was obtained under the condition of 90 for 30 hours, by the same reaction as the Example 100 above, except for using bis(4-chlorophenyl)ethyne (57 mg, 0.23 mmol) instead of using diphenylacetylene of the Example 100 above.

$^1$H NMR (400 MHz, CDCl$_3$) δ 7.95-7.89 (m, 2H), 7.66-7.45 (m, 5H), 7.40-7.34 (m, 3H), 7.21 (d, J=8.2 Hz, 2H), 7.17-7.11 (m, 4H), 7.01 (dd, J=7.9 HZ, 4.8 Hz, 1H)

EXAMPLE 106

Preparation of 3,4-Bis(3-bromophenyl)-1-phenyl-1H-2,1-benzoxaphosphinine 1-oxide

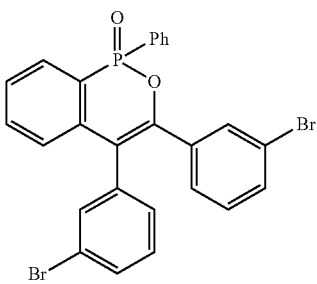 [SMILES: O=P1(c2ccccc2)OC(c2cccc(Br)c2)=C(c2cccc(Br)c2)c2ccccc21]

3,4-Bis(3-bromophenyl)-1-phenyl-1H-2,1-benzoxaphosphinine 1-oxide (36 mg, 45%) as a target compound was obtained under the condition of 90 for 30 hours, by the same reaction as the Example 100 above, except for using bis(3-bromophenyl)ethyne (77 mg, 0.23 mmol) instead of using diphenylacetylene of the Example 100 above.

$^1$H NMR (400 MHz, CDCl$_3$) δ 7.95-7.89 (m, 2H), 7.67-7.52 (m, 5H), 7.50-7.46 (m, 3H), 7.40-7.36 (m, 1H), 7.33-7.26 (m, 2H), 7.21 (d, J=7.6 Hz, 1H), 7.08-6.97 (m, 3H)

EXAMPLE 107

Preparation of 3,4-Bis(4-bromophenyl)-1-phenyl-1H-2,1-benzoxaphosphinine 1-oxide

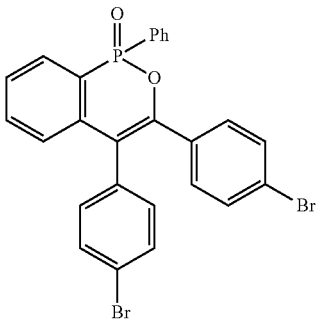 [SMILES: O=P1(c2ccccc2)OC(c2ccc(Br)cc2)=C(c2ccc(Br)cc2)c2ccccc21]

3,4-Bis(4-bromophenyl)-1-phenyl-1H-2,1-benzoxaphosphinine 1-oxide (46 mg, 56%) as a target compound was obtained under the condition of 90 for 30 hours, by the same reaction as the Example 100 above, except for using bis(4-bromophenyl)ethyne (77 mg, 0.23 mmol) instead of using diphenylacetylene of the Example 100 above.

$^1$H NMR (400 MHz, CDCl$_3$) δ 7.94-7.89 (m, 2H), 7.66-7.51 (m, 6H), 7.47 (tt, J=7.7 Hz, 1.2 Hz, 1H), 7.39-7.34 (m, 1H), 7.28 (app d, J=8.7 Hz, 2H), 7.15 (d, J=8.2 Hz, 2H), 7.09 (app d, J=8.7 Hz, 2H), 7.01 (dd, J=8.0 Hz, 4.7 Hz, 1H)

EXAMPLE 108

Preparation of 1-Phenyl-3,4-diethyl-1H-2,1-benzoxaphosphinine 1-oxide

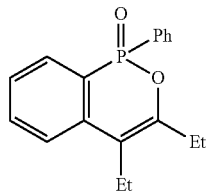 [SMILES: CCC1=C(CC)c2ccccc2P(=O)(c2ccccc2)O1]

Phenyl-3,4-diethyl-1H-2,1-benzoxaphosphinine 1-oxide (37 mg, 82%) as a target compound was obtained under the condition of 90 for 30 hours, by the same reaction as the Example 100 above, except for using 3-hexyne (19 mg, 0.23 mmol) instead of using diphenylacetylene of the Example 100 above.

$^1$H NMR (400 MHz, CDCl$_3$) δ 7.82-7.77 (m, 2H), 7.59-7.51 (m, 2H), 7.50-7.44 (m, 3H), 7.30-7.26 (m, 1H), 2.60-2.34 (m, 4H), 1.23-1.16 (m, 6H)

EXAMPLE 109

Preparation of 1-Phenyl-3,4-dibutyl-1H-2,1-benzoxaphosphinine 1-oxide

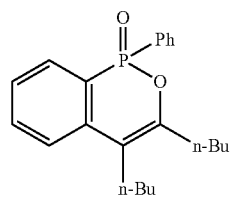

Phenyl-3,4-dibutyl-1H-2,1-benzoxaphosphinine 1-oxide (39 mg, 74%) as a target compound was obtained under the condition of 90 for 30 hours, by the same reaction as the Example 100 above, except for using 5-decyne (32 mg, 0.23 mmol) instead of using diphenylacetylene of the Example 100 above.

$^1$H NMR (400 MHz, CDCl$_3$) δ 7.81-7.75 (m, 2H), 7.59-7.55 (m, 2H), 7.51-7.44 (m, 4H), 7.31-7.26 (m, 1H), 2.60-2.40 (m, 4H), 1.64-1.50 (m, 4H), 1.49-1.28 (m, 4H), 0.98 (t, J=7.2 Hz, 3H), 0.89 (t, J=7.34 Hz, 3H)

EXAMPLE 110

Preparation of 8-M ethyl-1-(2-methylphenyl)-3,4-diphenyl-1H-2,1-benzoxaphosphinine 1-oxide

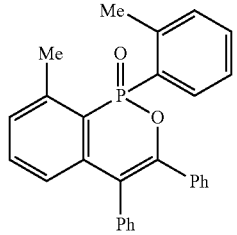 [SMILES: Cc1ccccc1P1(=O)OC(c2ccccc2)=C(c2ccccc2)c2cccc(C)c21]

8-Methyl-1-(2-methylphenyl)-3,4-diphenyl-1H-2,1-benzoxaphosphinine 1-oxide (48 mg, 76%) as a target compound was obtained under the condition of 90 for 30 hours, by the same reaction as the Example 100 above, except for using bis(2-methylphenyl)phosphinic acid (37 mg, 0.15 mmol) instead of using diphenylphosphonic acid of the Example 100 above.

$^1$H NMR (400 MHz, CDCl$_3$) δ 8.28-8.22 (m, 1H), 7.49 (tt, J=7.5 Hz, 1.4 Hz, 1H), 7.42-7.30 (m, 5H), 7.25-7.21 (m, 3H), 7.20-7.18 (m, 2H), 7.13-7.06 (m, 4H), 6.88 (dd, J=8.1 Hz, 4.5 Hz, 1H), 2.29 (s, 3H), 2.19 (s, 3H)

EXAMPLE 111

Preparation of 8-Methyl-1-(2-methylphenyl)-3,4-diethyl-1H-2,1-benzoxaphosphinine 1-oxide

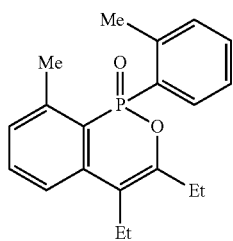 [SMILES: CCC1=C(CC)c2cccc(C)c2P(=O)(c2ccccc2C)O1]

8-Methyl-1-(2-methylphenyl)-3,4-diethyl-1H-2,1-benzoxaphosphinine 1-oxide (36 mg, 74%) as a target compound was obtained under the condition of 90 for 30 hours, by the same reaction as the Example 100 above, except for using bis(2-methylphenyl)phosphinic acid (37 mg, 0.15 mmol) instead of using diphenylphosphonic acid of the Example 100 above, and using 3-hexyne (19 mg, 0.23 mmol) instead of using diphenylacetylene of the Example 100 above.

$^1$H NMR (400 MHz, CDCl$_3$) δ 8.18-8.12 (m, 1H), 7.49-7.43 (m, 2H), 7.38-7.33 (m, 2H), 7.18 (t, J=6.5 Hz, 1H), 7.06 (dd, J=7.6 Hz, 4.3 Hz, 1H), 2.66-2.45 (m, 4H), 2.18 (s, 3H), 2.01 (s, 3H), 1.18 (td, J=7.5 Hz, 3.2 Hz, 6H)

EXAMPLE 112

Preparation of 6-Methoxy-1-(4-methoxyphenyl)-3,4-diphenyl-1H-2,1-benzoxaphosphinine 1-oxide

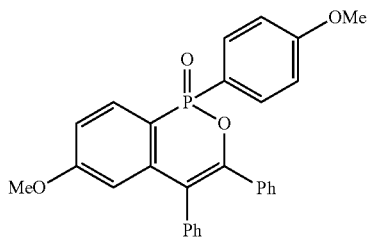 [SMILES: COc1ccc(P2(=O)OC(c3ccccc3)=C(c3ccccc3)c3cc(OC)ccc32)cc1]

6-Methoxy-1-(4-methoxyphenyl)-3,4-diphenyl-1H-2,1-benzoxaphosphinine 1-oxide (48 mg, 71%) as a target compound was obtained under the condition of 90 for 30 hours, by the same reaction as the Example 100 above, except for using bis(4-methoxyphenyl)phosphinic acid (42 mg, 0.15 mmol) instead of using diphenylphosphonic acid of the Example 100 above.

$^1$H NMR (400 MHz, CDCl$_3$) δ 7.84 (dd, J=12.7 Hz, 8.7 Hz, 2H), 7.54 (dd, J=13.7 Hz, 8.4 Hz, 1H), 7.39-7.32 (m, 3H), 7.28-7.26 (m, 2H), 7.23-7.20 (m, 2H), 7.15-7.07 (m, 3H), 7.00 (dd, J=8.7 Hz, 2.8 Hz, 2H), 6.87 (dt, J=8.4 Hz, 2.3 Hz, 1H), 6.54-6.52 (m, 1H), 3.86 (s, 3H), 3.67 (s, 3H)

EXAMPLE 113

Preparation of 6-Methoxy-1-(4-methoxyphenyl)-3,4-diethyl-1H-2,1-benzoxaphosphinine 1-oxide

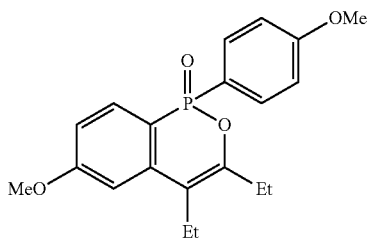 [SMILES: CCC1=C(CC)c2cc(OC)ccc2P(=O)(c2ccc(OC)cc2)O1]

6-Methoxy-1-(4-methoxyphenyl)-3,4-diethyl-1H-2,1-benzoxaphosphinine 1-oxide (44 mg, 82%) as a target compound was obtained under the condition of 90 for 30 hours, by the same reaction as the Example 100 above, except for using bis(4-methoxyphenyl)phosphinic acid (42 mg, 0.15 mmol) instead of using diphenylphosphonic acid of the Example 100 above, and using 3-hexyne (19 mg, 0.23 mmol) instead of using diphenylacetylene of the Example 100 above.

$^1$H NMR (400 MHz, CDCl$_3$) δ 7.70 (dd, J=12.6 Hz, 8.8 Hz, 2H), 7.42 (dd, J=13.8 Hz, 8.4 Hz, 1H), 6.98-6.93 (m, 3H), 6.82 (dt, J=8.4 Hz, 2.3 Hz, 1H), 3.86 (s, 3H), 2.60-2.41 (m, 4H), 1.21 (t, J=7.5 Hz, 3H)

EXAMPLE 114

Preparation of 6-Chloro-1-(4-chlorophenyl)-3,4-bis(4-methoxyphenyl)-1H-2,1-benzoxaphosphinine 1-oxide

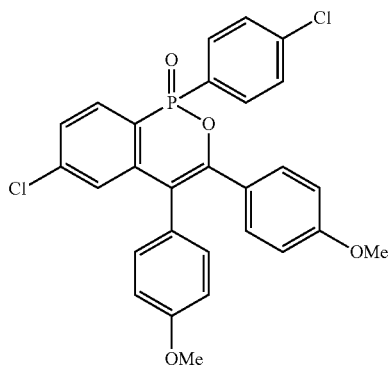 [SMILES: COc1ccc(C2=C(c3ccc(OC)cc3)c3cc(Cl)ccc3P(=O)(c3ccc(Cl)cc3)O2)cc1]

6-Chloro-1-(4-chlorophenyl)-3,4-bis(4-methoxyphenyl)-1H-2,1-benzoxaphosphinine 1-oxide (60 mg, 76%) as a target compound was obtained under the condition of 90 for 30 hours, by the same reaction as the Example 100 above, except for using bis(4-chlorophenyl)phosphinic acid (43 mg, 0.15 mmol) instead of using diphenylphosphinic acid of the Example 100 above, and using bis(4-methoxyphenyl)ethyne (55 mg, 0.23 mmol) instead of using diphenyl acetylene of the Example 100 above.

$^{1}$H NMR (400 MHz, CDCl$_3$) δ 7.87-7.81 (m, 2H), 7.52-7.44 (m, 3H), 7.29 (td, J=8.1 Hz, 2.1 Hz, 1H), 7.17-7.14 (m, 4H), 7.05 (dd, J=4.1 Hz, 4.8 Hz, 1H), 6.95 (app d, J=8.7 Hz, 2H), 6.67-6.63 (m, 2H), 3.87 (s, 3H), 3.73 (s, 3H)

EXAMPLE 115

Preparation of 6-Chloro-1-(4-chlorophenyl)-3,4-diethyl-1H-2,1-benzoxaphosphinine 1-oxide

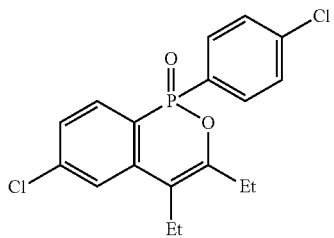 [SMILES: CCC1=C(CC)c2cc(Cl)ccc2P(=O)(c2ccc(Cl)cc2)O1]

6-Chloro-1-(4-chlorophenyl)-3,4-diethyl-1H-2,1-benzoxaphosphinine 1-oxide (43 mg, 78%) as a target compound was obtained under the condition of 90 for 30 hours, by the same reaction as the Example 100 above, except for using bis(4-chlorophenyl)phosphinic acid (43 mg, 0.15 mmol) instead of using diphenylphosphonic acid of the Example 100 above, and using 3-hexyne (19 mg, 0.23 mmol) instead of using diphenylacetylene of the Example 100 above.

$^{1}$H NMR (400 MHz, CDCl$_3$) δ 7.73-7.68 (m, 2H), 7.48-7.45 (m, 3H), 7.39 (dd, J=13.9 Hz, 8.1 Hz, 1H), 7.29-7.26 (m, 1H), 2.63-2.44 (m, 4H), 1.21 (t, J=7.3 Hz, 3H), 1.18 (t, J=7.4 Hz, 3H)

EXAMPLE 116

Preparation of 1-(Naphthalen-1-yl)-3,4-bis(4-methoxyphenyl)-1H-naphtho[1,2-c][1,2]oxaphosphinine 1-oxide

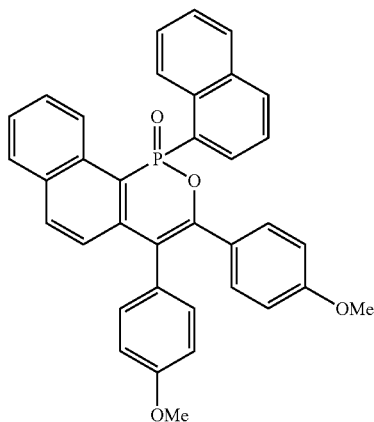 [SMILES: COc1ccc(C2=C(c3ccc(OC)cc3)c3ccc4ccccc4c3P(=O)(c3cccc4ccccc34)O2)cc1]

1-(Naphthalen-1-yl)-3,4-bis(4-methoxyphenyl)-1H-naphtho[1,2-c][1,2]oxaphosphinine 1-oxide (66 mg, 80%) as a target compound was obtained under the condition of 90 for 30 hours, by the same reaction as the Example 100 above, except for using bis(1-naphthyl)phosphinic acid (48 mg, 0.15 mmol) instead of using diphenylphosphinic acid of the Example 100 above, and using bis(4-methoxyphenyl)ethyne (55 mg, 0.23 mmol) instead of using diphenylacetylene of the Example 100 above.

$^{1}$H NMR (400 MHz, CDCl$_3$) δ 8.43-8.38 (m, 2H), 8.24 (d, J=8.0 Hz, 1H), 8.05 (d, J=8.2 Hz, 1H), 7.87-7.85 (m, 2H), 7.73 (d, J=8.1 Hz, 1H), 7.58 (td, J=7.6 Hz, 2.9 Hz, 1H), 7.44-7.40 (m, 2H), 7.35 (d, J=7.8 Hz, 1H), 7.32-7.23 (m, 4H), 7.11 (d, J=8.7 Hz, 2H), 6.98 (d, J=8.4 Hz, 2H), 6.56 (d, J=8.8 Hz, 2H), 3.86 (s, 3H), 3.66 (s, 3H)

EXAMPLE 117

Preparation of 1-(2,4,6-Trimethylphenyl)-3,4-diethyl-1H-2,1-benzoxaphosphinine 1-oxide

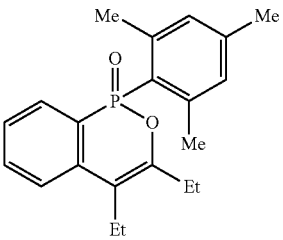 [SMILES: CCC1=C(CC)c2ccccc2P(=O)(c2c(C)cc(C)cc2C)O1]

1-(2,4,6-Trimethylphenyl)-3,4-diethyl-1H-2,1-benzoxaphosphinine 1-oxide (36 mg, 70%) as a target compound was obtained under the condition of 90 for 30 hours, by the same reaction as the Example 100 above, except for using mesityl(phenyl)phosphinic acid (39 mg, 0.15 mmol) instead of using diphenylphosphinic acid of the Example 100 above, and using 3-hexyne (19 mg, 0.23 mmol) instead of using diphenylacetylene of the Example 100 above.

$^{1}$H NMR (400 MHz, CDCl$_3$) δ 7.54-7.47 (m, 2H), 7.35-7.30 (m, 1H), 7.24-7.19 (m, 1H), 6.92 (s, 1H), 6.91 (s, 1H), 2.70-2.49 (m, 4H), 2.36 (s, 6H), 2.31 (s, 3H), 1.23 (t, J=7.9 Hz, 3H), 1.21 (t, J=7.9 Hz, 3H)

EXAMPLE 118

Preparation of N-Phenyl-3,4-diethyl-1-phenyl-1,2-dihydrobenz[c-1,2]azaphosphinine 1-oxide

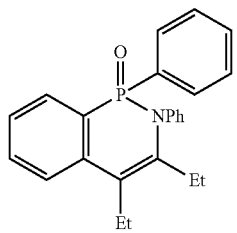

Rh(C$_5$Me$_5$)Cl$_2$]$_2$ (3.7 mg, 0.006 mmol), silver carbonate (Ag$_2$CO$_3$) (82.7 mg, 0.3 mmol), monobasic potassium phosphate (KH$_2$PO$_4$) (20.4 mg, 0.15 mmol), N,P,P-triphenylphosphinic amide (44 mg, 0.15 mmol), and tert-butyl alcohol (1.5 mL) were put into a v-vial, and 3-hexyne (34 μL, 0.3 mmol) was added dropwise thereto and stirred at 110 for 16 hours. Whether or not the reaction proceeds was confirmed by TLC, and extraction with dichloromethane (DCM) and filtration through celite were performed to complete the reaction. The extracted organic layer was dried over anhydrous magnesium sulfate and filtered. A solvent was removed and then separation was performed by column chromatography to obtain N-phenyl-3,4-diethyl-1-phenyl-1,2-dihydrobenz[c-1,2]azaphosphinine 1-oxide (39.8 mg, 71%) as a target compound.

$^1$H NMR (400 MHz, CDCl$_3$) δ 7.64 (dd, J=8.0 Hz, 4.8 Hz, 1H), 7.59-7.54 (m, 3H), 7.39 (ddd, J=7.6 Hz, 14.0 Hz, 1.0 Hz, 1H), 7.33 (tq, J=7.4 Hz, 1.5 Hz, 1H), 7.27-7.19 (m, 3H), 7.15-7.10 (m, 3H), 7.06-7.02 (m, 1H), 2.74 (q, J=4.6 Hz, 2H), 2.46-2.37 (m, 1H), 2.31-2.22 (m, 1H), 1.27 (t, J=7.4 Hz, 3H), 0.95 (t, J=7.4 Hz, 3H)

EXAMPLE 119

Preparation of N-Phenyl-3,4-di(n-butyl)-1-phenyl-1,2-dihydrobenz[c-1,2]azaphosphinine 1-oxide

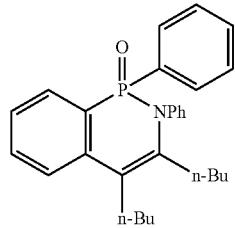

N-phenyl-3,4-di(n-butyl)-1-phenyl-1,2-dihydrobenz[c-1,2]azaphosphinine 1-oxide (43.8 mg, 68%) as a target compound was obtained under the condition of 110 for 30 hours, by the same reaction as the Example 118 above, except for using 5-decyne (53 μL, 0.3 mmol) instead of using 3-hexyne of the Example 118 above.

$^1$H NMR (400 MHz, CDCl$_3$) δ 7.62-7.53 (m, 4H), 7.40-7.30 (m, 2H), 7.25-7.19 (m, 3H), 7.16-7.09 (m, 4H), 7.08-7.01 (m, 1H), 2.73-2.61 (m, 2H), 2.40-2.32 (m, 1H), 2.24-2.16 (m, 1H), 1.75-1.30 (m, 6H), 1.18-1.03 (m, 2H), 1.00 (t, J=7.26 Hz, 3H), 0.68 (t, J=7.34 Hz, 3H)

EXAMPLE 120

Preparation of N-phenyl-1,3,4-triphenyl-1,2-dihydrobenz[c-1,2]azaphosphinine 1-oxide

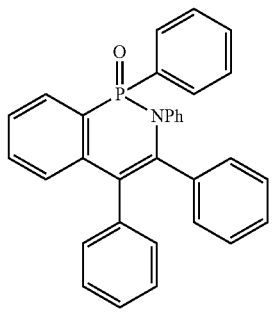

N-phenyl-1,3,4-triphenyl-1,2-dihydrobenz[c-1,2]azaphosphinine 1-oxide (64.1 mg, 91%) as a target compound was obtained under the condition of 110 for 16 hours, by the same reaction as the Example 118 above, except for using diphenylacetylene (53.5 mg, 0.3 mmol) instead of using 3-hexyne of the Example 118 above.

$^1$H NMR (400 MHz, CDCl$_3$) δ 7.72 (dd, J=6.9 Hz, 12.9 Hz, 2H), 7.53 (ddd, J=7.6 Hz, 14.2 Hz, 0.8 Hz, 1H), 7.40 (t, J=7.7 Hz, 1H), 7.34 (td, J=11.8 Hz, 1.3 Hz, 1H), 7.29-7.09 (m, 9H), 7.04 (d, J=7.6 Hz, 2H), 7.01-6.99 (m, 2H), 6.87-6.73 (m, 6H)

EXAMPLE 121

Preparation of N-Phenyl-3,4-di(m-methylphenyl)-1-phenyl-1,2-dihydrobenz[c-1,2]azaphosphinine 1-oxide

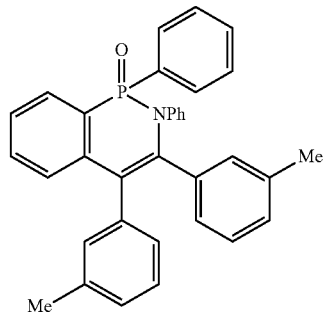

N-phenyl-3,4-di(m-methylphenyl)-1-phenyl-1,2-dihydrobenz[c-1,2]azaphosphinine 1-oxide (61.9 mg, 83%) as a target compound was obtained under the condition of 110 for 16 hours, by the same reaction as the Example 118 above, except for using 1,2-di-m-tolylethyne (61.9 mg, 0.3 mmol) instead of using 3-hexyne of the Example 118 above.

$^1$H NMR (400 MHz, CDCl$_3$) δ 7.71 (dd, J=7.0 Hz, 12.8 Hz, 2H), 7.50 (dd, J=7.3 Hz, 14.0 Hz, 1H), 7.40 (t, J=7.6 Hz, 1H), 7.34 (t, J=7.2 Hz, 1H), 7.29-7.22 (m, 3H), 7.18 (dd, J=4.9 Hz, 8.0 Hz, 1H), 7.10-7.00 (m, 5H), 6.94 (d, J=7.3 Hz, 1H), 6.85 (t, J=7.6 Hz, 3H), 6.81-6.73 (m, 2H), 6.70 (t, J=7.5 Hz, 1H), 6.57 (d, J=7.4 Hz, 1H), 2.23 (s, 3H), 1.98 (s, 3H)

EXAMPLE 122

Preparation of N-phenyl-3,4-di(p-methylphenyl)-1-phenyl-1,2-dihydrobenz[c-1,2]azaphosphinine 1-oxide

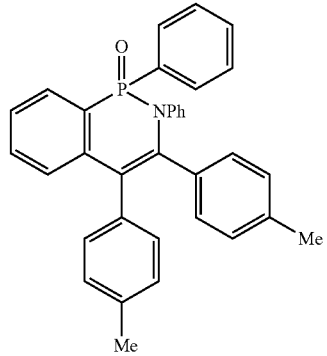

N-phenyl-3,4-di(p-methylphenyl)-1-phenyl-1,2-dihydrobenz[c-1,2]azaphosphinine 1-oxide (60.0 mg, 79%) as a target compound was obtained under the condition of 110 for 16 hours, by the same reaction as the Example 118 above, except for using 1,2-di-p-tolylethyne (61.9 mg, 0.3 mmol) instead of using 3-hexyne of the Example 118 above.

$^1$H NMR (400 MHz, CDCl$_3$) δ 7.70 (dd, J=7.0 Hz, 12.8 Hz, 2H), 7.53-7.48 (m, 1H), 7.40 (t, J=7.7 Hz, 1H), 7.34 (td,

J=11.1 Hz, 1.2 Hz, 1H), 7.29-7.22 (m, 3H), 7.16 (dd, J=5.0 Hz, 8.2 Hz, 1H), 7.08 (d, J=7.4 Hz, 2H), 7.03-7.00 (m, 4H), 6.89-6.84 (m, 4H), 6.76 (t, J=7.3 Hz, 1H), 6.63 (d, J=7.9 Hz, 2H), 2.27 (s, 3H), 2.01 (s, 3H)

EXAMPLE 123

Preparation of N-phenyl-3,4-di(p-methoxyphenyl)-1-phenyl-1,2-dihydrobenz[c-1,2]azaphosphinine 1-oxide

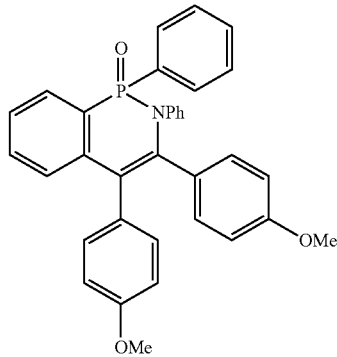

N-phenyl-3,4-di(p-methoxyphenyl)-1-phenyl-1,2-dihydrobenz[c-1,2]azaphosphinine 1-oxide (78.6 mg, 99%) as a target compound was obtained under the condition of 110 for 16 hours, by the same reaction as the Example 118 above, except for using 1,2-bis(4-methoxyphenyl)ethyne (71.4 mg, 0.3 mmol) instead of using 3-hexyne of the Example 118 above.

$^1$H NMR (400 MHz, CDCl$_3$) δ 7.70 (dd, J=7.0 Hz, 12.8 Hz, 2H), 7.50 (dd, J=7.5 Hz, 14.1 Hz, 1H), 7.40 (t, J=7.6 Hz, 1H), 7.34 (t, J=6.7 Hz, 1H), 7.28-7.22 (m, 3H), 7.18 (dd, J=4.8 Hz, 8.0 Hz, 1H), 7.10 (d, J=7.9 Hz, 2H), 7.02 (d, J=7.7 Hz, 2H), 6.91 (d, J=8.7 Hz, 2H), 6.86 (t, J=7.6 Hz, 2H), 6.76 (d, J=8.2 Hz, 3H), 6.36 (d, J=8.5 Hz, 2H), 3.73 (d, J=0.8 Hz, 3H), 3.52 (d, J=1.3 Hz, 3H)

EXAMPLE 124

Preparation of N-phenyl-3,4-di(m-chlorophenyl)-1-phenyl-1,2-dihydrobenz[c-1,2]azaphosphinine 1-oxide

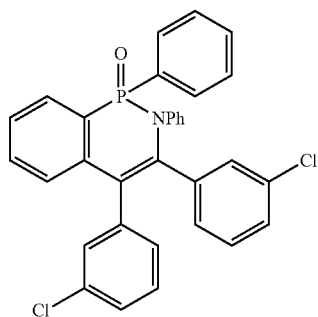

N-phenyl-3,4-di(m-chlorophenyl)-1-phenyl-1,2-dihydrobenz[c-1,2]azaphosphinine 1-oxide (55.7 mg, 69%) as a target compound was obtained under the condition of 110 for 30 hours, by the same reaction as the Example 118 above, except for using 1,2-bis(3-chlorophenyl)ethyne (74.1 mg, 0.3 mmol) instead of using 3-hexyne of the Example 118 above.

$^1$H NMR (400 MHz, CDCl$_3$) δ 7.69 (dd, J=6.9 Hz, 13.0 Hz, 2H), 7.53 (ddd, J=7.6 Hz, 14.2 Hz, 0.9 Hz, 1H), 7.47 (t, J=7.7 Hz, 1H), 7.38 (td, J=11.1 Hz, 1.41 Hz, 1H), 7.34-7.27 (m, 3H), 7.18-7.16 (m, 2H), 7.12 (dd, J=4.9 Hz, 8.1 Hz, 1H), 7.08 (s, 1H), 7.03-7.02 (m, 3H), 6.93-6.87 (m, 3H), 6.84-6.81 (m, 3H)

EXAMPLE 125

Preparation of N-phenyl-3,4-di(p-bromophenyl)-1-phenyl-1,2-dihydrobenz[c-1,2]azaphosphinine 1-oxide

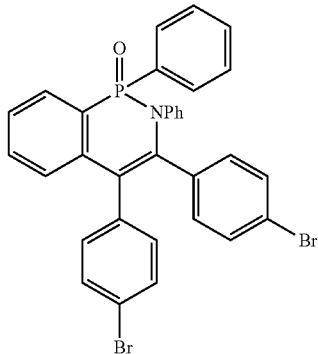

N-phenyl-3,4-di(p-bromophenyl)-1-phenyl-1,2-dihydrobenz[c-1,2]azaphosphinine 1-oxide (81.9 mg, 87%) as a target compound was obtained under the condition of 110 for 30 hours, by the same reaction as the Example 118 above, except for using 1,2-bis(4-bromophenyl)ethyne (100.8 mg, 0.3 mmol) instead of using 3-hexyne of the Example 118 above.

$^1$H NMR (400 MHz, CDCl$_3$) δ 7.68 (dd, J=7.1 Hz, 12.9 Hz, 2H), 7.51 (dd, J=7.4 Hz, 14.2 Hz, 1H), 7.43 (t, J=7.7 Hz, 1H), 7.38-7.35 (m, 3H), 7.31-7.25 (m, 3H), 7.11-7.06 (m, 3H), 7.01-7.00 (m, 4H), 6.88 (t, J=7.8 Hz, 4H), 6.81 (t, J=7.2 Hz, 1H)

EXAMPLE 126

Preparation of N-phenyl-1-methylphenyl-3,4-di(p-methoxyphenyl)-1,2-dihydro-8-methylbenz[c-1,2]azaphosphinine 1-oxide

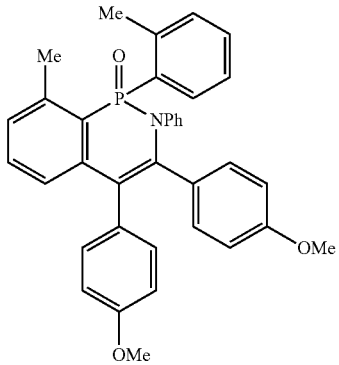

N-phenyl-1-methylphenyl-3,4-di(p-methoxyphenyl)-1,2-dihydro-8-methylbenz[c-1,2]azaphosphinine 1-oxide (72.8 mg, 87%) as a target compound was obtained under the condition of 110 for 16 hours, by the same reaction as the Example 118 above, except for using N-phenyl-P,P-bis(2-methylphenyl)phosphinic amide (48.2 mg, 0.15 mmol) instead of using N,P,P-triphenylphosphinic amide of the Example 118 above, and using 1,2-bis(4-methoxyphenyl) ethyne (71.4 mg, 0.3 mmol) instead of using 3-hexyne of the Example 118 above.

$^1$H NMR (400 MHz, CDCl$_3$) δ 7.60 (ddd, J=7.7 Hz, 14.5 Hz, 1.2 Hz, 2H), 7.42 (tt, J=11.3 Hz, 1.4 Hz, 2H), 7.29 (dd, J=4.7 Hz, 7.6 Hz, 2H), 7.23-7.16 (m, 4H), 7.06 (d, J=7.7 Hz, 2H), 6.92 (t, J=7.4 Hz, 1H), 5.07 (d, J=10.6 Hz, 1H), 2.60 (s, 6H)

EXAMPLE 127

Preparation of N-phenyl-1,3,4-tri(p-methoxyphenyl)-1,2-dihydro-6-methoxybenz[c-1,2]azaphosphinine 1-oxide

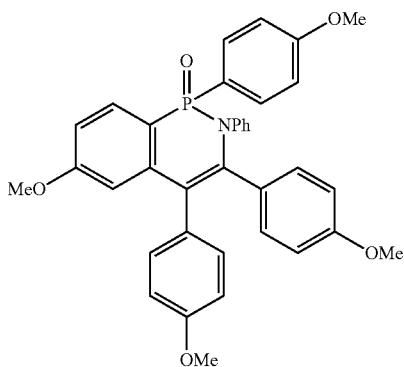

N-phenyl-1,3,4-tri(p-methoxyphenyl)-1,2-dihydro-6-methoxybenz[c-1,2]azaphosphinine 1-oxide (73.4 mg, 83%) as a target compound was obtained under the condition of 130 for 30 hours, by the same reaction as the Example 118 above, except for using P,P-bis(4-methoxyphenyl)-N-phenylphosphinic amide (53.0 mg, 0.15 mmol) instead of using N,P,P-triphenylphosphinic amide of the Example 118 above, and using 1,2-bis(4-methoxyphenyl)ethyne (71.4 mg, 0.3 mmol) instead of using 3-hexyne of the Example 118 above.

$^1$H NMR (400 MHz, CDCl$_3$) δ 7.60 (dd, J=8.7 Hz, 12.2 Hz, 2H), 7.45 (dd, J=8.5 Hz, 13.7 Hz, 1H), 7.08 (d, J=7.7 Hz, 2H), 7.00 (d, J=7.7 Hz, 2H), 6.89-6.85 (m, 4H), 6.83-6.73 (m, 6H), 6.63 (dd, J=2.4 Hz, 3.9 Hz, 1H), 6.36 (d, J=8.7 Hz, 2H), 3.76 (s, 3H), 3.75 (s, 3H), 3.65 (s, 3H), 3.55 (s, 3H)

EXAMPLE 128

Preparation of N-phenyl-1-methyoxyphenyl-3,4-di (p-bromo-phenyl)-1,2-dihydro-6-methoxybenz[c-1,2]azaphosphinine 1-oxide

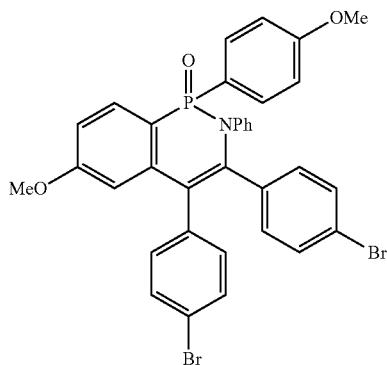

N-phenyl-1-methyoxyphenyl-3,4-di(p-bromo-phenyl)-1,2-dihydro-6-methoxybenz[c-1,2]azaphosphinine 1-oxide (86.6 mg, 84%) as a target compound was obtained under the condition of 130 for 30 hours, by the same reaction as the Example 118 above, except for using P,P-bis(4-methoxyphenyl)-N-phenylphosphinic amide (53.0 mg, 0.15 mmol) instead of using N,P,P-triphenylphosphinic amide of the Example 118 above and using 1,2-bis(4-bromophenyl) ethyne (100.8 mg, 0.3 mmol) instead of using 3-hexyne of the Example 118 above.

$^1$H NMR (400 MHz, CDCl$_3$) δ 7.58 (dd, J=8.7 Hz, 12.3 Hz, 2H), 7.46 (dd, J=8.5 Hz, 13.7 Hz, 1H), 7.36 (d, J=8.4 Hz, 2H), 7.05 (d, J=7.0 Hz, 2H), 7.01-6.97 (m, 4H), 6.89 (t, J=7.6 Hz, 2H), 6.87-6.81 (m, 4H), 6.78 (dd, J=8.8 Hz, 2.6 Hz, 2H), 6.53 (dd, J=2.3 Hz, 4.0 Hz, 1H), 3.78 (s, 3H), 3.70 (s, 3H)

EXAMPLE 129

Preparation of N-phenyl-1-fluorophenyl-3,4-di(p-methoxyphenyl)-1,2-dihydro-6-fluorobenz[c-1,2] azaphosphinine 1-oxide

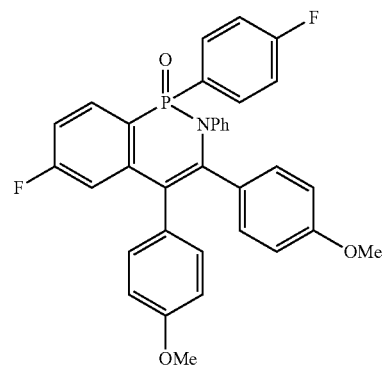

N-phenyl-1-fluorophenyl-3,4-di(p-methoxyphenyl)-1,2-dihydro-6-fluorobenz[c-1,2]azaphosphinine 1-oxide (75.5 mg, 89%) as a target compound was obtained under the condition of 110 for 16 hours, by the same reaction as the Example 118 above, except for using P,P-bis(4-fluorophenyl)-N-phenylphosphinic amide (49.4 mg, 0.15 mmol) instead of using N,P,P-triphenylphosphinic amide of the Example 118 above, and using 1,2-bis(4-methoxyphenyl)ethyne (71.4 mg, 0.3 mmol) instead of using 3-hexyne of the Example 118 above.

$^1$H NMR (400 MHz, CDCl$_3$) δ 7.71-6.65 (m, 2H), 7.52-7.45 (m, 1H), 7.07 (d, J=7.6 Hz, 2H), 7.01-6.94 (m, 5H), 6.90-6.83 (m, 5H), 6.81 (d, J=7.3 Hz, 1H), 6.76 (d, J=8.7 Hz, 2H), 6.30 (d, J=8.7 Hz, 2H), 3.74 (s, 3H), 3.54 (s, 3H)

EXAMPLE 130

Preparation of N-phenyl-1-trifluoromethylphenyl-3,4-di(p-methoxyphenyl)-1,2-dihydro-6-trifluoromethylbenz[c-1,2]azaphosphinine 1-oxide

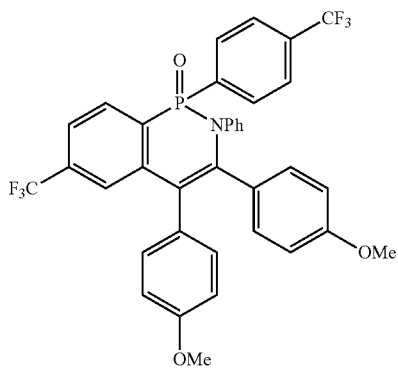

N-phenyl-1-trifluoromethylphenyl-3,4-di(p-methoxyphenyl)-1,2-dihydro-6-trifluoromethylbenz[c-1,2]azaphosphinine 1-oxide (73.9 mg, 74%) as a target compound was obtained under the condition of 110 for 16 hours, by the same reaction as the Example 118 above, except for using N-phenyl-P,P-bis(4-(trifluoromethyl)-phenyl)phosphinic amide (64.4 mg, 0.15 mmol) instead of using N,P,P-triphenylphosphinic amide of the Example 118 above, and using 1,2-bis(4-methoxyphenyl)ethyne (71.4 mg, 0.3 mmol) instead of using 3-hexyne of the Example 118 above.

$^1$H NMR (400 MHz, CDCl$_3$) δ 7.82 (dd, J=8.0 Hz, 12.4 Hz, 2H), 7.60-7.54 (m, 3H), 7.50-7.47 (m, 2H), 7.09 (d, J=7.6 Hz, 2H), 7.01 (d, J=7.4 Hz, 2H), 6.92-6.89 (m, 4H), 6.83 (d, J=7.2 Hz, 1H), 6.78 (d, J=8.6 Hz, 2H), 6.40 (d, J=8.7 Hz, 2H), 3.78 (s, 3H), 3.56 (s, 3H)

EXAMPLE 131

Preparation of N-phenyl-1-(3,5-dimethylphenyl)-3,4-di(p-methoxyphenyl)-1,2-dihydro-5,7-dimethylbenz[c-1,2]azaphosphinine 1-oxide

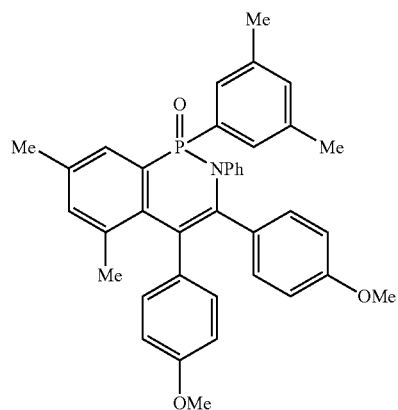

N-phenyl-1-(3,5-dimethylphenyl)-3,4-di(p-methoxyphenyl)-1,2-dihydro-5,7-dimethylbenz[c-1,2]azaphosphinine 1-oxide (52.7 mg, 60%) as a target compound was obtained under the condition of 110 for 30 hours, by the same reaction as the Example 118 above, except for using N-phenyl-P,P-bis(3,5-dimethylphenyl)phosphinic amide (52.4 mg, 0.15 mmol) instead of using N,P,P-triphenylphosphinic amide of the Example 118 above, and using 1,2-bis(4-methoxyphenyl)ethyne (71.4 mg, 0.3 mmol) instead of using 3-hexyne of the Example 118 above.

$^1$H NMR (400 MHz, CDCl$_3$) δ 7.35 (d, J=13.0 Hz, 2H), 7.25 (d, J=13.5 Hz, 2H), 7.09 (s, 1H), 7.03-7.01 (m, 3H), 7.00-6.96 (m, 4H), 6.77 (dt, J=9.5 Hz, 2.5 Hz, 2H), 6.59 (dt, J=9.7 Hz, 2.5 Hz, 2H), 6.41 (dt, J=9.5 Hz, 2.5 Hz, 2H), 3.70 (s, 3H), 3.59 (s, 3H), 2.33 (s, 3H), 2.29 (s, 3H), 2.23 (s, 6H)

EXAMPLE 132

Preparation of N-phenyl-1-thiophen-2-yl-3,4-di(p-methoxyphenyl)-1,2-dihydrothieno[2,3-c][1,2]azaphosphinine 1-oxide

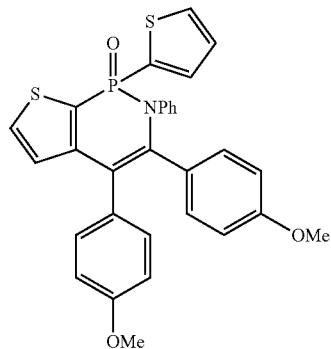

N-phenyl-1-thiophen-2-yl-3,4-di(p-methoxyphenyl)-1,2-dihydrothieno[2,3-c][1,2]azaphosphinine 1-oxide (75.6 mg, 93%) as a target compound was obtained under the condition of 110 for 16 hours, by the same reaction as the Example 118 above, except for using P,P-bis(thiophen-2-yl)-N-phenyl-phosphinic amide (45.8 mg, 0.15 mmol) instead of using N,P,P-triphenylphosphinic amide of the Example 118 above, and using 1,2-bis(4-methoxyphenyl)ethyne (71.4 mg, 0.3 mmol) instead of using 3-hexyne of the Example 118 above.

$^1$H NMR (400 MHz, CDCl$_3$) δ 7.57 (t, J=5.3 Hz, 2H), 7.46 (ddd, J=3.6 Hz, 7.9 Hz, 1.0 Hz, 1H), 7.07 (d, J=6.6 Hz, 4H), 6.98-6.96 (m, 1H), 6.93 (t, J=7.8 Hz, 2H), 6.87-6.81 (m, 4H), 6.73 (d, J=8.4 Hz, 2H), 6.37 (d, J=8.9 Hz, 2H), 3.73 (s, 3H), 3.55 (s, 3H)

EXAMPLE 133

Preparation of N-phenyl-1-thiophen-2-yl-3,4-di(p-bromophenyl)-1,2-dihydrothieno[2,3-c][1,2]azaphosphinine 1-oxide

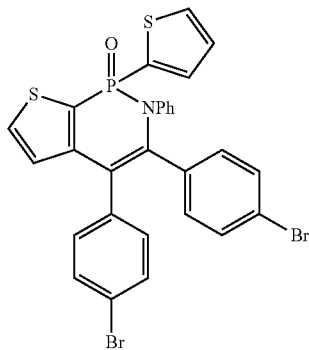

N-phenyl-1-thiophen-2-yl-3,4-di(p-bromophenyl)-1,2-dihydrothieno[2,3-c][1,2]azaphosphinine 1-oxide (55.6 mg, 58%) as a target compound was obtained under the condition of 110 for 16 hours, by the same reaction as the Example 118 above, except for using P,P-bis(thiophen-2-yl)-N-phenyl-phosphinic amide (45.8 mg, 0.15 mmol) instead of using N,P,P-triphenylphosphinic amide of the Example 118 above, and using 1,2-bis(4-bromophenyl)ethyne (100.8 mg, 0.3 mmol) instead of using 3-hexyne of the Example 118 above.

$^1$H NMR (400 MHz, CDCl$_3$) δ 7.64-7.59 (m, 2H), 7.47 (ddd, J=3.6 Hz, 8.0 Hz, 1.0 Hz, 1H), 7.35 (d, J=8.1 Hz, 2H), 7.03-6.89 (m, 10H), 6.82 (d, J=8.4 Hz, 2H), 6.78 (dd, J=2.5 Hz, 5.0 Hz, 1H)

The phosphinine oxide derivative according to the present invention may have a pharmacological activity and a physiological activity, and may be used as a basic framework of a natural product and may be utilized for development of new drug and synthesis of various medical supplies.

In addition, with the preparation method of the phosphinine oxide derivative according to the present invention, various phosphinine oxide derivatives with a high yield may be prepared by a simple synthesis process using an intramolecular annulation between a phosphinic derivative and an alkyne derivative in the presence of a rhodium (Rh) catalyst or a ruthenium (Ru) catalyst.

The invention claimed is:

1. A phosphinine oxide derivative represented by the following Chemical Formula 1:

[Chemical Formula 1]

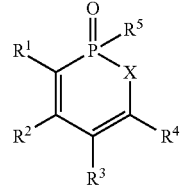

in Chemical Formula (1),

X is NR' or O;

R' is C1-C20 alkyl or C6-C20 aryl;

R$^1$ and R$^2$ are each independently hydrogen, C1-C20 alkyl or C6-C20 aryl, or R$^1$ and R$^2$ may be linked to each other by —CR$^{11}$═CR$^{12}$—CR$^{13}$═CR$^{14}$— or -L-CR$^{15}$═CR$^{16}$— to form a fused ring;

R$^{11}$ to R$^{16}$ are each independently hydrogen, C1-C20 alkyl, halo C1-C20 alkyl, C1-C20 alkoxy, C6-C20 aryl, halogen, C1-C20 alkylcarbonyl or hydroxyl, or may be linked to an adjacent substituent by C2-C7 alkenylene, C2-C7 alkylenedioxy or —CR$^{17}$═CR$^{18}$—OC(═O)— to form a fused ring;

R$^{17}$ and R$^{18}$ are each independently C1-C20 alkyl or C6-C20 aryl;

L is NR'',O or S;

R'' is hydrogen or C1-C20 alkyl;

R$^3$ and R$^4$ are each independently C1-C20 alkyl or C6-C20 aryl; and

R$^5$ is C1-C20 alkoxy, C6-C20 aryl or C3-C20 heteroaryl, wherein the alkyl and aryl of R$^1$, R$^2$, R$^3$ and R$^4$, and the alkoxy, aryl, and heteroaryl of R$^5$ may be further substituted with at least one substituent selected from the group consisting of halogen, C1-C20 alkyl, C1-C20 alkoxy and halo C1-C20 alkyl, respectively;

with a proviso that if R$^1$ and R$^2$ are linked to each other by —CR$^{11}$═CR$^{12}$—CR$^{13}$═CR$^{14}$— to form a fused ring, X is NR'.

2. The phosphinine oxide derivative of claim 1, wherein it is represented by the following Chemical Formula 2, 3, or 4:

[Chemical Formula 2]

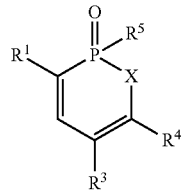

[Chemical Formula 3]

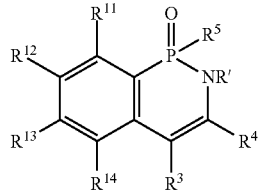

-continued

[Chemical Formula 4]

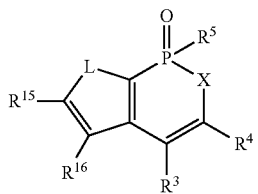

in Chemical Formulas 2 to 4, X, $R^3$, $R^4$ and $R^5$ are the same as defined in claim 1,
$R^1$ is C1-C20 alkyl or C6-C20 aryl;
$R^{11}$ to $R^{16}$ are each independently hydrogen, C1-C20 alkyl, halo C1-C20 alkyl, C1-C20 alkoxy, C6-C20 aryl, halogen, C1-C20 alkylcarbonyl, or hydroxyl, or may be linked to an adjacent substituent by

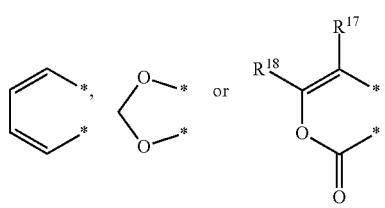

to form a fused ring;
L is NR" or S; and
R" is hydrogen or C1-C20 alkyl.

3. The phosphinine oxide derivative of claim 2, wherein X is NR' or O; R' is methyl, ethyl, propyl, butyl, pentyl, hexyl, phenyl or naphthyl; $R^1$ is methyl, ethyl, propyl, butyl, pentyl, hexyl, heptyl, octyl, phenyl, naphthyl, fluorenyl, wherein the phenyl, naphthyl or fluorenyl of $R^1$ may be further substituted with at least one substituent selected from the group consisting of methyl, ethyl, propyl, butyl, pentyl, hexyl, chloro, bromo, fluoro and iodo; $R^{11}$ to $R^{16}$ are each independently hydrogen, methyl, ethyl, propyl, butyl, pentyl, hexyl, methoxy, ethoxy, propoxy, butoxy, pentyloxy, hexyloxy, fluoro, chloro, iodo, bromo, acetyl, trifluoromethyl, phenyl, naphthyl, or hydroxyl, or $R^{11}$ to $R^{14}$ may be linked to an adjacent substituent by

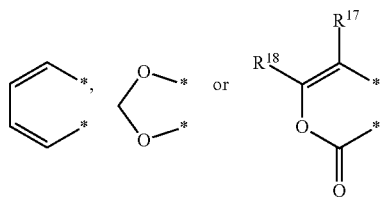

to form a fused ring, and $R^{15}$ and $R^{16}$ may be linked to each other by

to form a fused ring; $R^{17}$ and $R^{18}$ are each independently methyl, ethyl, propyl, butyl, pentyl, hexyl, phenyl or naphthyl; L is NH or S; $R^3$ and $R^4$ are each independently methyl, ethyl, propyl, butyl, pentyl, hexyl, phenyl or naphthyl, wherein the phenyl or naphthyl of $R^3$ and $R^4$ may be further substituted with at least one substituent selected from the group consisting of methyl, ethyl, propyl, butyl, pentyl, hexyl, chloro, bromo, fluoro and iodo; $R^5$ is methoxy, ethoxy, propoxy, butoxy, pentyloxy, hexyloxy, phenyl, naphthyl, thiophenyl, furyl, pyrrolyl, pyridyl, pyrimidinyl, quinolyl, triazolyl, oxazolyl or thiazolyl, wherein the phenyl of $R^5$ may be further substituted with at least one substituent selected from the group consisting of methyl, ethyl, propyl, butyl, pentyl, hexyl, trifluoromethyl, methoxy, ethoxy, propoxy, butoxy, pentyloxy, hexyloxy, chloro, bromo, fluoro and iodo.

4. The phosphinine oxide derivative of claim 3, wherein it is selected from the following compounds:

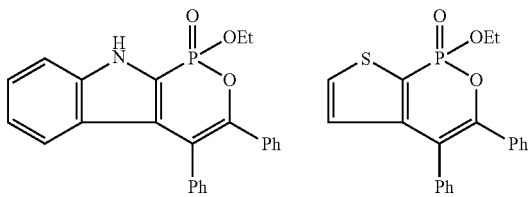

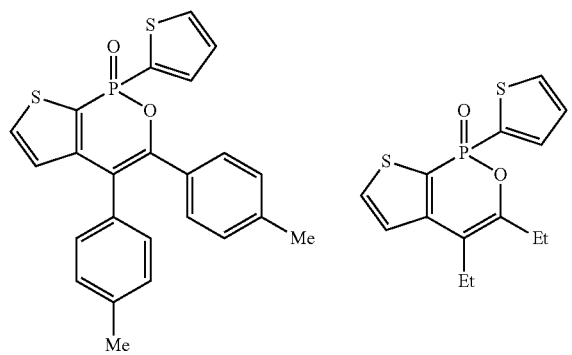

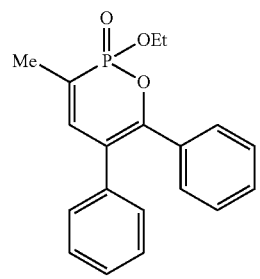

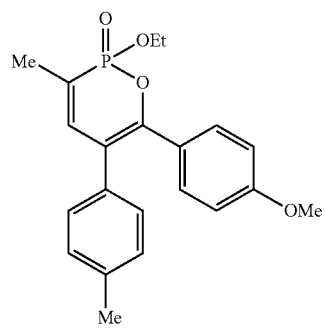

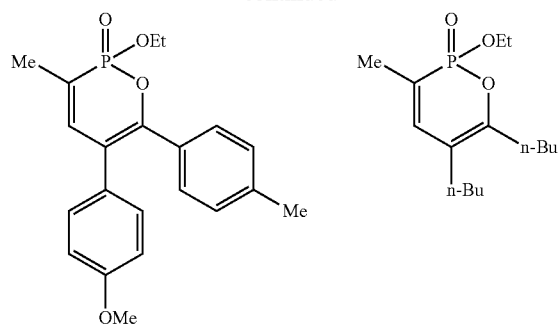
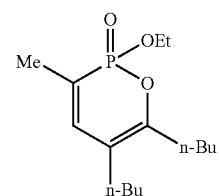
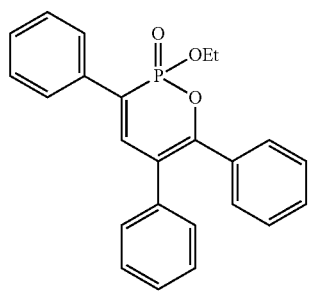
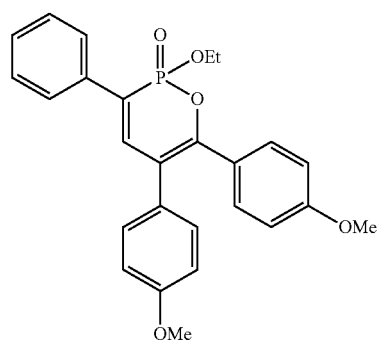
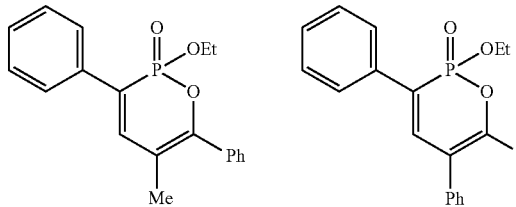
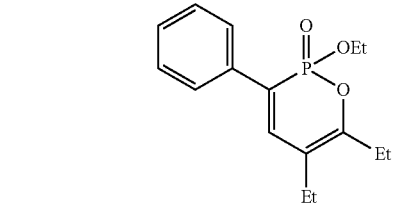
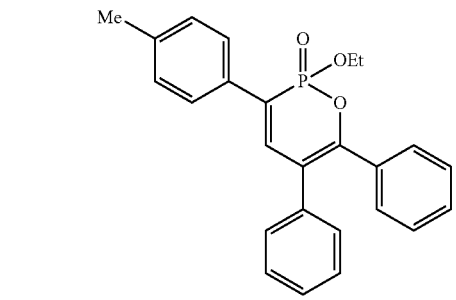
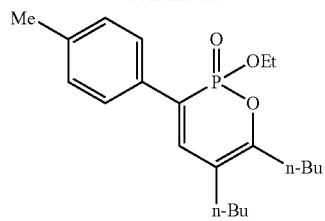
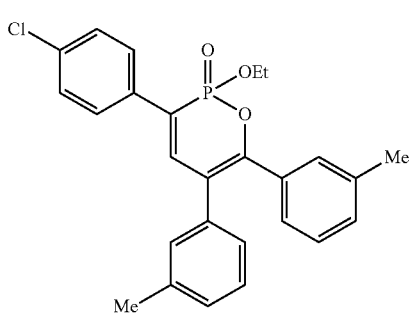
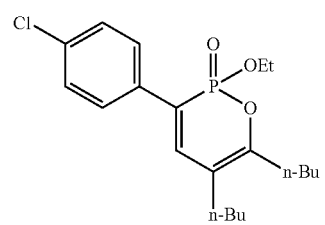
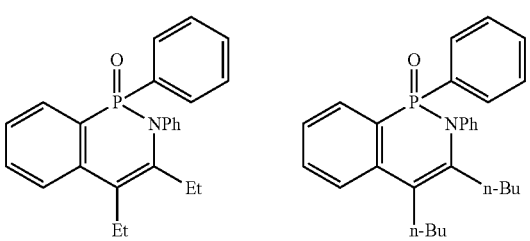
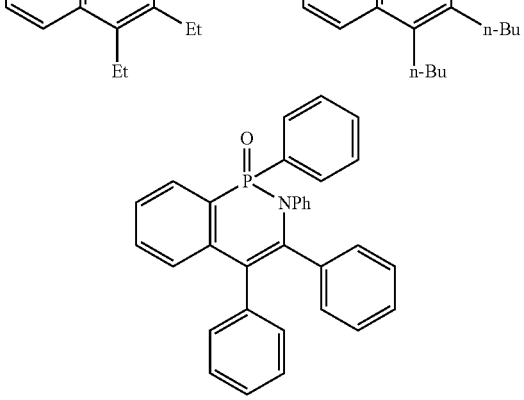
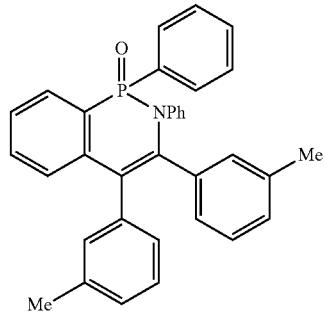

97
-continued
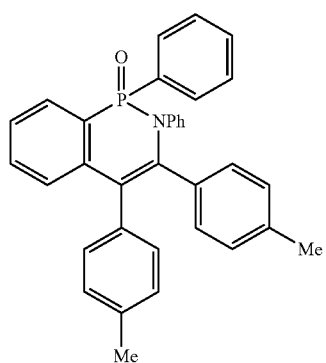
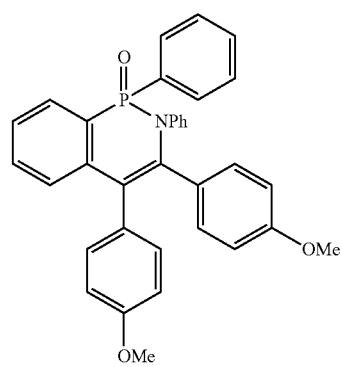
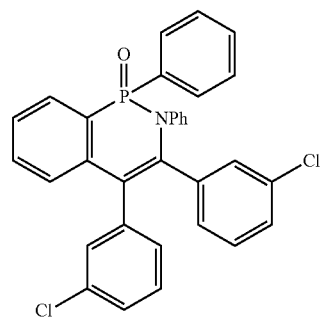
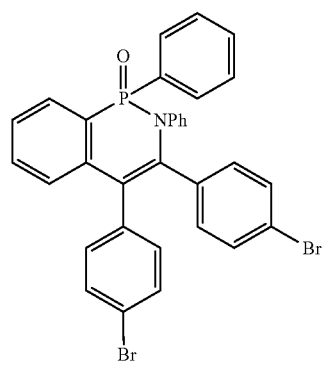
98
-continued
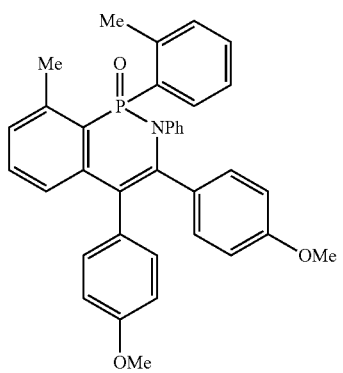
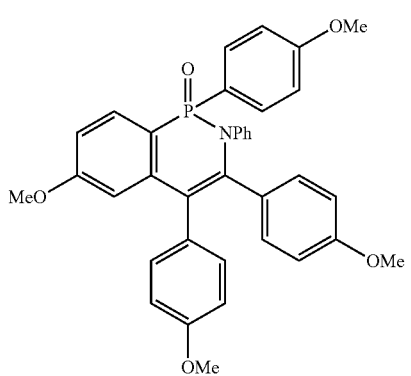
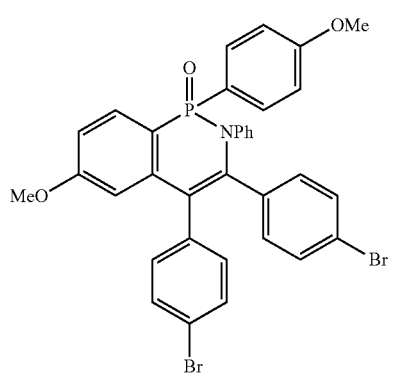
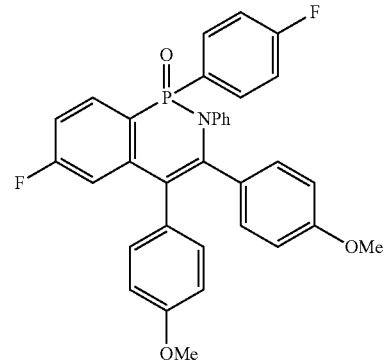

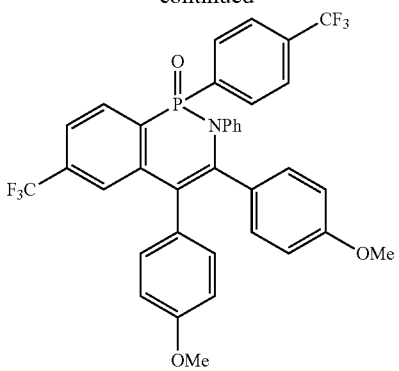

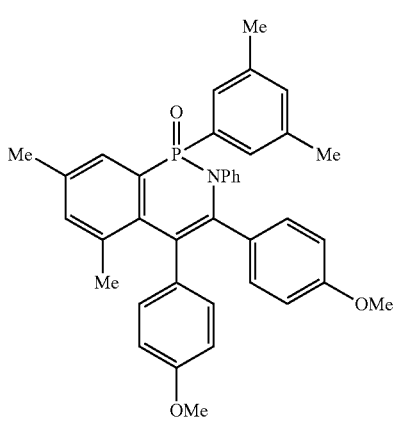

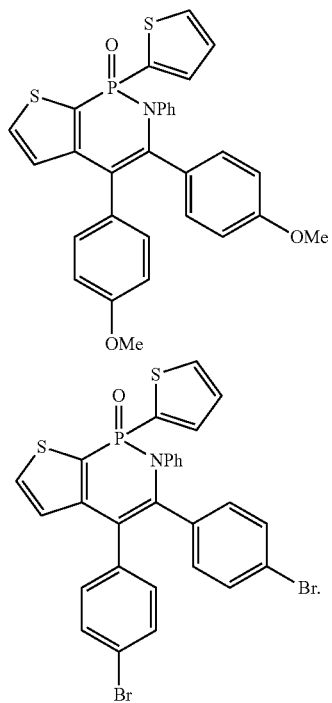

5. A preparation method of a phosphinine oxide derivative represented by the following Chemical Formula 1, by an intramolecular annulation between a phosphinic derivative represented by the following Chemical Formula 5 and an alkyne derivative represented by the following Chemical Formula 6, in the presence of a catalyst and an oxidant:

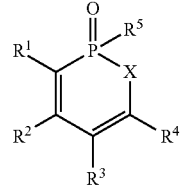

[Chemical Formula 1]

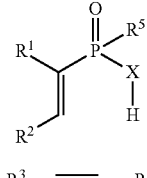

[Chemical Formula 5]

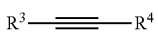

[Chemical Formula 6]

in Chemical Formulas 1, 5, and 6,

X is NR' or O;

R' is C1-C20 alkyl or C6-C20 aryl;

$R^1$ and $R^2$ are each independently hydrogen, C1-C20 alkyl or C6-C20 aryl, or $R^1$ and $R^2$ may be linked to each other by —$CR^{11}$=$CR^{12}$—$CR^{13}$=$CR^{14}$— or -L-$CR^{15}$=$CR^{16}$— to form a fused ring;

$R^{11}$ to $R^{16}$ are each independently hydrogen, C1-C20 alkyl, halo C1-C20 alkyl, C1-C20 alkoxy, C6-C20 aryl, halogen, C1-C20 alkylcarbonyl or hydroxyl, or may be linked to an adjacent substituent by C2-C7 alkenylene, C2-C7 alkylenedioxy or —$CR^{17}$=$CR^{18}$—OC(=O)— to form a fused ring;

$R^{17}$ and $R^{18}$ are each independently C1-C20 alkyl or C6-C20 aryl;

L is NR", O or S;

R" is hydrogen or C1-C20 alkyl;

$R^3$ and $R^4$ are each independently C1-C20 alkyl or C6-C20 aryl; and $R^5$ is C1-C20 alkoxy, C6-C20 aryl or C3-C20 heteroaryl, wherein the alkyl and aryl of $R^1$, $R^2$, $R^3$ and $R^4$, and the alkoxy, aryl, and heteroaryl of $R^5$ may be further substituted with at least one substituent selected from the group consisting of halogen, C1-C20 alkyl, C1-C20 alkoxy and halo C1-C20 alkyl;

with a proviso that if $R^1$ and $R^2$ are linked to each other by —$CR^{11}$=$CR^{12}$—$CR^{13}$=$CR^{14}$— to form a fused ring, X is NR'.

6. The preparation method of claim 5, wherein the catalyst is a rhodium (Rh) catalyst or a ruthenium (Ru) catalyst.

7. The preparation method of claim 6, wherein the rhodium (Rh) catalyst is one or two or more selected from the group consisting of [RhCl(cod)]$_2$ (cod=1,5-cyclooctadiene), [RhCl(C$_2$H$_4$)$_2$]$_2$, Rh(acac)$_3$, RhCl$_3$, RhCl$_3$.xH$_2$O, RhBr$_3$.xH$_2$O, Rh$_2$O$_3$, Rh$_2$O$_3$.xH$_2$O, [Rh(C$_5$Me$_5$)Cl$_2$]$_2$, (H$_2$NCH$_2$CH$_2$NH$_2$)$_3$RhCl$_3$.3H$_2$O, chlorobis(2-phenylpyridine)rhodium(III) dimer, dichloro(dimethylglyoximato)(dimethylglyoxime)rhodium (III)), trichloro [1,1,1-tri (diphenylphosphino methyl) ethane]rhodium(III), RhI$_3$, rhodium(III)2,4-pentene dionate and Rh$_2$(SO$_4$)$_3$.4H$_2$O; and the ruthenium (Ru) catalyst is one or two or more selected from the group consisting of [RuCl$_2$(p-cymene)]$_2$, [RuCl$_2$(benzene)]$_2$, (C$_5$Me$_5$)RU(CH$_3$CN)$_3$PF$_6$, Ru(CO)$_2$(PPh$_3$)$_3$, RuH$_2$(CO)(PPh$_3$)$_3$, Ru$_3$(CO)$_{12}$, [Ru(COD)Cl$_2$] (COD=1,5-cyclooctadiene), RuCl$_2$(PPh$_3$)$_3$, $RuH_2(PPh_3)_4$, $RuH_2(H_2)_2(PCy_3)_2$ (Cy =cyclohexyl), $RuCl_3$, $RuCl_3 \cdot 3H_2O$ and $Ru(acac)_3$.

8. The preparation method of claim 6, wherein the rhodium (Rh) catalyst is used in an amount of 0.01 to 0.05 equivalents based on the phosphinic derivative represented by Chemical Formula 5, and the ruthenium (Ru) catalyst is used in an amount of 0.02 to 0.2 equivalents based on the phosphinic derivative represented by Chemical Formula 5.

9. The preparation method of claim 5, wherein the oxidant is one or two or more selected from the group consisting of AgO, $Ag_2O$, AgOAc, $Ag_2CO_3$, $AgSbF_6$, AgOTf, $Cu(OAc)_2 \cdot H_2O$, CuO, $Cu_2O$, CuOAc, $Cu(OAc)_2$, $Cu(OTf)_2$, $Na_2S_2O_8$, $K_2S_2O_8$, $CuBr_2$, 2,2,6,6-tetramethyl-1-piperidinyloxy(free radical), TEMPO, $PhI(OAc)_2$, $(NH_4)_2S_2O_8$, oxygen, cesium pivalate, p-benzoquinone and tent-butyl hydroperoxide (TBHP).

10. The preparation method of claim 5, wherein the oxidant is used in an amount of 0.2 to 3.0 equivalents based on the phosphinic derivative represented by Chemical Formula 5.

11. The preparation method of claim 5, wherein the alkyne derivative represented by Chemical Formula 6 is used in an amount of 1.0 to 3.0 equivalents based on the phosphinic derivative represented by Chemical Formula 5.

12. The preparation method of claim 5, further comprising an additive or a base.

13. The preparation method of claim 12, wherein the additive is one or two or more selected from the group consisting of LiOAc, $Li_2CO_3$, NaOAc, $Na_2CO_3$, $Na_2HPO_4$, $NaHCO_3$, KOAc, $K_2CO_3$, $K_3PO_4$, $K_2HPO_4$, $KH_2PO_4$, $KPF_6$, CsF, CsOAc and CsOPiv, and the base is one or two or more selected from the group consisting of triethylamine, tetrabutylammonium chloride, lithium chloride, potassium t-butoxide, silver acetate, cesium fluoride, cesium acetate, cesium pivalate, sodium acetate, lithium acetate, potassium acetate, cesium carbonate, sodium carbonate, lithium carbonate, potassium carbonate, potassium phosphate monobasic, potassium phosphate dibasic, and potassium phosphate tribasic.

14. The preparation method of claim 13, wherein the additive is used in an amount of 0.2 to 1.0 equivalents based on the phosphinic derivative represented by Chemical Formula 5, and the base is used in an amount of 0.5 to 2.0 equivalents based on the phosphinic derivative represented by Chemical Formula 5.

\* \* \* \* \*